United States Patent
Fornaro et al.

(10) Patent No.: US 10,167,329 B2
(45) Date of Patent: Jan. 1, 2019

(54) STABILIZED INSULIN-LIKE GROWTH FACTOR POLYPEPTIDES

(71) Applicants: Mara Fornaro, Basel (CH); Thomas Huber, Basel (CH); Mauro Zurini, Basel (CH)

(72) Inventors: Mara Fornaro, Basel (CH); Thomas Huber, Basel (CH); Mauro Zurini, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/651,686

(22) PCT Filed: Dec. 16, 2013

(86) PCT No.: PCT/IB2013/060985
§ 371 (c)(1),
(2) Date: Jun. 12, 2015

(87) PCT Pub. No.: WO2014/097116
PCT Pub. Date: Jun. 26, 2014

(65) Prior Publication Data
US 2015/0329614 A1    Nov. 19, 2015

Related U.S. Application Data

(60) Provisional application No. 61/738,475, filed on Dec. 18, 2012.

(51) Int. Cl.
*C07K 14/65* (2006.01)

(52) U.S. Cl.
CPC .......... *C07K 14/65* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,396,918 B2 | 7/2008 | Glass et al. | |
| 7,781,404 B2 * | 8/2010 | Glass | C07K 14/65 |
| | | | 514/8.5 |
| 8,343,918 B2 | 1/2013 | Glass et al. | |
| 8,722,621 B2 | 5/2014 | Glass et al. | |
| 2014/0235538 A1 | 8/2014 | Glass et al. | |
| 2015/0322131 A1 | 11/2015 | Fornaro et al. | |
| 2016/0058878 A1 | 3/2016 | Jevsevar et al. | |
| 2016/0271265 A1 | 9/2016 | Fischbeck et al. | |

FOREIGN PATENT DOCUMENTS

| WO | 0040612 A1 | 7/2000 |
|---|---|---|
| WO | 2006074390 A2 | 7/2006 |
| WO | 2007146689 A2 | 12/2007 |
| WO | 2011011071 A2 | 1/2011 |
| WO | 2011011073 A1 | 1/2011 |
| WO | 2014097113 A2 | 6/2014 |
| WO | 2015049630 A1 | 4/2015 |
| WO | 2015087276 A1 | 6/2015 |

OTHER PUBLICATIONS

Jansen et al., "Effects of a single cleavage in insulin-like growth factors I and II on binding to receptors, carrier proteins and antibodies", Biochemical Journal (1990) 266:513-520.

Duguay et al., "Post-translational Processing of the Insulin-like Growth Factor-2 Precursor", Journal of Biological Chemistry (1998) 273, 29:18443-18451.

Duguay et al., "Mutational Analysis of the Insulin-like Growth Factor I Prohormone Processing Site", Journal of Biological Chemistry (1995) 270, 29:17566-17574.

* cited by examiner

*Primary Examiner* — Marianne P Allen
(74) *Attorney, Agent, or Firm* — Hong-Van M. Le

(57) ABSTRACT

This invention is in the field of IGF-1 modifications. In particular, it relates to modified IGF-polypeptides and modified IGF-1 precursor polypeptides wherein the cleavage of E-peptide is prevented. The invention also relates to the use of such polypeptides for treating muscle diseases and disorders.

14 Claims, 26 Drawing Sheets

Specification includes a Sequence Listing.

Figure 1:

| $K_D$ (nM) | hIGF1-Ea-Fc_mut_13/2_A | hIGF-1 |
|---|---|---|
| IGF-1R | 373 | 204 |

A

| ligand | EC$_{50}$ nM ± SEM |
|---|---|
| hIGF-1 | 1.8 ± 0.1 |
| hIGF1-Ea-Fc_mut_02 | 2.7* |
| hIGF1-Ea-Fc_mut_03 | 9.8** |
| hIGF1-Ea-Fc_mut_04 | 3.04* |
| hIGF1-Ea-Fc_mut_12 | 3.81* |
| hIGF1-Ea-Fc_mut_13 | 4.17* |
| hIGF1-Ea-D1-3, R37A, D71-72, R77Q-Fc | 5.26 ± 0.7# |

*n=2; **n=1; #$P<0.0001$ versus hIGF-1, t-test

B

| ligand | EC$_{50}$ nM ± SEM |
|---|---|
| hIGF-1 | 1.8 ± 0.1 |
| hIGF1-Ea-Fc_mut_04/2_E | 7.4 ± 1.3# |
| hIGF1-Ea-Fc_mut_04_E | 5.5* |
| hIGF1-Ea-Fc_mut_13/2_A | 5.7* |
| hIGF1_Ea-Fc_mut_13_A | 4.1* |

*n=2; #$P<0.0001$ versus hIGF-1, t-test

| ligand | Mean max fold increase versus control ± SD |
|---|---|
| Insulin | 20.8 ± 6.1 |
| hIGF-1 | 3.9 ± 0.8# |
| hIGF1-Ea-Fc_mut_02 | 5.9 ± 1.1#,$ |
| hIGF1-Ea-Fc_mut_03 | 8.6* |
| hIGF1-Ea-Fc_mut_04 | 12.5* |
| hIGF1-Ea-Fc_mut_12 | 21.9* |
| hIGF1-Ea-Fc_mut_13 | 15.2* |
| hIGF1-Ea-D1-3, R37A, D71-72, R77Q-Fc | 18.8 ± 3.4 |

*n=2; #$P<0.001$ versus insulin; $P<0.05$ versus IGF-1

B

| ligand | Mean max fold increase versus control ± SD |
|---|---|
| Insulin | 20.8 ± 6.1 |
| hIGF-1 | 3.9 ± 0.8# |
| hIGF1-Ea-Fc_mut_04/2_E | 5.2* |
| hIGF1-Ea-Fc_mut_04_E | 9.4* |
| hIGF1-Ea-Fc_mut_13/2_A | 5.4* |
| hIGF1-Ea-Fc_mut_13_A | 12.4* |

*n=2; ; #$P<0.001$ versus insulin

Figure 4:
A
|  | Human myoblasts | | Cynomolgus myoblasts | |
|---|---|---|---|---|
| Peptide | $EC_{50}$ (nM) ± SEM | Emax (% of control) ± SEM | $EC_{50}$ (nM) ± SEM | Emax (% of control) ± SEM |
| hIGF-1 | 4.1 ± 1.4 | 1309 ± 119 | 5.1 ± 0.7 | 786 ± 182 |
| hIGF1-Ea-Fc_mut_13/2_A | 16.8 ± 3.1* | 1069 ± 28 | 25.4 ± 4.0# | 779 ± 145 |
| hIGF1-Ea-Fc_mut_04/2_E | 10.6 ± 2.4 | 834 ± 83* | 23.8 ± 2.0# | 724 ± 152 |
*$P$ <0.05 vs Human myoblasts treated with hIGF-1. #$P$ < 0.05 vs Cynomolgus myoblasts treated with hIGF-1. ANOVA, Tukey's test
B
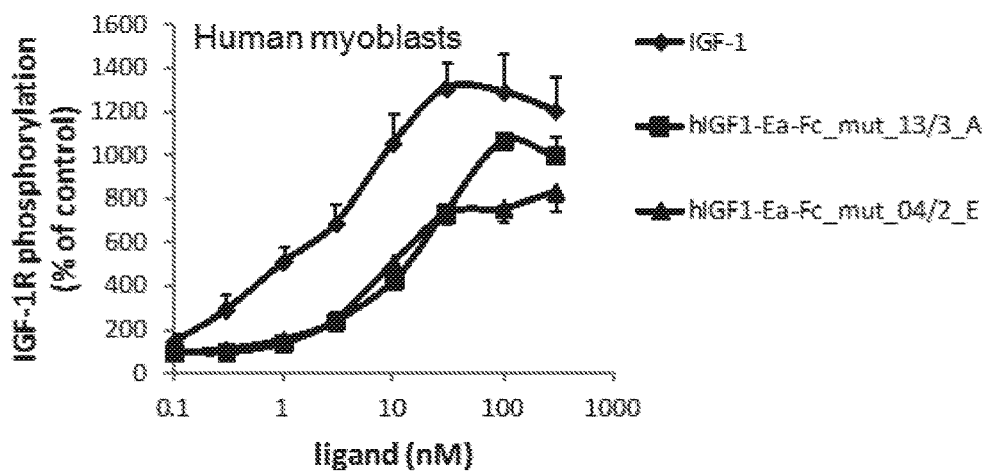
C
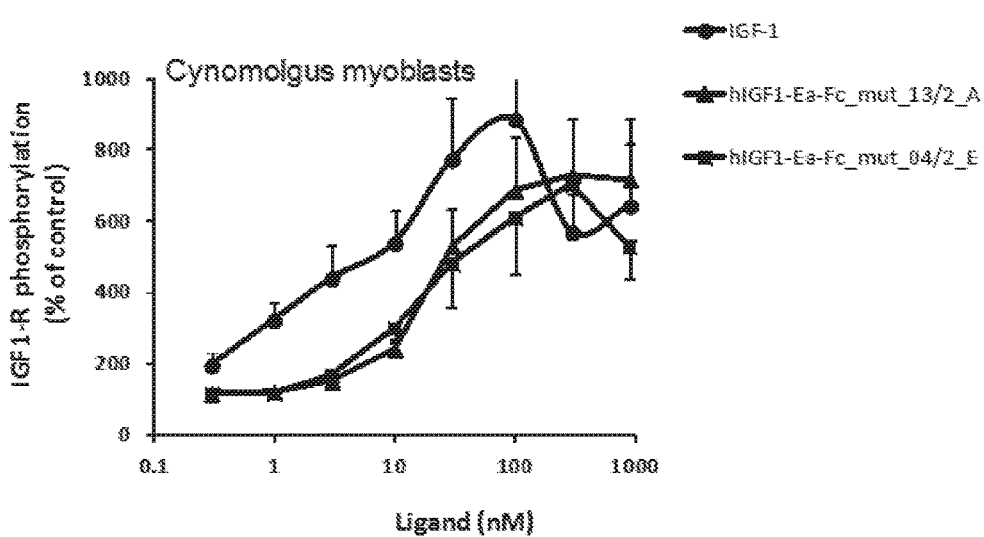

Figure 5:
A
| ligand | EC50 (nM) ± SD | max fold increase of control ± SD |
|---|---|---|
| Insulin | 11.5± 5.6** | 1.37 ± 0.08 |
| hIGF-1 | 1.3 ± 0.9 | 1.32 ± 0.06 |
| hIGF1-Ea Fc_mut_13/2_A | 4.3 ± 2.0 | 1.31 ± 0.11 |
| hIGF1-Ea Fc_mut_04/2_E | 3.7 ± 1.1 | 1.37 ± 0.10 |
**P <0.001 versus IGF-1, ANOVA, Tukey's test
B
| ligand | EC50 (nM) ± SD | max fold increase of control ± SD |
|---|---|---|
| Insulin | 9.1 ± 3.7 | 5.2 ± 1.00 |
| hIGF-1 | 5.0 ± 1.4 | 4.6 ± 0.68 |
| hIGF1-Ea Fc_mut_13/2_A | 49.9 ± 4.6**;*** | 3.2 ± 0.25# |
| hIGF1-Ea Fc_mut_04/2_E | 49.0 ± 28.4**;*** | 4.0 ± 0.47 |
# P <0.05 and P <0.01 versus Insulin; *P <0.001 versus IGF-1 ANOVA, Tukey's test
C
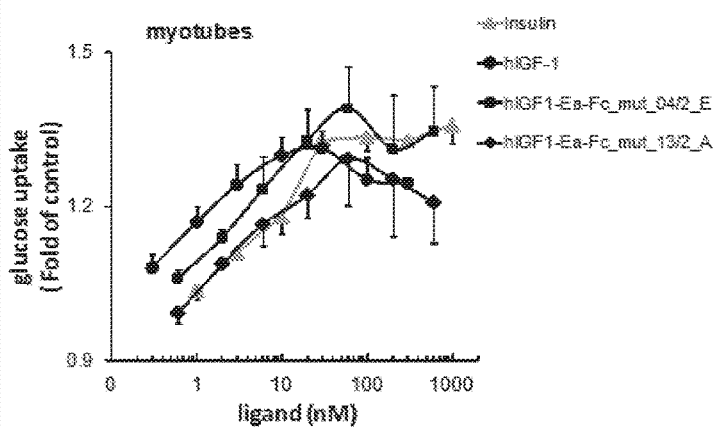
D
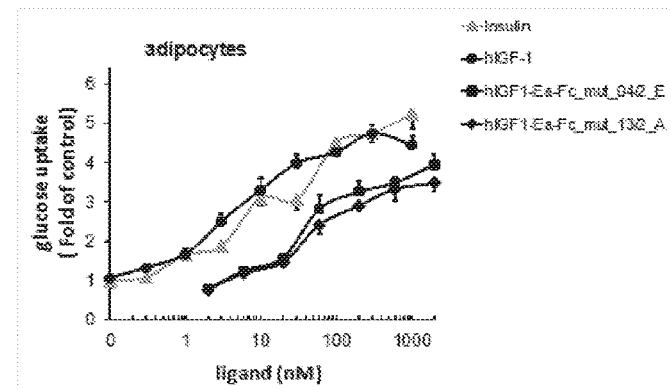

Figure 9:

| Name | Titer in supernatant (mg/l) | concentration (mg/ml) | Aggregates (%) |
|---|---|---|---|
| hIGF1-Ea-D1-3, R36Q, D68-72, R74Q, R77Q, R104Q -fc domain (SEQ ID NO.:78) | 33 | 0.88 | 37.0 |
| hIgF1-Ea-Fc_mut 13/2_A: SEQ ID NO.: 9 | 83.1 | 1.65 | 9.8 |
| hIGF1-Ea-D1-3, R36Q, G42A, D68-72, R74Q, R77Q, R104Q -fc domain (SEQ ID NO.: 79) | 11.79 | 0.49 | 37.4 |
| hIGF1-Ea-D1-3, R36Q, G42Q, D68-72, R74Q, R77Q, R104Q -fc domain (SEQ ID NO.:80) | 16.98 | 0.61 | 43.2 |
| hIGF1-Ea-D1-3, R36Q, G42P, D68-72, R74Q, R77Q, R104Q -fc domain (SEQ ID NO.: 81) | 18.57 | 0.54 | 71.9 |
| hIGF1-Ea-D1-3, R36Q, G42K, D68-72, R74Q, R77Q, R104Q -fc domain (SEQ ID NO.:82 ) | 21.6 | 0.56 | 53.8 |
| hIGF1-Ea-D1-3, R36Q, G42E, D68-72, R74Q, R77Q, R104Q -fc domain (SEQ ID NO.: 83) | 26.97 | 0.84 | 49.4 |
| hIGF1-Ea-D1-3, R36Q, G42I, D68-72, R74Q, R77Q, R104Q -fc domain (SEQ ID NO.: 84 ) | 8.7 | 0.4 | 85.5 |
| hIGF1-Ea-D1-3, R36Q, G42Y, D68-72, R74Q, R77Q, R104Q -fc domain (SEQ ID NO.: 85 ) | 13.38 | 0.41 | 48.5 |
| hIGF1-Ea-D1-3, R36Q, D42, D68-72, R74Q, R77Q, R104Q -fc domain (SEQ ID NO.: 86) | 78.6 | 1.96 | 21.0 |

D: deletion; fc domain: the Fc portion from hIgG1

Figure 17:

| Generic name | amino acid at position 42 | yield mg/L | % Aggregation | % Full length protein after challenge (CHOK1 derived cells) | % Full length protein after challenge (CHO-DUXB11 derived cells) |
|---|---|---|---|---|---|
| hIGF1-Ea-del1-3, R37A, del71-72, R74Q, R77Q, R104Q-fc (SEQ ID No. 113) (batch 1) | glycine | 11.33 | 18.3 | 21.6% ± 13.4% (n=4) | 27.06% |
| hIGF1-Ea-hFc_mut02 (SEQ ID No.: 29) | serine | 13.64 | 5.8 | 9.6% ± 13.9% (n=3) | N/A |
| hIGF1-Ea-hFc_mut03 (SEQ ID No.: 114) | glycine | 5.17 | 41.8 | 44.9% ± 12.1% (n=3) | N/A |
| hIGF1-Ea-hFc_mut04 (SEQ ID No.: 30) | glycine | 10.34 | 21.1 | 60.2% ± 12.2% (n=4) | 73.6 % |
| hIGF1-Ea-hFc_mut12 (SEQ ID No.: 116) | glycine | 8.46 | 17.7 | 44.3% ± 15.1% (n=3) | 67.9% |
| hIGF1-Ea-hFc_mut13 (SEQ ID No.: 31) | glycine | 10.18 | 24.0 | 64.2% ± 11.5% (n=4) | 80.0% |
| hIgF1-Ea-Fc_mut 13/2_E (SEQ ID No.: 08) | serine | 11.62 | 7.4 | 95.4% ± 4.4% (n=3) | 97.3%± 3.4% (n=2) |
| hIgF1-Ea-Fc_mut 13/2_A (SEQ ID No.: 09) | serine | 11.72 | 8.6 | 93.4% | 95.3% |
| hIgF1-Ea-Fc_mut 04/2_E (SEQ ID No.: 12) | serine | 11.51 | 7.3 | 95.0% ± 4.6% (n=3) | 98.7%± 1.9% (n=2) |

Figure 18:

| ligand | Mean max fold increase vs control ± SD |
|---|---|
| Insulin | 21.0 ± 6.9 |
| IGF-1 | 3.7 ± 0.8 |
| IGF-1 G42S | 3.3 ± 1.1 |
| hIGF1-Ea-mut 03 | 5.6 ± 2.0 |
| hIGF1-Ea-mut 03-G42S | 2.2 ± 0.5* |

*$P < 0.05$ versus BVS855

A

B

STABILIZED INSULIN-LIKE GROWTH FACTOR POLYPEPTIDES

This application is a U.S. National Phase filing of International Application No. PCT/IB2013/060985 filed Dec. 16, 2013, which claims priority to U.S. Application No. 61/738,475 filed Dec. 18, 2012, the contents of which are incorporated herein by reference in their entirety.

TECHNICAL FIELD

This invention is in the field of Insulin-like growth factors 1 (IGF-1) modifications. In particular, it relates to modified IGF-1 polypeptides that are linked to a human immunoglobulin Fc region.

BACKGROUND

Insulin-like growth factors (IGFs) are part of a complex system that cells use to communicate with their physiologic environment. This complex system (often referred to as the insulin-like growth factor axis) consists of two cell-surface receptors (IGF-1R and IGF-2R), two ligands (IGF-1 and IGF-2), a family of six high-affinity IGF-binding proteins (IGFBP 1-6), and associated IGFBP degrading enzymes (proteases). This system is important not only for the regulation of normal physiology but also for a number of pathological states (Glass, Nat Cell Biol 5:87-90, 2003).

The IGF axis has been shown to play roles in the promotion of cell proliferation and the inhibition of cell death (apoptosis). IGF-1 is mainly secreted by the liver as a result of stimulation by human growth hormone (hGH). Almost every cell in the human body is affected by IGF-1, especially cells in muscles, cartilage, bones, liver, kidney, nerves, skin and lungs. In addition to the insulin-like effects, IGF-1 can also regulate cell growth. IGF-1 and IGF-2 are regulated by a family of gene products known as the IGF-binding proteins. These proteins help to modulate IGF action in complex ways that involve both inhibiting IGF action by preventing binding to the IGF receptors as well as promoting IGF action through aiding delivery to the receptors and increasing IGF half-life in the blood stream. There are at least six characterized binding proteins (IGFBP1-6).

In its mature form, human IGF-1, also called somatomedin, is a small protein of 70 amino acids that has been shown to stimulate growth of a wide range of cells in culture. The IGF-1 protein is initially encoded by three known splice variant mRNAs. The open reading frame of each mRNA encodes a precursor protein containing the 70 amino acid IGF-1 (SEQ ID NO.:1) and a particular E-peptide at the C-terminus, depending on the particular IGF-1 mRNA. These E-peptides have been termed the Ea (rsvraqrhtdmpktqkevhlknasrgsagnknyrm; SEQ ID NO.:2), Eb (rsvraqrhtdmpktqkyqppstnkntksqrrkgwpkthpggeqkegteaslqirgkkkeqrreigsrnaecrgkk gk; SEQ ID NO.:3) and Ec (rsvraqrhtdmpktqkyqppstnkntksqrrkgstfeerk; SEQ ID NO.: 4) peptides and range from 35 to 87 amino acids in length and encompass a common sequence region at the N-terminus and a variable sequence region at the C-terminus. For example, the wild-type open reading frame for the IGF-1-Ea encodes a polypeptide of 135 amino acids including the leader sequence and a polypeptide of 105 amino acids without the leader sequence (gpetlcgaelvdalqfvcgdrgfyfnkptgygsssrrapqtgivdeccfrscdlrrlemycaplkpaksarsvraqrh tdmpktqkevhlknasrgsagnknyrm; SEQ ID NO.:5). In physiological expression, the E-peptides are cleaved off of the precursor by endogenous proteases to yield the mature 70 amino acid IGF-1. The availability and half-life of IGF-1 in human serum is mainly influenced and modulated by proteases and IGF-1 binding proteins (IGFBP's). IGFBP's can either inhibit or potentiate IGF-1 activities (Oh Y, et al., Characterization of the affinities of insulin-like growth factor (IGF)-binding proteins 1-4 for IGF-I, IGF-II, IGF-I/insulin hybrid, and IGF-I analogs. Endocrinology. 1993 March; 132(3):1337-44). Strategies to increase the half-life of IGF-1 have been described in the prior art. Strategies that have been contemplated are (i) the production of IGF-1 variants comprising specific mutations aiming to prevent the cleavage of IGF-1 in human serum by serine proteases, or to alleviate the negative impact of IGF-1 binding proteins on the availability or serum half-life of IGF-1 (WO200040613, WO05033134, WO2006074390, WO2007/146689);

(ii) the production of IGF-1 fusion proteins, wherein the mature IGF-1 protein is fused to a human immunoglobulin Fc region (WO2005033134, WO200040613);

(iii) the use of IGF-1 precursor proteins wherein cleavage of the E-peptide from IGF-1 by a protease is reduced by modification of the precursor protein (WO2007146689);

(iv) combinations of the above described strategies ((i)/(ii) WO05033134, (i)/(ii) WO200040613, (i)/(iii) WO2007146689).

Despite the above described strategies, the IGF-1 precursor variants fused to a human immunoglobulin Fc region remain poor drug candidates for mainly two reasons: (i) low production yield in mammalian production system, and (ii) increased binding affinity to the insulin receptor (InsR) compared to the unmodified human wildtype IGF-1, which can result in hypoglycemia, an adverse event of therapeutic concern.

Consequently, there exists a need for a technology which overcomes the above described prior art problems. The present invention addresses this need in a number of aspects.

SUMMARY OF THE INVENTION

A first subject matter of the disclosure relates to a polypeptide comprising a human IGF-1 (hIGF-1) protein, wherein the amino acid glycine at position 42 of said hIGF-1 protein is deleted or substituted, and wherein the numbering of the amino acids corresponds to SEQ ID NO.: 1.

An additional embodiment of the disclosure relates to a polypeptide comprising a human IGF-1 protein fused to an immunoglobulin Fc region of a human IgG, wherein the amino acid glycine at position 42 of the human IGF-1 protein is deleted or substituted, and wherein the numbering of the amino acids corresponds to SEQ ID NO.: 1.

Another subject matter of the disclosure relates to a polypeptide comprising a human IGF-1 precursor protein, wherein the amino acid glycine at position 42 of said human IGF-1 precursor protein is deleted or substituted, and wherein the numbering of the amino acids corresponds to SEQ ID NO.: 5.

An additional embodiment of the disclosure relates to a polypeptide comprising a human IGF-1 precursor protein fused to an immunoglobulin Fc region of a human IgG, wherein the amino acid glycine at position 42 of the human IGF-1 precursor protein is deleted or substituted, and wherein the numbering of the amino acids corresponds to SEQ ID NO.: 5.

In a certain embodiment the disclosure relates to the above described polypeptides, wherein the amino acid glycine at position 42 is deleted or substituted by serine.

In an additional embodiment the above mentioned human IGF-1 protein comprises additional deletions or mutations at amino acids G1, P2, E3, R36, R37, K68, S69 and/or A70.

In an additional embodiment the above mentioned human IGF-1 precursor protein comprises an Ea-peptide and additional deletions or mutations of amino acids G1, P2, E3, R36, R37, K68, S69, A70, R71, S72, R74, R77 G96, S97, A98, G99, N100, K101, N102, Y103, Q104 and/or M105.

In yet another embodiment, which may be combined with the preceding embodiments of the disclosure, the human IGF-1 precursor protein and the Fc region are separated by a peptide hinge region.

Accordingly, the disclosure also relates to the above described human IGF-1 precursor protein, wherein the peptide hinge region is selected from the group consisting of peptides hinge 1 (SEQ ID NO.: 22), hinge 2 (SEQ ID NO.: 23) and hinge 3 (SEQ ID NO.: 24).

In a particular embodiment the above described human IGF-1 precursor proteins when being mutated in the Ea-peptide at amino acids R74, R77 and/or R104, said amino acids R74, R77 and R104 are mutated to glutamine (Q).

A polypeptide comprising or consisting of a human IGF-1 protein or a human IGF-1 precursor protein as described above, wherein
a. amino acids E3, R71 and S72 are deleted,
b. amino acid G42 is deleted or substituted by serine, and
c. amino acid R37 is mutated to alanine and wherein the numbering of the amino acids corresponds to SEQ ID NO.: 5.

Another particular embodiment of the disclosure relates to the above described human IGF-1 precursor protein, wherein the E-peptide is the Ea-peptide and wherein
a. amino acids G1, P2, E3, K68, S69, A70, R71 and S72 are deleted,
b. amino acid G42 is deleted or mutated to serine, and
c. amino acids R36, R74, R77 and R104 are mutated to glutamine
d. amino acid R37 is mutated to alanine and wherein the numbering of the amino acids corresponds to SEQ ID NO.: 5.

Another particular embodiment of the disclosure relates to the above described human IGF-1 precursor protein, wherein the E-peptide is the Ea-peptide and wherein
a. amino acids G1, P2, E3, K68, S69, A70, R71, S72, G96, S97, A98, G99, N100, K101, N102, Y103, Q104 and/or M105 are deleted,
b. amino acid G42 is deleted or mutated to serine, and
c. amino acids R36, R74 and R77 are mutated to glutamine, and
d. amino acid R37 is mutated to alanine and wherein the numbering of the amino acids corresponds to SEQ ID NO.: 5.

Likewise, the disclosure relates to the above described human IGF-1 precursor protein, wherein the E-peptide is the Ea-peptide and wherein
a. amino acids G1, P2, E3, K68, S69, A70, R71 and S72 are deleted,
b. amino acid G42 is deleted or mutated to serine,
c. amino acids R74, R77 and R104 are mutated to glutamine, and
d. amino acid R37 is mutated to glutamic acid and wherein the numbering of the amino acids corresponds to SEQ ID NO.: 5.

Likewise, the disclosure relates to the above described human IGF-1 precursor protein, wherein the E-peptide is the Ea-peptide and wherein a. amino acids G1, P2, E3, K68, S69, A70, R71, S72, G96, S97, A98, G99, N100, K101, N102, Y103, Q104 and/or M105 are deleted,
b. amino acid G42 is deleted or mutated to serine,
c. amino acids R74 and R77 are mutated to glutamine, and
d. amino acid R37 is mutated to glutamic acid and wherein the numbering of the amino acids corresponds to SEQ ID NO.: 5.

In a furthermore particular embodiment the disclosure relates to the above described human IGF-1 precursor Fc fusion protein, wherein the E-peptide is the Ea-peptide and wherein
a. amino acids G1, P2, E3, K68, S69, A70, R71 and S72 are deleted,
b. amino acid G42 is deleted or mutated to serine, and
c. amino acids R36, R74, R77 and R104 are mutated to glutamine,
d. amino acid R37 is mutated to alanine, wherein the numbering of the amino acids corresponds to SEQ ID NO.: 5, and
e. wherein the IGF-1 precursor protein and the Fc region are separated by the hinge peptide hinge 1 (SEQ ID NO.:22).

Additionally, the disclosure relates to the above described human IGF-1 precursor Fc fusion protein, wherein the E-peptide is the Ea-peptide and wherein
a. amino acids G1, P2, E3, K68, S69, A70, R71 and S72 are deleted,
b. amino acid G42 is deleted or mutated to serine,
c. amino acids R74, R77 and R104 are mutated to glutamine,
d. amino acid R37 is mutated to glutamic acid, wherein the numbering of the amino acids corresponds to SEQ ID NO.: 5, and
e. wherein the IGF-1 precursor protein and the Fc region are separated by the hinge peptide hinge 3 (SEQ ID NO.: 24).

In a certain embodiment the disclosure relates to the above described polypeptides, wherein the Fc region is modified to modulate its binding to Fc receptor.

Accordingly, the disclosure relates to the above described human IGF-1 precursor Fc fusion protein, wherein the Fc region is modified to
I. reduce its affinity for Fc receptor;
II. reduce ADCC activity; or
III. prevent ADCC activity.

Another particular embodiment of the disclosure relates to the above described human IGF-1 precursor Fc fusion proteins comprising SEQ ID NO.: 8, or SEQ ID NO.: 9, or SEQ ID NO.: 10, or SEQ ID NO.: 11, or SEQ ID NO.: 12, or SEQ ID NO.: 13, or SEQ ID NO.: 14, or SEQ ID NO.: 27.

In a certain embodiment, which may be combined with the preceding embodiments of the disclosure, the human IGF-1 precursor Fc fusion protein is glycosylated.

In another aspect, the disclosure relates to a polynucleotide comprising a nucleic acid molecule encoding the above described human IGF-1 precursor Fc fusion proteins. Accordingly, the disclosure relates to a polynucleotide comprising the nucleic acid molecule as depicted in SEQ ID NO.:15 or SEQ ID NO.: 16 or SEQ ID NO.: 17 or SEQ ID NO.: 18 or SEQ ID NO.: 19 or SEQ ID NO.: 20 or SEQ ID NO.: 21.

The disclosure furthermore provides for a pharmaceutical composition comprising a polypeptide comprising any one of the above disclosed human IGF-1 precursor proteins for use in therapy.

In another embodiment of the disclosure, the above mentioned therapeutic use is the treatment of a muscle disorder in a patient in need thereof. In a particular embodiment of the disclosure, the therapeutic use is the treatment of burn patients suffering from loss of lean body mass and/or muscle wasting or the treatment of COPD patients, or the treatment of Kennedy disease patients, or the treatment of chronic kidney disease patients.

In an additional embodiment of the disclosure, the muscle disorder described above is muscle atrophy. Accordingly, in some aspects of the disclosure, the therapeutic use is the treatment of obesity-associated sarcopenia, sarcopenia, and diabetes-associated muscle atrophy.

The disclosure furthermore provides for a method of treating a muscle disorder in a patient in need thereof, the method comprising administering a therapeutically effective amount of the above described human IGF-1 precursor protein of the invention.

Accordingly, in one particular embodiment, the disclosure relates to a method of treating burn patients suffering from loss of lean body mass and/or muscle wasting, or a method of treating COPD patients, or a method of treating Kennedy disease patients, or a method of treating chronic kidney disease patients Furthermore, the disclosure provides a method of treating a muscle disorder in a patient in need thereof, wherein the muscle disorder is a muscle atrophy selected from the group consisting of obesity-associated sarcopenia, sarcopenia, and diabetes-associated muscle atrophy.

In another embodiment, the disclosure relates to an IGF-1 polypeptide or an IGF-1 precursor polypeptide as described above, wherein the amino acid glycine at position 42 is deleted. In another embodiment, the disclosure relates to an IGF-1 polypeptide or an IGF-1 precursor polypeptide as described above, wherein said protein is pegylated.

BRIEF DESCRIPTION OF THE DRAWINGS

FIG. 1: Binding affinity for IGF-1R

High affinity binding of hIGF-1 and IGF-1 variants to rhIGF1R was measured using surface plasmon resonance (Biacore).

Figure 2:
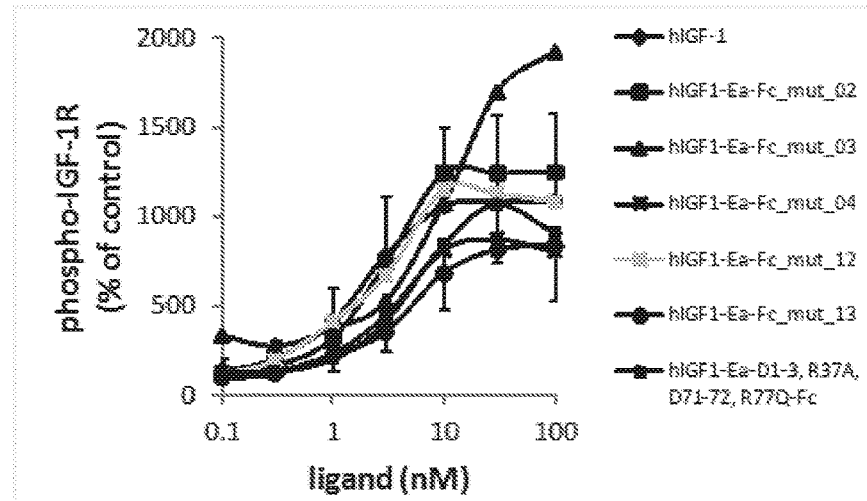
Figure 2:
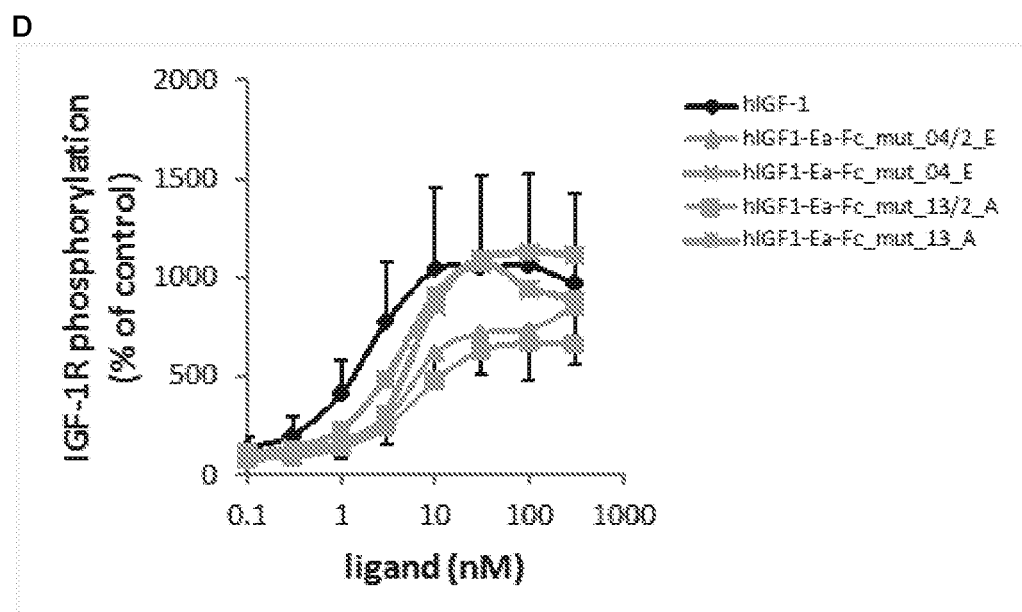

FIG. 2 (A-D): Phosphorylation of IGF-1R in NIH3T3-IGF-1R cell transfectants

NIH3T3 cells over-expressing the human IGF-1 receptor (NIH3T3-IGF-1R) were cultured for 24 h ours in growth medium, starved for 18 hours in serum-free medium and were stimulated for 10 min at 37° C. with equimolar concentrations of the indicated peptides. IGF-1R phosphorylation levels were analyzed by ELISA. Receptor phosphorylation is expressed as % of control±standard deviations (SD) (NIH 3T3 mouse embryonic fibroblast cells come from a cell line isolated and initiated in 1962 at the New York University School of Medicine Department of Pathology; Todaro G J, Green H. Quantitative studies of the growth of mouse embryo cells in culture and their development into established lines. J. Cell Biol. 17: 299-313, 1963)

Figure 3:
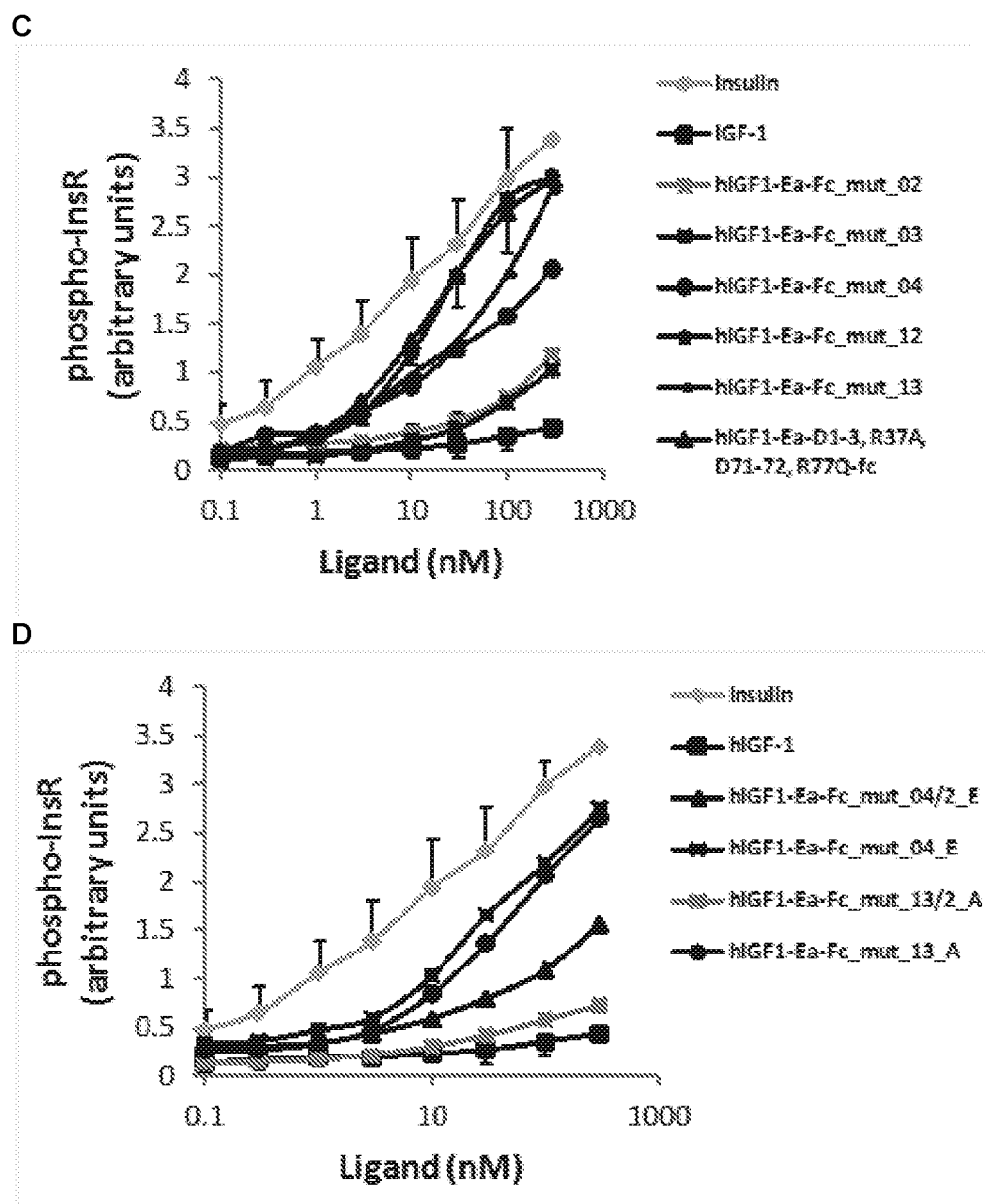

FIG. 3 (A-D): Phosphorylation of InsR in NIH3T3-InsR cell transfectants

NIH3T3 cells over-expressing the human insulin receptor (NIH3T3-InsR) were cultured for 24 h ours in growth medium, starved for 18 hours in serum-free medium and stimulated for 10 min at 37° C. with equimolar concentrations of the indicated peptides. InsR phosphorylation levels were analyzed by ELISA. Receptor phosphorylation is expressed as arbitrary units±standard deviations (SD).

FIG. 4 (A-C): Phosphorylation of IGF-1R in human and cynomolgus primary myoblasts Cells were cultured in growth medium, starved for 4 hours and then stimulated with hIGF-1 or hIGF-1 variants for 15 min at 37° C. IGF-1R phosphorylation levels were analyzed by ELISA using Duo-Set IC human phosphor-IGF1R. Receptor phosphorylation is expressed as % of control±standard deviations (SD).

FIG. 5 (A-D): Glucose uptake in mouse myotubes and adipocytes

3T3-L1 adipocytes (B and D) and C2C12 mouse myotubes (A and C) cell were seeded onto 24-well plates and cultured in serum-free DMEM for 4 hours. Serum-free DMEM was then replaced with KRP buffer or HBS for 3T3-L1 adipocytes and C2C12, respectively. Cells were treated for 1 hour with the specified peptides at 37° C. Glucose uptake was measured by adding 0.4 (adipocytes) or 0.8 (C2C12) µCi of [$^3$H] 2-deoxy-D-glucose and 0.1 (adipocytes) or 0.01 (C2C12) mM 2-deoxy-D-glucose for 10 (adipocytes) or 5 (C2C12) minutes at room temperature. Radioactivity was analyzed by scintillation counting.

Figure 6:
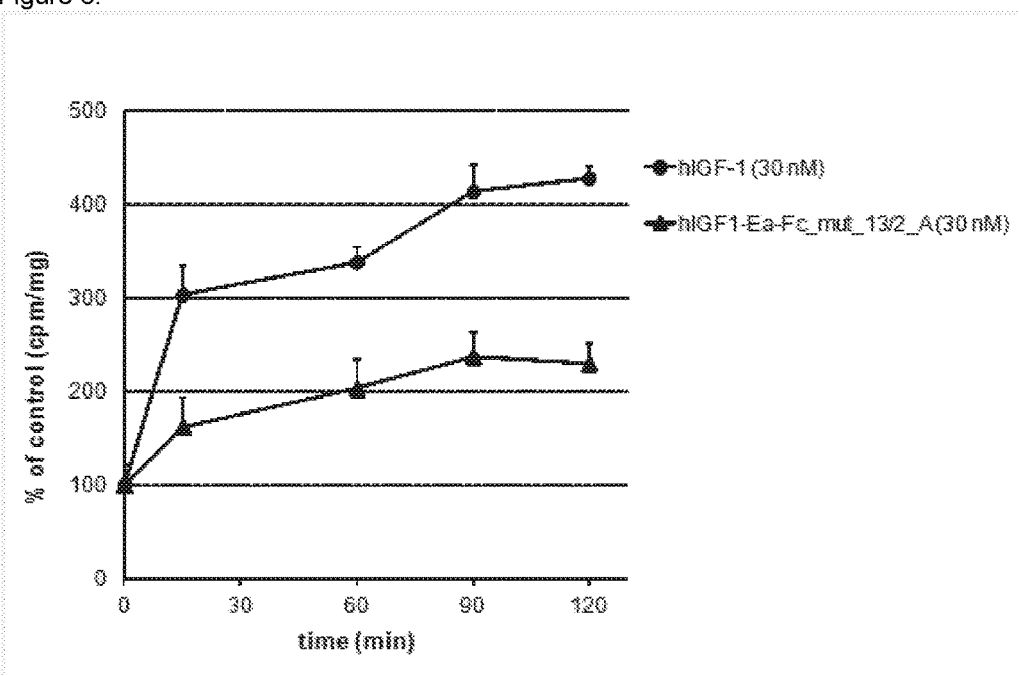

FIG. 6: Glucose uptake: time course in adipocytes

3T3-L1 adipocytes were seeded onto 24-well plates and cultured in serum-free DMEM (Dulbecco's Modified Eagle's Medium) for 4 hours. Serum-free DMEM was then replaced with KRP buffer and cells were treated for 15, 60, 90 and 120 minutes with the specified peptides at 37° C. Glucose uptake was measured by adding 0.4 µCi of [3H] 2-deoxy-D-glucose and 0.1 mM 2-deoxy-D-glucose for 10 minutes at room temperature. Radioactivity was analyzed by scintillation counting. 3T3-L1 is a cell line derived from 3T3 cells that is used in biological research on adipose tissue; Green H, Kehinde O (1975). "An established preadipose cell line and its differentiation in culture. II. Factors affecting the adipose conversion". Cell 5 (1): 1927.

Figure 7A:
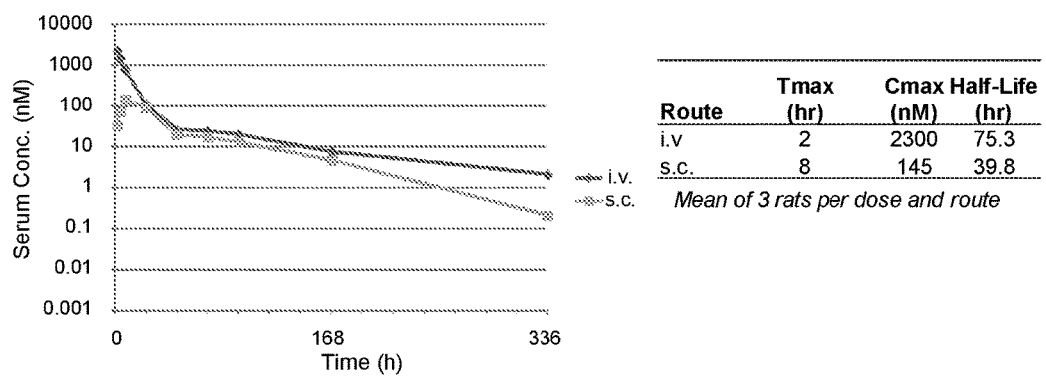
Figure 7B:
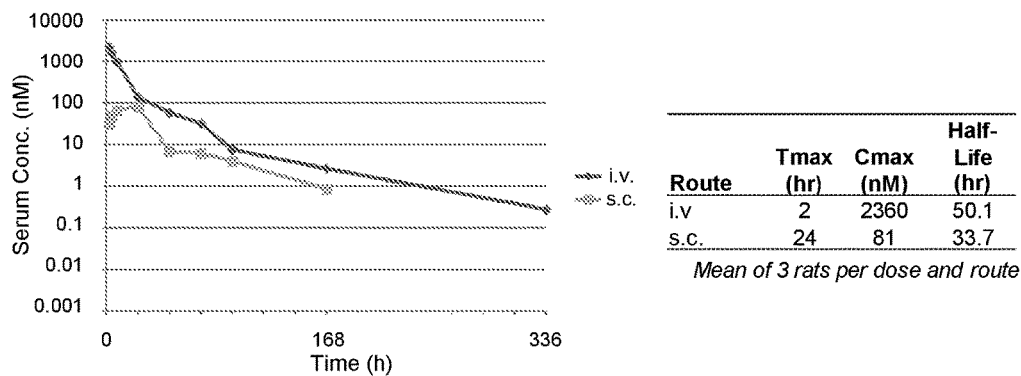
Figure 7C:
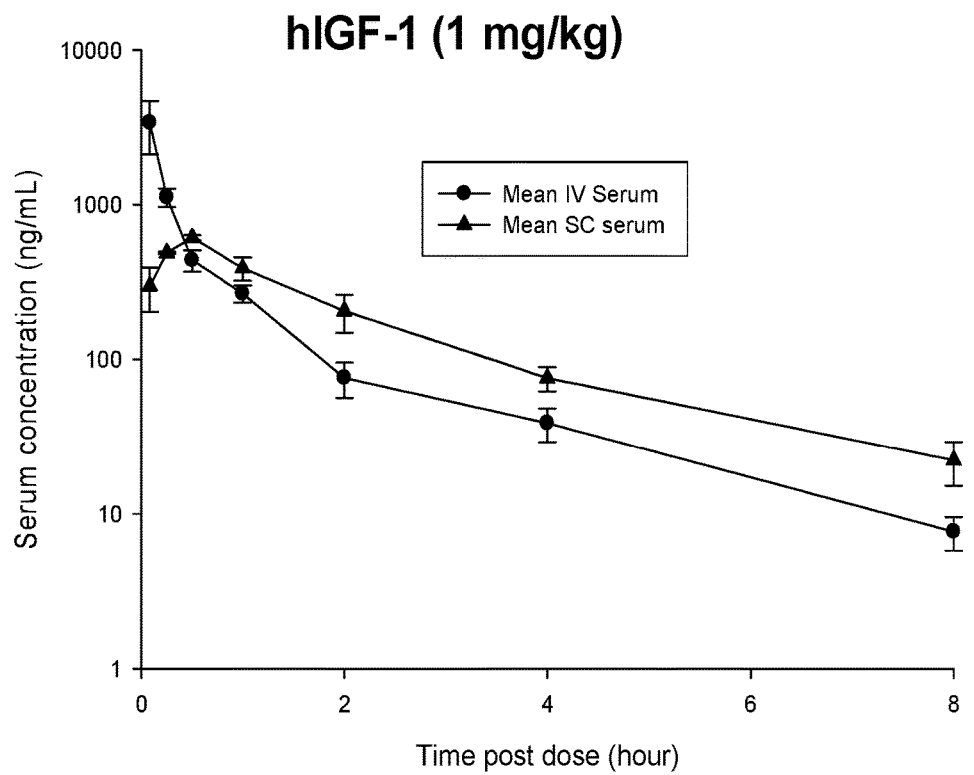

FIG. 7 (A-C):

Adult male rats (n=3/group) received an intravenous (i.v.) bolus or subcutaneous (s.c.) injection of hIGF-1-Ea-Fc_mut 13/2_A (FIG. 7A) or hIGF-1-Ea-Fc_mut 04/2 E (FIG. 7B) at 10 mg/kg or of hIGF-1 (FIG. 7C) at 1 mg/kg. Serial blood specimens were collected at 2, 4, 8, 24, 48, 72, 96, 168 and 336 hours after administration of test material. Serum concentrations of recombinant proteins were determined by ELISA.

Figure 8A:
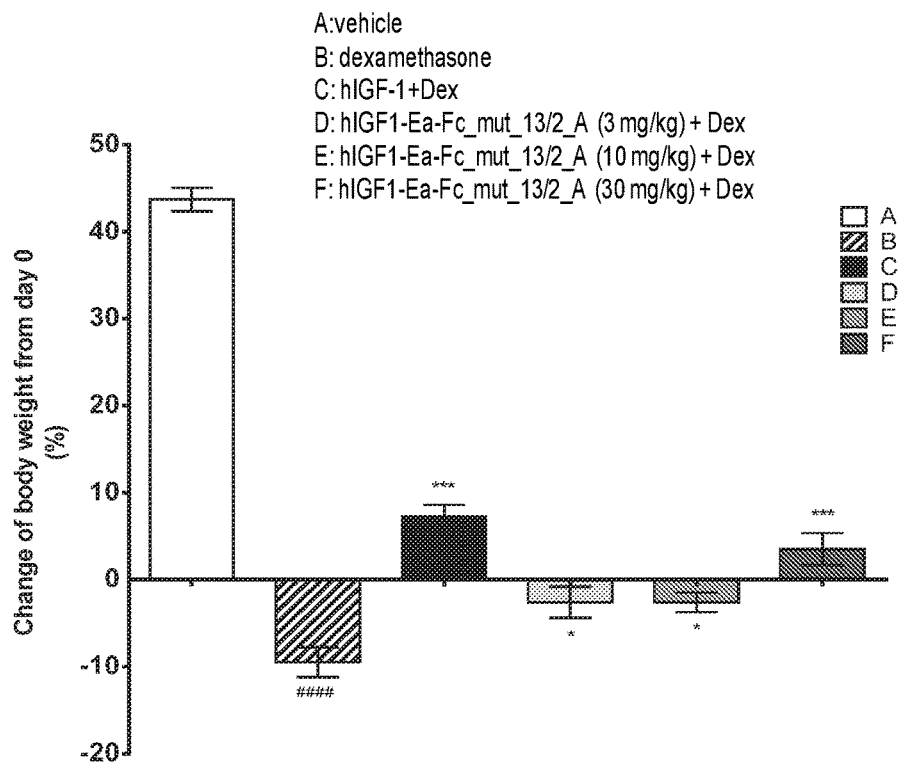
Figure 8B:
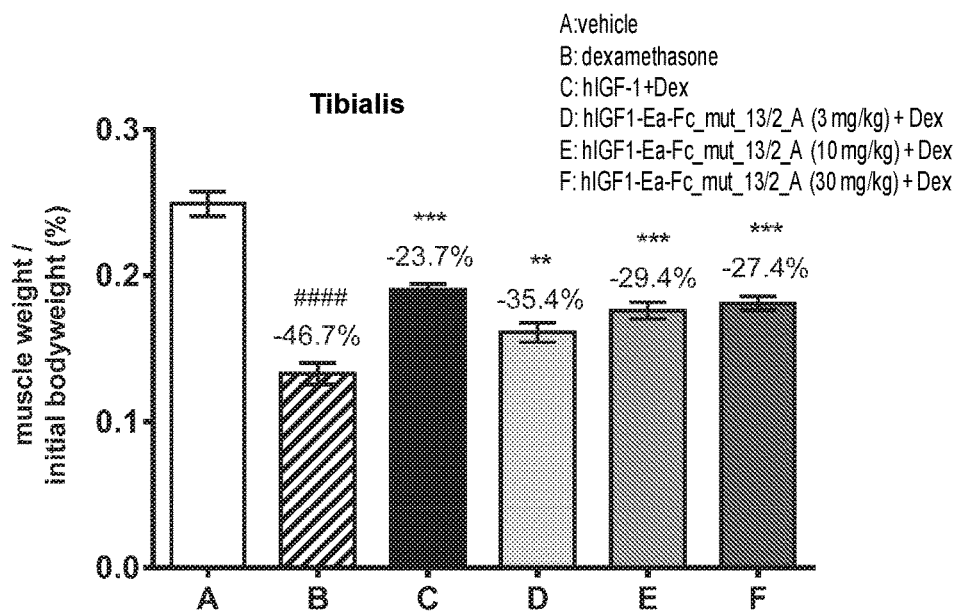
Figure 8C:
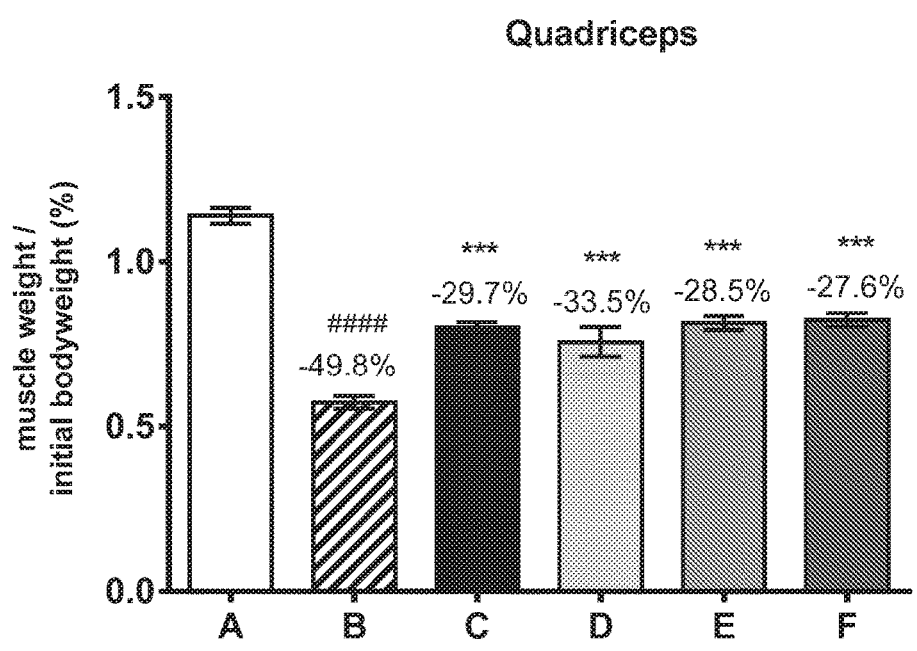

FIG. 8 (A-C): Effects of hIGF-1-Ea-Fc_mutants against dexamethasone-induced muscular atrophy.

Body (A), and muscle (B and C) weight changes of groups (A) vehicle, (B) Dex, (C) Dex with hIGF-1 at 3.8 mg/kg/day s.c. minipump infusion, (D) Dex with hIGF-1-Ea-Fc_mut_13/2_A at 3 mg/kg/day s.c. eod, (E) Dex with hIGF-1-Ea-Fc_mut_13/2_A at 10 mg/kg/day s.c. eod, and (F) Dex with hIGF-1-Ea-Fc_mut_13/2_A at 3 mg/kg/day s.c. eod Values are expressed as means±SEM (n=4-6). *: $P<0.05$, : $P<0.01$, : $P<0.001$ versus group B, #### $P<0.001$ versus group A (Dunnett's multiple comparison test following ANOVA).

FIG. 9: Production of IGF-1 variants with different G42 mutations in HEK293 cells Production data from 100 ml scale HEK293F culture transfected with FuGene. Titers were measured by analytical protein A HPLC from the cleared cell culture supernatants. Concentrations were measured after protein A purification. Aggregation levels of purified proteins were measured by SEC-MALS.

Figure 10:
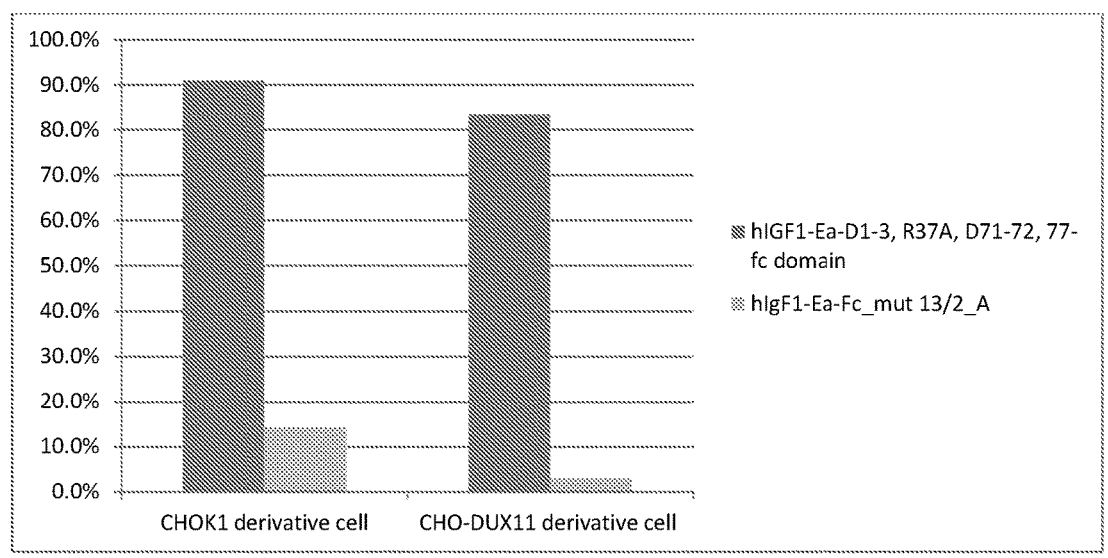

FIG. 10: Proportion of clipped material of hIGF1-Ea-D1-3, R37A, D71-72, 77-fc (SEQ ID NO. 6) (dark grey) and hIGF1-Ea-hFc_mut13/2_A (SEQ ID NO.9) (light grey) expressed from two different CHO cell lines. The proportion of clipped material was determined from purified protein (protein A chromatography) of transfected CHOK1 derivate cells as well as CHO-DUX11 derivate cells. The proportion of clipping was determined via reverse phase LC-MS analysis. The proportion of clipped material is significant lower for hIGF1-Ea-hFc_mut13/2_A in both cell lines.

Figure 11A:
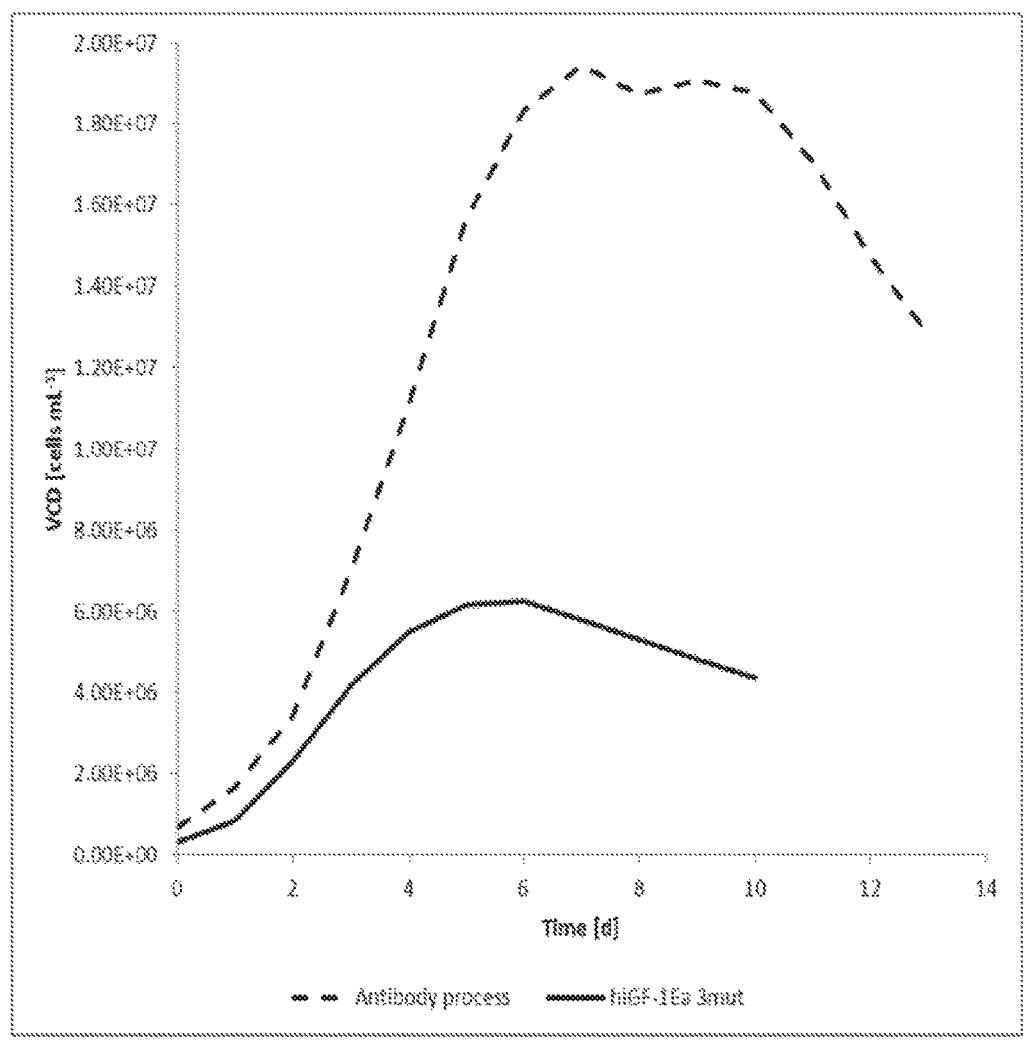
Figure 11B:
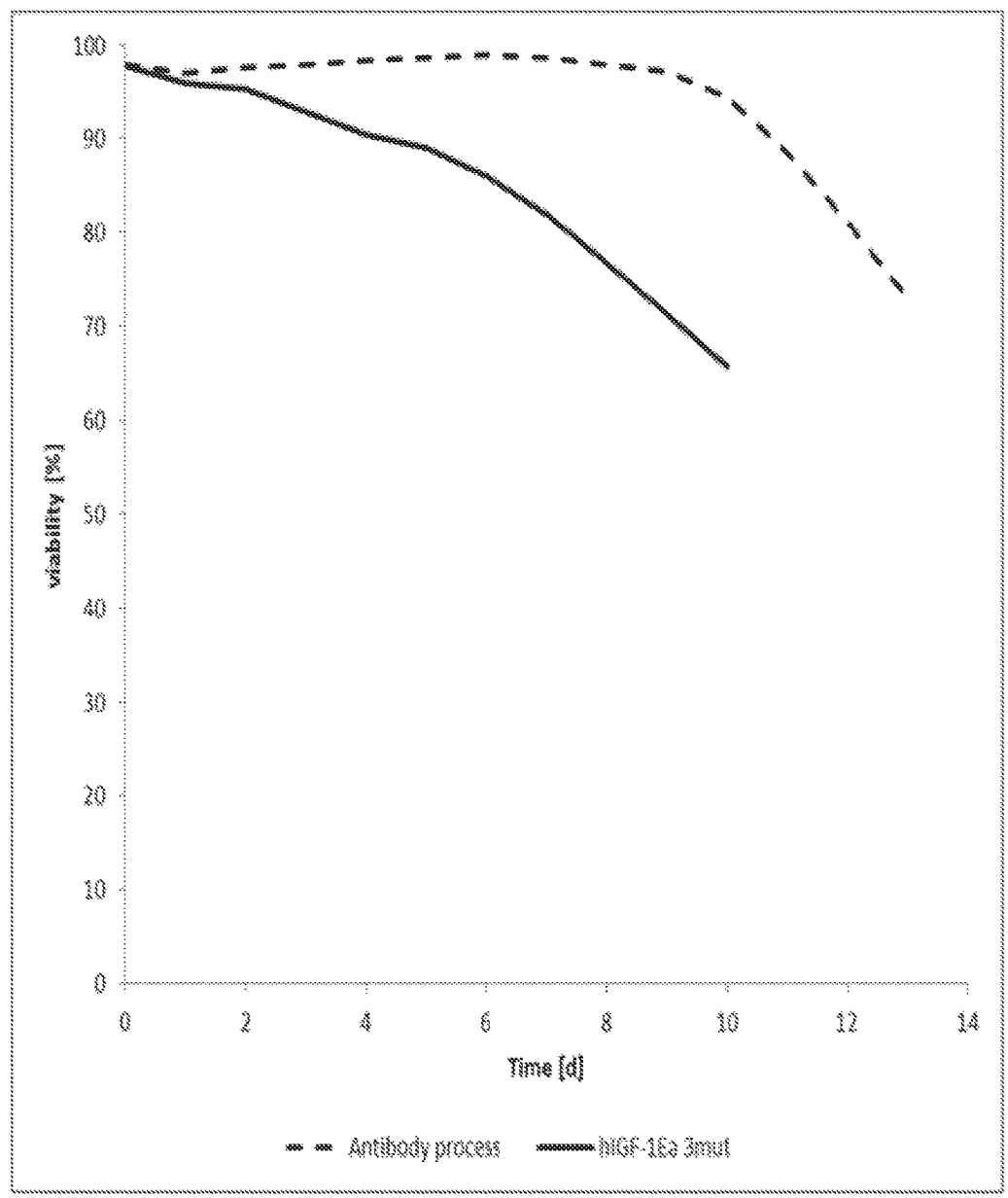

FIG. 11(A-B): Cell growth (FIG. 11A) of CHO-K1 derivative cells expressing a recombinant antibody (bold line) and CHO-K1 derivative cells expressing hIGF-1Ea 3mut (SEQ ID NO.: 27) (dotted line) in bioreactor runs. Percentage of viable cells (FIG. 11B) in bioreactor runs (bold line antibody producing CHO-K1 derivative clone, dotted line hIGF-1 Ea 3mut expressing clones).

Figure 12A:
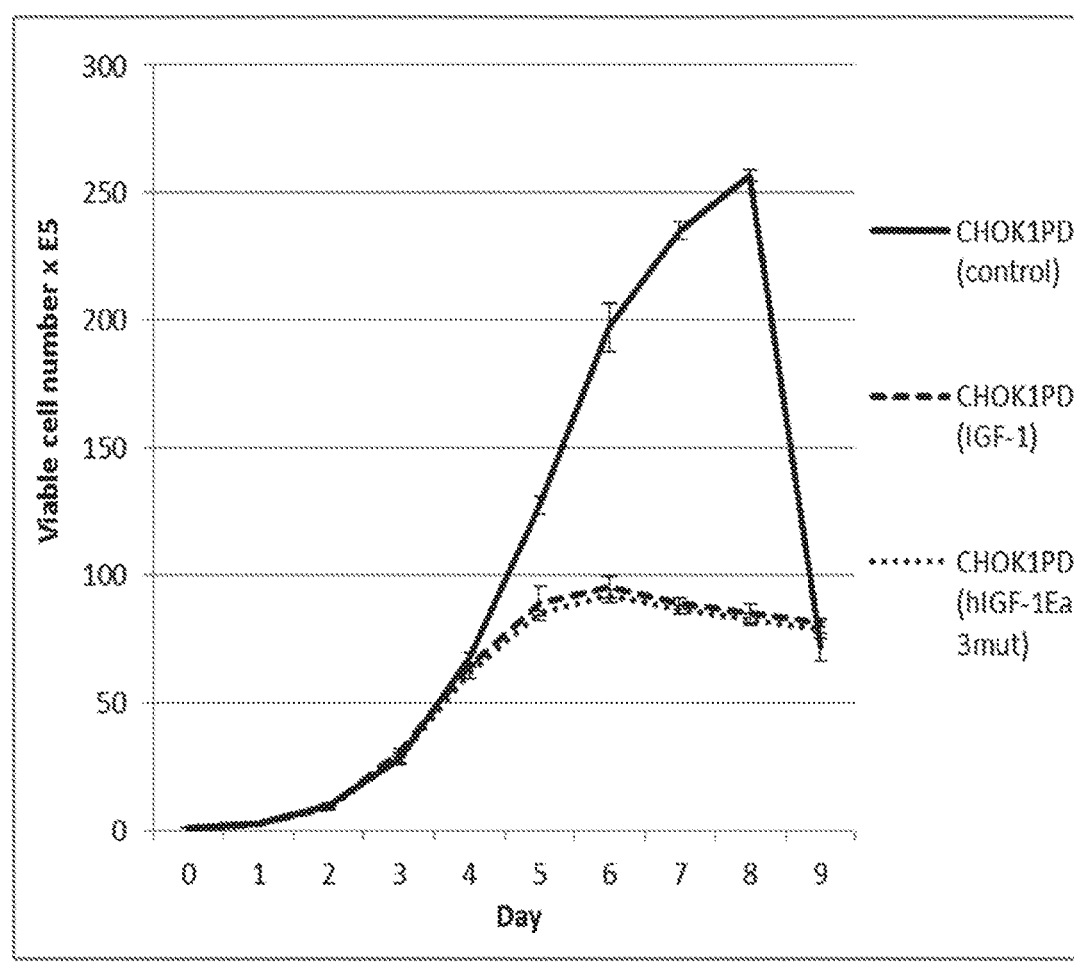
Figure 12B:
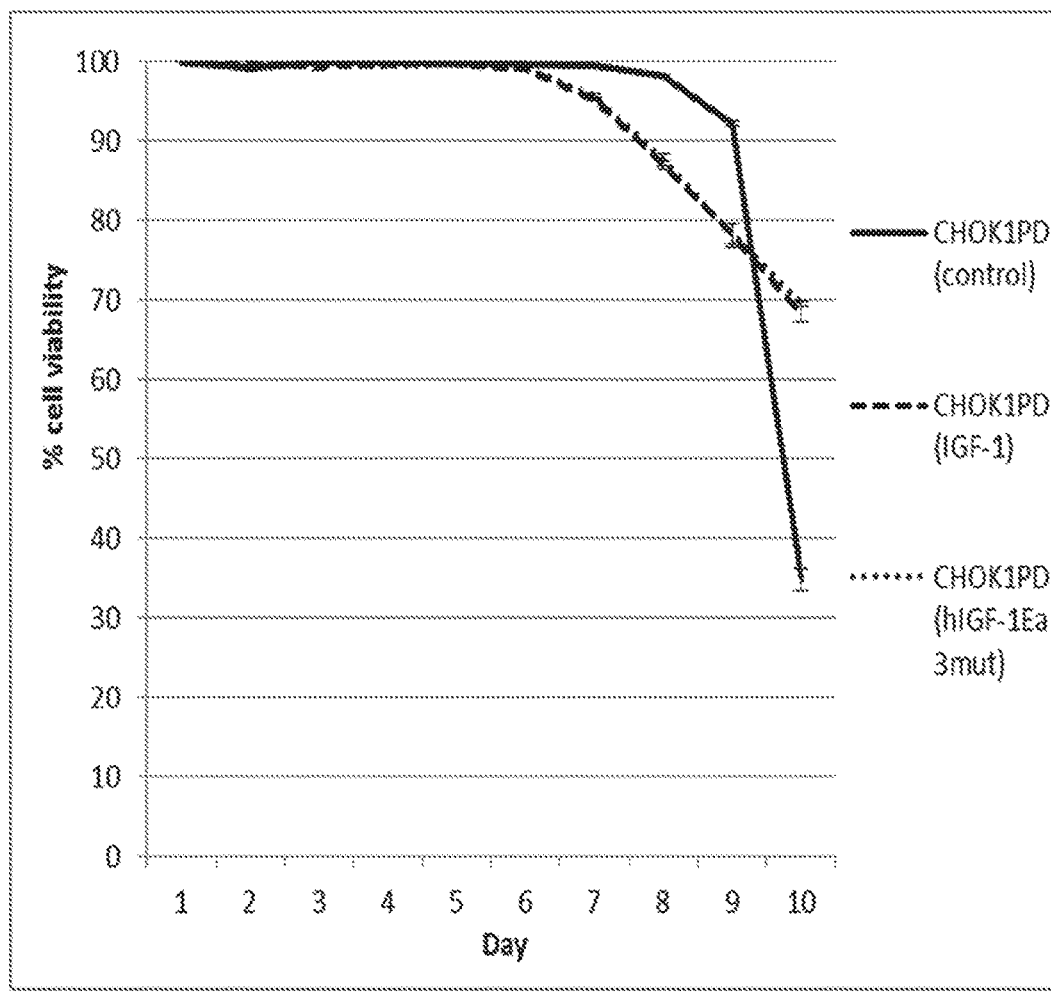

FIG. 12: Viable cell number (FIG. 12A): The continuous line shows the cell growth of CHO-K1 derivative cells. During co-cultivation with wildtype IGF-1 or hIGF-1Ea 3mut the cell growth is inhibited (dotted and dashed line, respectively). The average of 3 biologic replicates is shown. IGF-1/hIGF-1Ea 3mut was spiked on day 2 (spike-in experiment). Cell viability (FIG. 12B): The continuous line shows the cell viability of CHO-K1 derivative cell, the dotted respectively dashed line the reduced cell viability after IGF-1/hIGF-1Ea 3mut spike in. The cell viability drops two days earlier if the cells were co-incubated with IGF-1/hIGF-1 Ea 3mut. No difference between IGF-1 and hIGF-1 Ea 3mut in cell growth or cell viability could be detected.

Figure 13:
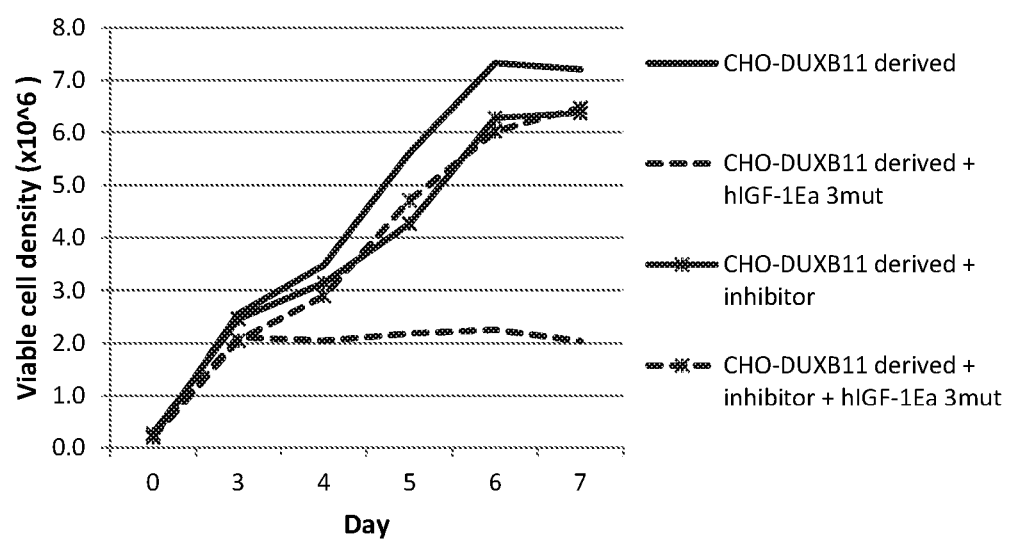

FIG. 13: Cell growth of CHO-DUXB11 derivative cells (bold line) and the reduced cell growth during co-cultivation with IGF-1 Ea 3mut (dotted lines) are shown. After adding the IGF-1R tyrosine kinase inhibitor NVPAEW541 (bold line with asterisk) the cell growth is slightly reduced. Co-cultivation with IGF-1Ea 3mut and adding the IGF-1R tyrosine kinase inhibitor resulted in no further cell growth inhibition (dotted line with asterisk).

Figure 14:
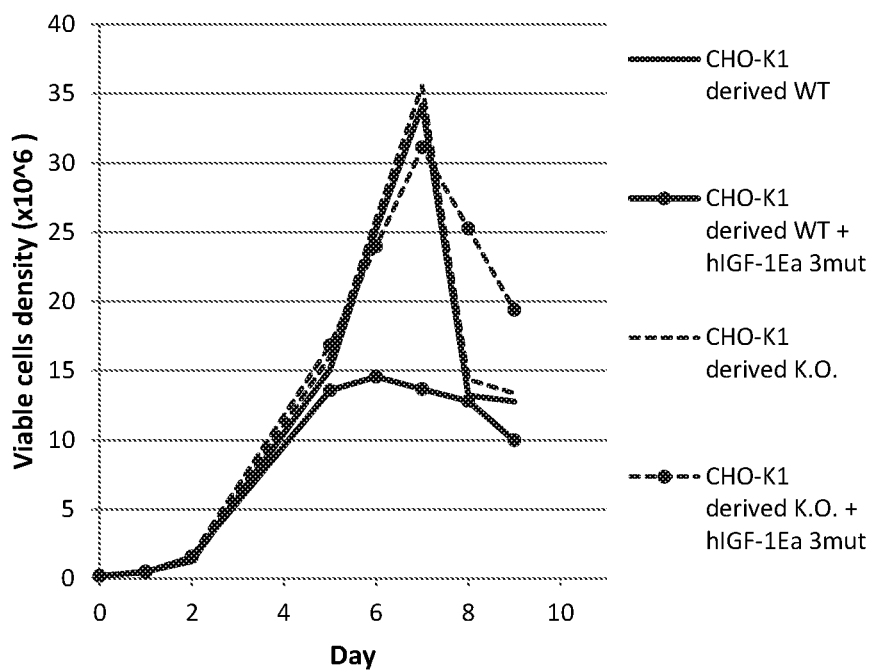

FIG. 14: In bold the cell growth of wildtype (WT) CHO-K1 derivative cells and in bold with circles the reduced cell growth during co-cultivation with IGF-1 is shown. With dotted lines the cell growth of the three IGF-1R KO clones are shown. The cell growth is slightly improved compared to the wildtype CHO-K1 derivative cells. The co-cultivation with IGF-1 resulted in only minor cell growth inhibition and cell growth is similar to wildtype CHO-K1 derivative cell without IGF-1 co-cultivation.

Figure 15:
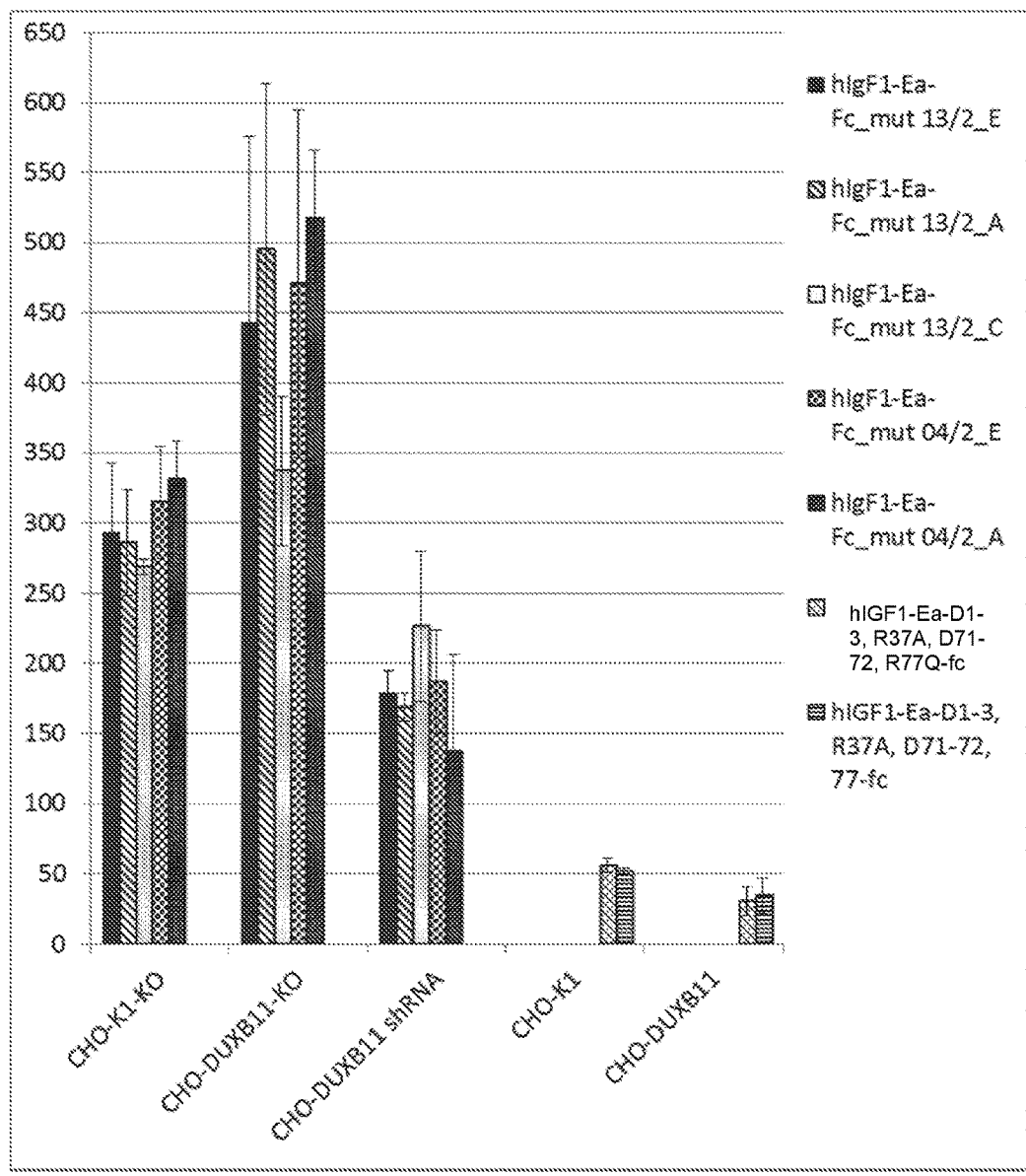

FIG. 15: IGF-1-Fc fusion protein titers of 14 day batch cultures are shown (pool level). The expressions of 7 different IGF-1-Fc fusion proteins in 5 different cell lines are highlighted. The expression of IGF-1-Fc fusion proteins was 5-20 fold increased in CHO-K1 derivative IGF-1R-KO cell lines, CHO-DUXB11 derivative IGF-1R-KO cell lines as well as in CHO-DUXB11 derivative shRNA (reduced expression of IGF-1R and INSR) cell lines compared to the CHO-K1 or CHO-DUXB11 derivative wildtype cell lines.

Figure 16:
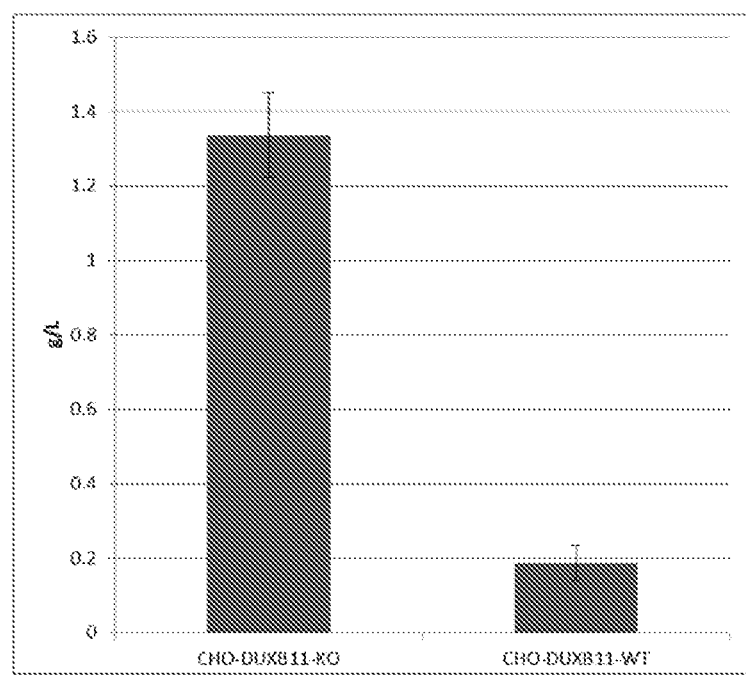

FIG. 16: IGF-1-Fc fusion titers of 14 day batch cultures in 50 ml shake flasks. The titers of the IGF-1-Fc fusion protein: hIGF-1-Ea-fc_mut 13/2_A in 15 best CHO-DUXB11 derivative IGF-1R-KO clones is ca. 6-7 fold higher compared to the titer of the IGF-1-Fc fusion protein: hIGF-1-Ea-Δ1-3, R37A, Δ71-72, R77Q-fc domain in CHO-DUXB11 derivative wildtype cell clones.

FIG. 17: Production and protein challenge of IGF-1 variants in HEK293F cells.

Production data from 100 ml scale HEK293T culture transfected with PEI. Yield after protein A purification extrapolated to 1 L culture volume. Aggregation measured by SEC-MALS after protein A purification. Purified proteins were incubated with conditioned CHO media from CHOK1 derived cells for 5 days and CHODUXB11 derived cells for 20 days. Percentage of remaining full length protein is shown. Method described in Example 2.

FIG. 18: Phosphorylation of InsR in NIH3T3-InsR cell transfectants

NIH3T3 cells over-expressing the human insulin receptor (NIH3T3-InsR) were cultured for 24 hours in growth medium, starved for 18 hours in serum-free medium and stimulated for 10 min at 37° C. with equimolar concentrations of the indicated peptides. InsR phosphorylation levels were analyzed by ELISA. Receptor phosphorylation is expressed as arbitrary units±standard deviations (SD).

Figure 19:
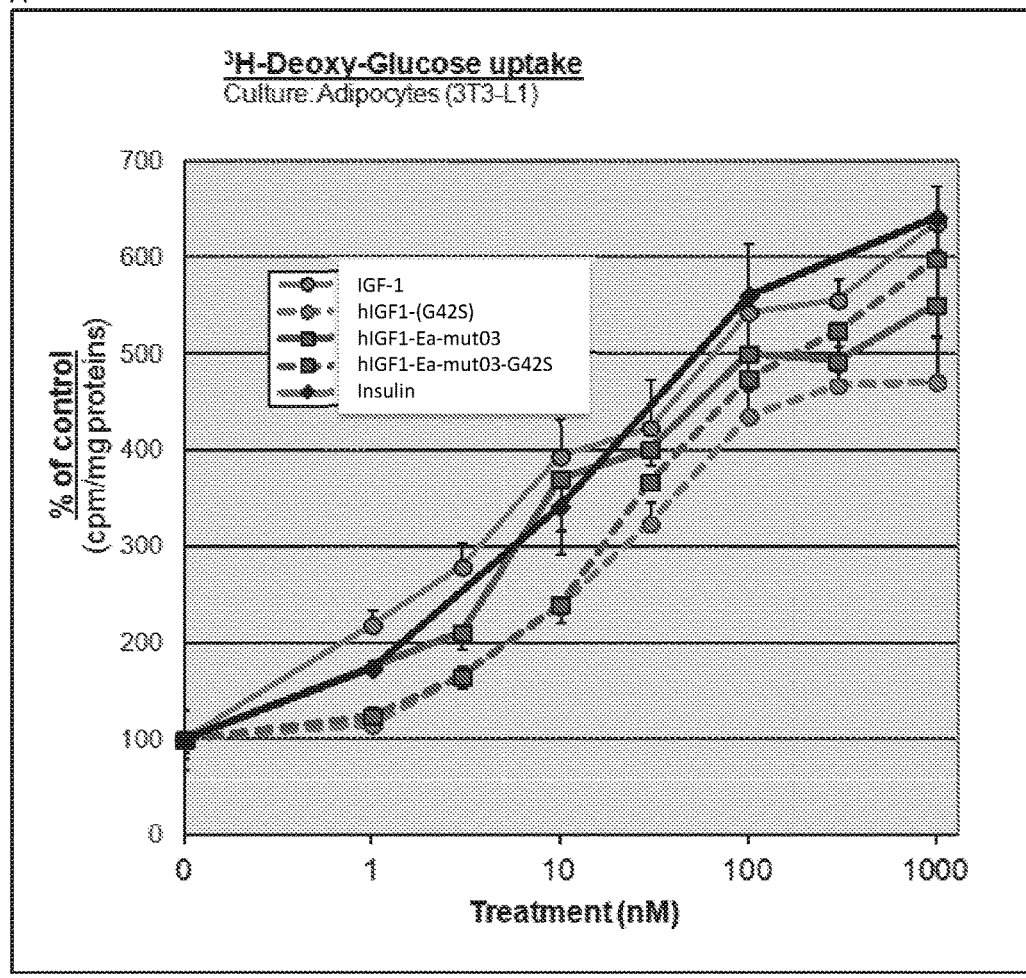
Figure 19:
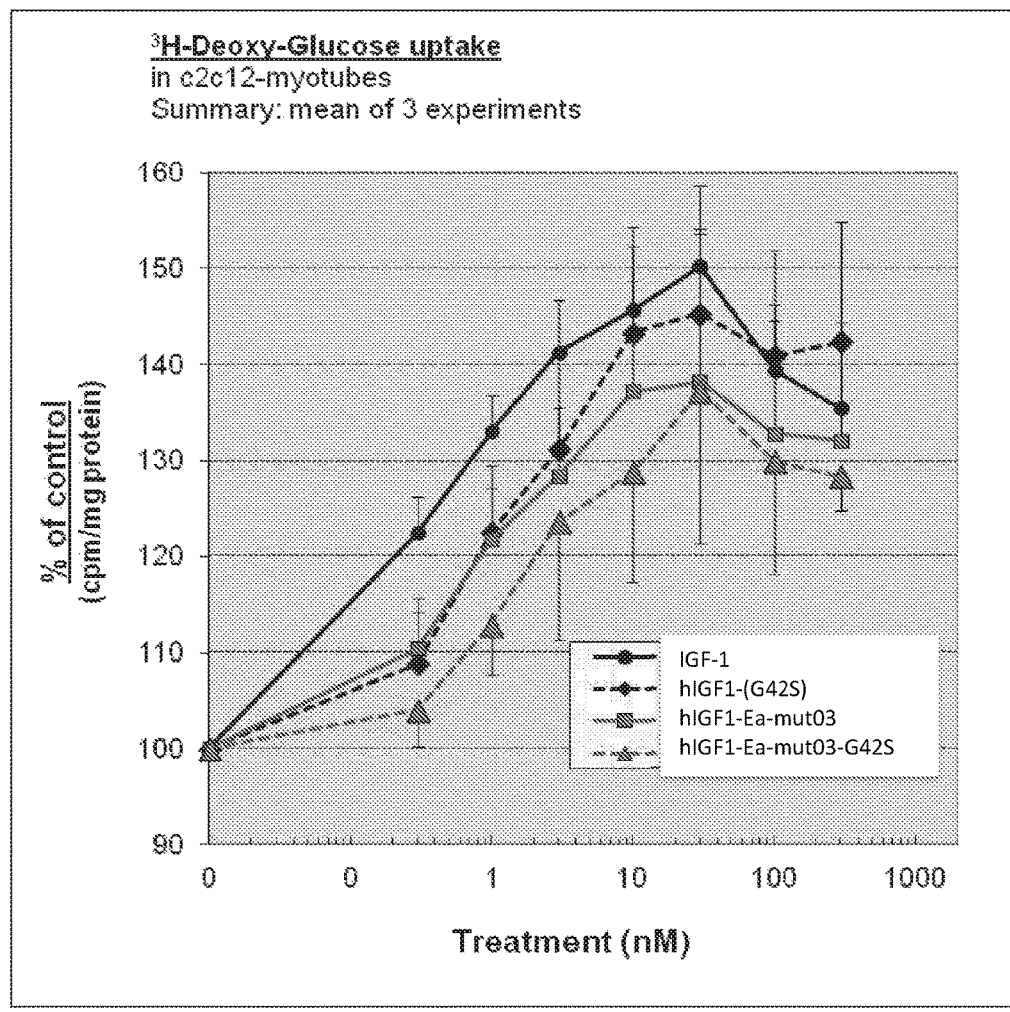

FIG. 19: Glucose uptake in mouse myotubes and adipocytes

3T3-L1 adipocytes (A) and C2C12 mouse myotubes (B) cell were seeded onto 24-well plates and cultured in serum-free DMEM for 4 hours. Serum-free DMEM was then replaced with KRP buffer or HBS for 3T3-L1 adipocytes and C2C12, respectively. Cells were treated for 1 hour with the specified peptides at 37° C. Glucose uptake was measured by adding 0.4 (adipocytes) or 0.8 (C2C12) µCi of [$^3$H] 2-deoxy-D-glucose and 0.1 (adipocytes) or 0.01 (C2C12) mM 2-deoxy-D-glucose for 10 (adipocytes) or 5 (C2C12) minutes at room temperature. Radioactivity was analyzed by scintillation counting.

GENERAL DEFINITIONS

In order that the present invention may be more readily understood, certain terms are first defined. Additional definitions are set forth throughout the detailed description.

Comprising: the term "comprising" means "including" e.g. a composition "comprising" X may consist exclusively of X or may include something additional e.g. X+Y.

The symbol "Δ" or the letters "d" or "D": in the context of a protein description (e.g. "hIGF-1-Ea-Δ1-3, R37A, Δ71-72, R77Q-fc domain" or "hIGF-1-Ea-D1-3, R37A, D71-72, R77Q-fc domain") refer to an amino acid deletion. As an example, the term "D71-72, 77" (in the context of the protein hIGF1-Ea-D1-3, R37A, D71-72, 77-fc) describes the fact that the amino acids 71, 72 and 77 have been deleted.

Insulin like growth factor 1 protein or a variant thereof: the phrase "Insulin like growth factor 1 protein or a variant thereof" refers to proteins being encoded by Insulin like growth factor 1 genes, particularly preferred is the human Insulin like growth factor 1 (hIGF-1) protein and variants thereof. An IGF-1 protein variant is a protein that differs by at least one amino acid from the IGF-1 wild-type sequence, wherein the term "wild-type sequence" refers to a polypeptide or gene sequence available in at least one naturally occurring organism or a polypeptide or gene sequence that has not been changed, mutated, or otherwise manipulated by man. The term IGF-1 variant and IGF-1 mimetic are used interchangeably throughout the document. An IGF-1 variant is also the IGF-1 precursor protein or the pro-IGF-1 protein comprising a peptide leader sequence. An IGF-1 variant is also a fusion protein comprising an IGF-1 protein, e.g. a protein comprising an IGF-1 protein fused to an immunoglobulin Fc region. Examples for IGF-1 variants are disclosed inter alia in the patent applications WO05033134 (stabilized IGF-1 protein fused to an immunoglobulin Fc region) and WO2007146689 (stabilized IGF-1 precursor proteins). An IGF-1 variant as described above retains its biological activity in the sense that such a protein can be considered as a functional equivalent of the wildtype IGF-1.

Functional equivalents with regard to the IGF-1 protein have to be understood as IGF-1 proteins comprising natural or artificial mutation. Mutations can be insertions, deletions or substitutions of one or more nucleic acids that do not diminish the biological activity of the IGF-1 protein. Functional equivalents having an identity of at least 80%, preferably 85%, more preferably 90%, most preferably more than 95%, very especially preferably at least 98% identity—but less than 100% identity to the IGF-1 wildtype protein, e.g. the human IGF-1 protein SEQ ID NO.: 1. In case of fusion proteins as described above, the 100% identity shall be defined only on the basis of the IGF-1 part of such a fusion protein.

Insulin like growth factors (IGFs) are part of a complex system that cells use to communicate with their physiologic environment. This complex system (often referred to as the insulin-like growth factor axis) consists of two cell-surface receptors (IGF-1R and IGF-2R), two ligands (IGF-1 and IGF-2), a family of six high-affinity IGF-binding proteins (IGFBP 1-6), and associated IGFBP degrading enzymes (proteases). This system is important not only for the regulation of normal physiology but also for a number of pathological states (Glass, Nat Cell Biol 5:87-90, 2003). The IGF axis has been shown to play roles in the promotion of cell proliferation and the inhibition of cell death (apoptosis). IGF-1 is mainly secreted by the liver as a result of stimulation by human growth hormone (hGH). Almost every cell in the human body is affected by IGF-1, especially cells in muscles, cartilage, bones, liver, kidney, nerves, skin and lungs. In addition to the insulin-like effects, IGF-1 can also regulate cell growth. IGF-1 and IGF-2 are regulated by a family of gene products known as the IGF-binding proteins. These proteins help to modulate IGF action in complex ways that involve both inhibiting IGF action by preventing binding to the IGF receptors as well as promoting IGF action through aiding delivery to the receptors and increasing IGF half-life in the blood stream. There are at least six characterized binding proteins (IGFBP1-6). IGF-1 is used in a wide range of therapeutic applications. Mecasermin (brand name Increlex™) is a synthetic analog of IGF-1 which is approved for the treatment of growth failure. Several companies have evaluated IGF-1 in clinical trials for a variety of additional indications, including type 1 diabetes, type 2-diabetes, amyotrophic lateral sclerosis, severe burn injury and myotonic muscular dystrophy. For the sake of clarity and consistency, the numbering of amino acid residues in IGF-1 precursor or mature proteins throughout this application and in the claims is based on the wild-type precursor protein sequence numbering of the human insulin-like growth factor 1 (somatomedin C), isoform CRA_c (accession no. EAW97697) without signal peptide (i.e. SEQ ID NO.: 5).

Mammalian cell: the term "mammalian cell" in the context of the disclosed method refers to mammalian cells which are suitable for protein production at industrial manufacturing scale. Those cells are well known to the skilled person and have originated for example from *Cricetulus griseus*, *Cercopithecus aethiops*, *Homo sapiens*, *Mesocricetus auratus*, *Mus musculus* and *Chlorocebus* species. The respective cell lines are known as CHO-cells (Chinese Hamster Ovary), COS-cells (a cell line derived from monkey kidney (African green monkey), Vero-cells (kidney epithelial cells extracted from African green monkey), Hela-cells (The line was derived from cervical cancer cells taken from Henrietta Lacks), BHK-cells (baby hamster kidney cells, HEK-cells (Human Embryonic Kidney), NS0-cells (Murine myeloma cell line), C127-cells (nontumorigenic mouse cell line), PerC6®-cells (human cell line, Crucell), CAP-cells (CEVEC's Amniocyte Production) and Sp-2/0-cells (Mouse myeloma cells).

The term "receptor specificity of stabilised IGF-1 prior art proteins" in the context of this application refers also to the reduced ability to induce insulin receptor phosphorylation (decreased potency and/or efficacy) of the IGF-1 molecules of the inventions compared to the prior art IGF-1 variants, which reduces the risk of inducing hypoglycemia, an adverse event of therapeutic concern.

Precursor: In the following, the term "precursor" when used in the context of the present invention shall refer to the precursor of the mature human IGF-1 protein without signal peptide, but including the Ea, Eb and Ec peptide, respectively.

DETAILED DESCRIPTION OF THE INVENTION

Molecules comprising an Ea-peptide fused to an immunoglobulin Fc region, wherein the protein residues G1, P2, E3, R71 and S72 have been deleted, the amino acid R77 has been deleted or substituted by glutamine and the R37 amino acid has been substituted by alanine (hIGF1-Ea-del1-3, R37A, del71-72, 77-fc domain (SEQ ID NO.:6) and hIGF1-Ea-del1-3, R37A, del71-72, R77Q-fc domain (SEQ ID NO.:7)) have been produced and tested. Expression of a hIGF1-Ea-del1-3, R37A, del71-72del71-72, 77-fc domain (SEQ ID NO.:6) in a mammalian cell system was not possible, because of aggregation and degradation issues (more than 90% of the produced protein was degraded; see FIG. 10) Furthermore, the hIGF1-Ea-del1-3, R37A, del71-72del71-72, 77-fc domain (SEQ ID NO.:6) proteins showed a decrease in receptor specificity compared to the unmodified mature IGF-1 in an NIH3T3 InsR phosphorylation assay (see FIG. 3).

Hence, the IGF-1 precursor variants fused to a human immunoglobulin Fc region are poor drug candidates, because (i) low production yield in mammalian production system, and (ii) increased binding affinity to the insulin receptor (InsR) compared to the unmodified human wildtype IGF-1, which can result in hypoglycemia, an adverse event of therapeutic concern. The invention is based on the surprising observation that (1) production yield in mammalian cell production systems and (2) the receptor specificity of native IGF-1 proteins or stabilised IGF-1 prior art proteins can be improved by introducing additional specific amino acid mutations, wherein different mutations solve different problems and said mutations can be combined to address multiple issues related to production yield, efficacy and/or receptor specificity.

A particular surprising result was the observation that human IGF-1 protein (SEQ ID NO.: 1) being mutated at position G42 (G42S substitutions) induce lower glucose uptake in C2C12 myotube and adipocyte (3T3-L1) in vitro systems compared to the unmodified human wildtype IGF-1, which might reduce the hypoglycemia risk of in vivo IGF-1 treatment (FIG. 18).

A furthermore particular surprising result was the observation that human IGF-1 precursor prior art proteins being mutated at position G42 (deletion or specific substitutions) show a similar ability to stimulate insulin receptor (InsR) phosphorylation as the unmodified human wildtype IGF-1, which diminishes the hypoglycemia risk of the prior art IGF-1 variants (FIG. 3). Even more surprising was the observation that the G42S mutation has an additional positive impact on the production yield of human IGF-1 precursor prior art proteins being fused to an immunoglobulin Fc region in mammalian cell (FIG. 10/17), i.e. the formation of aggregates negatively impacting production yield could be dramatically reduced by introducing a G42S mutation (FIG. 9/17). Consequently, the invention is to some extend based on the surprising finding, that by manipulating the amino acid glycine 42 in human IGF-1 protein or human IGF-1 precursor variants thereof, two major technical hurdles in the development of therapeutic IGF-1 variants could have been overcome. In another aspect the invention provides a solution for the problem that prior art IGF-1 precursor proteins being fused to a immunoglobulin Fc region of a human IgG cannot be produced at industrial scale in mammalian cells, because said fusion proteins are readily being degraded by mammalian cell proteases. Consequently, in another aspect the invention is based on the surprising finding that by manipulating specific amino acids in IGF-1 Ea-peptide precursor variants an additional major technical hurdle in the development of therapeutic IGF-1 precursor variants could have been overcome.

Examples of such molecules include, but are not limited to, the following polypeptides:

A human IGF-1 protein (SEQ ID No.: 1) wherein the amino acid G42 is deleted.

A human IGF-1 protein (SEQ ID No.: 1) wherein the amino acid G42 is substituted by the amino acid serine.

A human IGF-1 protein (SEQ ID No.: 1) wherein the amino acid G42 is substituted by the amino acid serine and wherein the amino acid(s)

(a) G1, P2, E3 are deleted and amino acid R36 is substituted or deleted; or
(b) G1, P2, E3 are deleted and amino acid R36 is substituted by glutamine (Q); or
(c) G1, P2, E3 are deleted and amino acid R37 is substituted or deleted; or
(d) G1, P2, E3 are deleted and amino acid R37 is substituted by glutamic acid (E); or
(e) G1, P2, E3 are deleted and amino acid R37 is substituted by alanine; or
(f) G1, P2, E3 are deleted and amino acid R37 is substituted by proline (P); or
(g) G1, P2, E3 are deleted and amino acids R36 and R37 are substituted or deleted; or
(h) G1, P2, E3 are deleted and amino acid R36 and R37 are both substituted by glutamine (Q); or
(i) G1, P2, E3 are deleted, amino acid R36 is substituted by glutamine (Q) and R37 is substituted by alanine.

A human IGF-1 protein (SEQ ID No.: 1) wherein the amino acid G42 is substituted by the amino acid serine and wherein the amino acid E3 is deleted and amino acid R37 is substituted by alanine.

A human IGF-1 protein (SEQ ID No.: 1) wherein the amino acid G42 is substituted by the amino acid serine and wherein the amino acid E3 is deleted and amino acid R37 is substituted by alanine fused to an immunoglobulin Fc region, particularly a modified Fc region, particularly an Fc region, which is modified to modulate its binding to the Fc receptor, as described below.

Another polypeptide of the invention is the human IGF-1 protein of SEQ ID NO.: 117.

Another polypeptide of the invention is the human IGF-1 precursor protein of SEQ ID NO.: 118.

It has been discovered that the mutation or deletion of amino acids R74, R77, G96, S97, A98, G99, N100, K101, N102, Y103, Q104 and/or M105 of the prior art IGF-1 Ea peptide precursor proteins mentioned above leads to a higher yield of non-degraded protein when expressed by mammalian cells. Is has furthermore been discovered that combination of the mentioned mutations/deletions at positions R74, R77, G96, S97, A98, G99, N100, K101, N102, Y103, Q104 and/or M105 results in a synergistic effect. Therefore, in one embodiment R74, R77, G96, S97, A98, G99, N100, K101, N102, Y103, Q104 and/or M105, provided that the modified IGF-1 protein comprises the Ea-peptide (SEQ ID NO.: 2), is deleted or mutated in the herein disclosed modified IGF-1 precursor proteins. In one embodiment, R74, R77 and/or R104 are mutated to Q in the herein disclosed IGF-1 precursor proteins. In a further embodiment, K68, S69, A70, R71 and/or R72 may additionally be deleted or mutated in the herein disclosed modified IGF-1 precursor proteins.

Accordingly, the invention provides a polypeptide containing a human IGF-1 precursor protein, i.e. comprising the Ea-peptide from human IGF-1, wherein the amino acid glycine at position 42 is deleted or substituted by another amino acid and wherein the numbering of the amino acids corresponds to SEQ ID NO.: 5. The E-peptide may be the Ea, Eb, or Ec peptide (SEQ ID NOs: 2-4). In a particular embodiment, the amino acid glycine at position 42 is deleted or substituted by the amino acid or serine.

In one embodiment, the above described human IGF-1 Ea-peptide precursor protein being mutated at position G42 as described above (deleted or mutated to serine) comprises additional deletions and/or mutations at amino acids G1, P2, E3, R36, R37, K68, S69, A70, R71, S72, R74, R77, G96, S97, A98, G99, N100, K101, N102, Y103, Q104 and/or M105, wherein the numbering of the amino acids corresponds to SEQ ID NO.: 5.

Examples of such molecules include, but are not limited to, the following polypeptides:

A polypeptide comprising a human IGF-1 Ea-peptide precursor protein wherein the amino acid G42 is substituted by the amino acid serine and wherein the amino acid(s)

(1) G1, P2, E3 are deleted, amino acid R36 is substituted or deleted and the amino acids R71 and S72 are deleted.
(2) G1, P2, E3 are deleted, amino acid R36 is substituted by glutamine (Q) and the amino acids R71 and S72 are deleted.
(3) G1, P2, E3 are deleted, amino acid R37 is substituted or deleted and the amino acids R71 and S72 are deleted.
(4) G1, P2, E3 are deleted, amino acid R37 is substituted by glutamic acid (E) and the amino acids R71 and S72 are deleted.
(5) G1, P2, E3 are deleted, amino acid R37 is substituted by alanine and the amino acids R71 and S72 are deleted.
(6) G1, P2, E3 are deleted, amino acid R37 is substituted by proline (P) and the amino acids R71 and S72 are deleted.
(7) G1, P2, E3 are deleted, amino acids R36 and R37 are substituted or deleted and the amino acids R71 and S72 are deleted.
(8) G1, P2, E3 are deleted, amino acid R36 and R37 are both substituted by glutamine (Q) and the amino acids R71 and S72 are deleted.
(9) G1, P2, E3 are deleted, amino acid R36 is substituted by glutamine (Q), R37 is substituted by alanine and the amino acids R71 and S72 are deleted.
(10) G1, P2, E3 are deleted, amino acid R36 is substituted or deleted and the amino acids R71 and S72 are deleted and amino acid R77 is mutated to glutamine (Q).
(11) G1, P2, E3 are deleted, amino acid R36 is substituted or deleted and the amino acids R71 and S72 are deleted and amino acids R74 and R77 are mutated to glutamine (Q).
(12) G1, P2, E3 are deleted, amino acid R36 is substituted or deleted and the amino acids R71 and S72 are deleted and amino acids R74, R77 and Q104 are mutated to glutamine (Q).
(13) G1, P2, E3 are deleted, amino acid R36 is substituted by glutamine (Q) and the amino acids R71 and S72 are deleted and amino acid R74 is mutated to glutamine (Q).
(14) G1, P2, E3 are deleted, amino acid R36 is substituted by glutamine (Q) and the amino acids R71 and S72 are deleted and amino acids R74 and R77 are mutated to glutamine (Q).

(15) G1, P2, E3 are deleted, amino acid R36 is substituted by glutamine (Q) and the amino acids R71 and S72 are deleted and amino acids R74, R77 and R104 are mutated to glutamine (Q).
(16) G1, P2, E3 are deleted, amino acid R37 is substituted by glutamic acid (E) and the amino acids R71 and S72 are deleted and amino acid R77 is mutated to glutamine (Q).
(17) G1, P2, E3 are deleted, amino acid R37 is substituted by glutamic acid (E) and the amino acids R71 and S72 are deleted and amino acids R74 and R77 are mutated to glutamine (Q).
(18) G1, P2, E3 are deleted, amino acid R37 is substituted by glutamic acid (E) and the amino acids R71 and S72 are deleted and amino acids R74, R77 and R104 are mutated to glutamine (Q).
(19) G1, P2, E3 are deleted, amino acid R37 is substituted by alanine (A) and the amino acids R71 and S72 are deleted and amino acid R74 is mutated to glutamine (Q).
(20) G1, P2, E3 are deleted, amino acid R37 is substituted by alanine (A) and the amino acids R71 and S72 are deleted and amino acids R74 and R77 are mutated to glutamine (Q).
(21) G1, P2, E3 are deleted, amino acid R37 is substituted by alanine (A) and the amino acids R71 and S72 are deleted and amino acids R74, R77 and R104 are mutated to glutamine
(22) G1, P2, E3 are deleted, amino acid R37 is substituted by proline (P) and the amino acids R71 and S72 are deleted and amino acid R74 is mutated to glutamine (Q).
(23) G1, P2, E3 are deleted, amino acid R37 is substituted by proline (P) and the amino acids R71 and S72 are deleted and amino acids R74 and R77 are mutated to glutamine (Q).
(24) G1, P2, E3 are deleted, amino acid R37 is substituted by proline (P) and the amino acids R71 and S72 are deleted and amino acids R74, R77 and R104 are mutated to glutamine
(25) G1, P2, E3 are deleted, amino acid R36 and R37 are both substituted by glutamine (Q) and the amino acids R71 and S72 are deleted and amino acid R74 is mutated to glutamine (Q).
(26) G1, P2, E3 are deleted, amino acid R36 and R37 are both substituted by glutamine (Q) and the amino acids R71 and S72 are deleted and amino acids R74 and R77 are mutated to glutamine (Q).
(27) G1, P2, E3 are deleted, amino acid R36 is substituted by glutamine (Q), R37 is substituted by alanine and the amino acids R71 and S72 are deleted and amino acids R74 and R77 are mutated to glutamine (Q).
(28) G1, P2, E3 are deleted, amino acid R36 and R37 are both substituted by glutamine (Q) and the amino acids R71 and S72 are deleted and amino acids R74, R77 and R104 are mutated to glutamine (Q).
(29) G1, P2, E3 are deleted, amino acid R36 is substituted by glutamine (Q), R37 is substituted by alanine and the amino acids R71 and S72 are deleted and amino acids R74, R77 and R104 are mutated to glutamine (Q).
(1a) G1, P2, E3 are deleted, amino acid R36 is substituted or deleted and the amino acids K68, S69, A70, R71 and S72 are deleted.
(2a) G1, P2, E3 are deleted, amino acid R36 is substituted by glutamine (Q) and the amino acids K68, S69, A70, R71 and S72 are deleted.
(3a) G1, P2, E3 are deleted, amino acid R37 is substituted or deleted and the amino acids K68, S69, A70, R71 and S72 are deleted.
(4a) G1, P2, E3 are deleted, amino acid R37 is substituted by glutamic acid (E) and the amino acids K68, S69, A70, R71 and S72 are deleted.
(5a) G1, P2, E3 are deleted, amino acid R37 is substituted by alanine and the amino acids K68, S69, A70, R71 and S72 are deleted.
(6a) G1, P2, E3 are deleted, amino acid R37 is substituted by proline (P) and the amino acids K68, S69, A70, R71 and S72 are deleted.
(7a) G1, P2, E3 are deleted, amino acids R36 and R37 are substituted or deleted and the amino acids K68, S69, A70, R71 and S72 are deleted.
(8a) G1, P2, E3 are deleted, amino acid R36 and R37 are both substituted by glutamine (Q) and the amino acids K68, S69, A70, R71 and S72 are deleted.
(9a) G1, P2, E3 are deleted, amino acid R36 is substituted by glutamine (Q), R37 is substituted by alanine and the amino acids K68, S69, A70, R71 and S72 are deleted.
(10a) G1, P2, E3 are deleted, amino acid R36 is substituted or deleted and the amino acids K68, S69, A70, R71 and S72 are deleted and amino acid R74 is mutated to glutamine (Q).
(11a) G1, P2, E3 are deleted, amino acid R36 is substituted or deleted and the amino acids K68, S69, A70, R71 and S72 are deleted and amino acids R74 and R77 are mutated to glutamine (Q).
(12a) G1, P2, E3 are deleted, amino acid R36 is substituted or deleted and the amino acids K68, S69, A70, R71 and S72 are deleted and amino acids R74, R77 and Q104 are mutated to glutamine (Q).
(13a) G1, P2, E3 are deleted, amino acid R36 is substituted by glutamine (Q) and the amino acids K68, S69, A70, R71 and S72 are deleted and amino acid R74 is mutated to glutamine (Q).
(14a) G1, P2, E3 are deleted, amino acid R36 is substituted by glutamine (Q) and the amino acids K68, S69, A70, R71 and S72 are deleted and amino acids R74 and R77 are mutated to glutamine (Q).
(15a) G1, P2, E3 are deleted, amino acid R36 is substituted by glutamine (Q) and the amino acids K68, S69, A70, R71 and S72 are deleted and amino acids R74, R77 and R104 are mutated to glutamine (Q).
(16a) G1, P2, E3 are deleted, amino acid R37 is substituted by glutamic acid (E) and the amino acids K68, S69, A70, R71 and S72 are deleted and amino acid R74 is mutated to glutamine (Q).
(17a) G1, P2, E3 are deleted, amino acid R37 is substituted by glutamic acid (E) and the amino acids K68, S69, A70, R71 and S72 are deleted and amino acids R74 and R77 are mutated to glutamine (Q).
(18a) G1, P2, E3 are deleted, amino acid R37 is substituted by glutamic acid (E) and the amino acids K68, S69, A70, R71 and S72 are deleted and amino acids R74, R77 and R104 are mutated to glutamine (Q).
(19a) G1, P2, E3 are deleted, amino acid R37 is substituted by alanine (A) and the amino acids K68, S69, A70, R71 and S72 are deleted and amino acid R74 is mutated to glutamine (Q).
(20a) G1, P2, E3 are deleted, amino acid R37 is substituted by alanine (A) and the amino acids K68, S69, A70, R71 and S72 are deleted and amino acids R74 and R77 are mutated to glutamine (Q).
(21a) G1, P2, E3 are deleted, amino acid R37 is substituted by alanine (A) and the amino acids K68, S69, A70, R71 and S72 are deleted and amino acids R74, R77 and R104 are mutated to glutamine
(22a) G1, P2, E3 are deleted, amino acid R37 is substituted by proline (P) and the amino acids K68, S69, A70, R71 and S72 are deleted and amino acid R74 is mutated to glutamine (Q).

(23a) G1, P2, E3 are deleted, amino acid R37 is substituted by proline (P) and the amino acids K68, S69, A70, R71 and S72 72 are deleted and amino acids R74 and R77 are mutated to glutamine (Q).
(24a) G1, P2, E3 are deleted, amino acid R37 is substituted by proline (P) and the amino acids K68, S69, A70, R71 and S72 are deleted and amino acids R74, R77 and R104 are mutated to glutamine
(25a) G1, P2, E3 are deleted, amino acid R36 and R37 are both substituted by glutamine (Q) and the amino acids K68, S69, A70, R71 and S72 are deleted and amino acid R74 is mutated to glutamine (Q).
(26a) G1, P2, E3 are deleted, amino acid R36 and R37 are both substituted by glutamine (Q) and the amino acids K68, S69, A70, R71 and S72 are deleted and amino acids R74 and R77 are mutated to glutamine (Q).
(27a) G1, P2, E3 are deleted, amino acid R36 is substituted by glutamine (Q), R37 is substituted by alanine and the amino acids K68, S69, A70, R71 and S72 are deleted and amino acids R74 and R77 are mutated to glutamine (Q).
(28a) G1, P2, E3 are deleted, amino acid R36 and R37 are both substituted by glutamine (Q) and the amino acids K68, S69, A70, R71 and S72 are deleted and amino acids R74, R77 and R104 are mutated to glutamine (Q).
(29a) G1, P2, E3 are deleted, amino acid R36 is substituted by glutamine (Q), R37 is substituted by alanine and the amino acids K68, S69, A70, R71 and S72 are deleted and amino acids R74, R77 and R104 are mutated to glutamine (Q).

In another embodiment the disclosure relates to the above described proteins comprising the polypeptides (1)-(29a), wherein said molecules instead of being mutated at the positions 1-3, only the amino acid E3 is deleted (e.g. the molecule (28a) could also refer to a polypeptide comprising a human IGF-1 Ea-peptide precursor protein wherein the amino acid G42 is substituted by the amino acid serine and wherein the amino acid E3 is deleted, amino acid R36 and R37 are both substituted by glutamine (Q), the amino acids K68, S69, A70, R71 and S72 are deleted and amino acids R74, R77 and R104 are mutated to glutamine (Q).)

Additionally, the disclosure relates to a polypeptide containing a human IGF-1 precursor protein, i.e. comprising the Ea-peptide from human IGF-1, which is fused to an immunoglobulin Fc region and wherein the amino acid glycine at position 42 is substituted by another amino acid and wherein the numbering of the amino acids of the IGF-1 part of said protein corresponds to SEQ ID NO.: 5. The E-peptide may be the Ea, Eb, or Ec peptide and the amino acid by which the glycine at position 42 is substituted is serine.

Thus, in one embodiment, the disclosure relates to a polypeptide comprising a human IGF-1 precursor protein; (a) wherein the amino acid G42 is deleted or substituted by the amino acid serine; and (b) which is linked to an immunoglobulin Fc region, particularly a modified Fc region, particularly an Fc region, which is modified to modulate its binding to the Fc receptor. For example, one or more amino acids can be replaced with a different amino acid residue such that the Fc region has an altered affinity for the Fc receptor or the C1 component of complement. So called silenced immunoglobulin Fc regions have been described in the art: LALA and N297A (Strohl, W., 2009, Curr. Opin. Biotechnol. vol. 20(6):685-691); and D265A (Baudino et al., 2008, J. Immunol. 181: 6664-69; Strohl, W., supra). Examples of silent Fc IgG1 antibodies comprise the so-called LALA mutant comprising L234A and L235A mutation in the IgG1 Fc amino acid sequence. Another example of a silent IgG1 antibody comprises the D265A mutation. Another silent IgG1 antibody comprises the N297A mutation, which results in aglycosylated/non-glycosylated antibodies.

The above mentioned LALA approach is described in further detail in U.S. Pat. No. 5,624,821 and U.S. Pat. No. 5,648,260 both by Winter et al. Thus in one embodiment the disclosed hIGF-1 precursor protein is fused to an Fc region comprising the L234A and L235A mutation or the D265A mutation or the N297A mutation. Such Fc LALA, D265A or N297A constructs have reduced ADCC activity In one embodiment, the polypeptide containing a human IGF-1 Ea-peptide precursor protein fused to an immunoglobulin Fc region, wherein the amino acid glycine at position 42 is substituted by the amino acid serine, comprises additional deletions and/or mutations at amino acids G1, P2, E3, R36, R37, K68, S69, A70, R71, S72, R74, R77 and/or R104.

Examples of such molecules include, but are not limited to, the following polypeptides:

A polypeptide containing a human IGF-1 Ea-peptide precursor protein fused to an immunoglobulin Fc region wherein the amino acid glycine at position 42 is substituted by the amino acid serine, wherein the numbering of the amino acids of the IGF-1 part of said protein corresponds to SEQ ID NO.: 5 and wherein the amino acid(s)
(1b) G1, P2, E3 are deleted, amino acid R36 is substituted or deleted and the amino acids R71 and S72 are deleted.
(2b) G1, P2, E3 are deleted, amino acid R36 is substituted by glutamine (Q) and the amino acids R71 and S72 are deleted.
(3b) G1, P2, E3 are deleted, amino acid R37 is substituted or deleted and the amino acids R71 and S72 are deleted.
(4b) G1, P2, E3 are deleted, amino acid R37 is substituted by glutamic acid (E) and the amino acids R71 and S72 are deleted.
(5b) G1, P2, E3 are deleted, amino acid R37 is substituted by alanine and the amino acids R71 and S72 are deleted.
(6b) G1, P2, E3 are deleted, amino acid R37 is substituted by proline (P) and the amino acids R71 and S72 are deleted.
(7b) G1, P2, E3 are deleted, amino acids R36 and R37 are substituted or deleted and the amino acids R71 and S72 are deleted.
(8b) G1, P2, E3 are deleted, amino acid R36 and R37 are both substituted by glutamine (Q) and the amino acids R71 and S72 are deleted.
(9b) G1, P2, E3 are deleted, amino acid R36 is substituted by glutamine (Q), R37 is substituted by alanine and the amino acids R71 and S72 are deleted.
(10b) G1, P2, E3 are deleted, amino acid R36 is substituted or deleted and the amino acids R71 and S72 are deleted and amino acid R74 is mutated to glutamine (Q).
(11b) G1, P2, E3 are deleted, amino acid R36 is substituted or deleted and the amino acids R71 and S72 are deleted and amino acids R74 and R77 are mutated to glutamine (Q).
(12b) G1, P2, E3 are deleted, amino acid R36 is substituted or deleted and the amino acids R71 and S72 are deleted and amino acids R74, R77 and Q104 are mutated to glutamine (Q).
(13b) G1, P2, E3 are deleted, amino acid R36 is substituted by glutamine (Q) and the amino acids R71 and S72 are deleted and amino acid R74 is mutated to glutamine (Q).
(14b) G1, P2, E3 are deleted, amino acid R36 is substituted by glutamine (Q) and the amino acids R71 and S72 are deleted and amino acids R74 and R77 are mutated to glutamine (Q).

(15b) G1, P2, E3 are deleted, amino acid R36 is substituted by glutamine (Q) and the amino acids R71 and S72 are deleted and amino acids R74, R77 and R104 are mutated to glutamine (Q).
(16b) G1, P2, E3 are deleted, amino acid R37 is substituted by glutamic acid (E) and the amino acids R71 and S72 are deleted and amino acid R77 is mutated to glutamine (Q).
(17b) G1, P2, E3 are deleted, amino acid R37 is substituted by glutamic acid (E) and the amino acids R71 and S72 are deleted and amino acids R74 and R77 are mutated to glutamine (Q).
(18b) G1, P2, E3 are deleted, amino acid R37 is substituted by glutamic acid (E) and the amino acids R71 and S72 are deleted and amino acids R74, R77 and R104 are mutated to glutamine (Q).
(19b) G1, P2, E3 are deleted, amino acid R37 is substituted by alanine (A) and the amino acids R71 and S72 are deleted and amino acid R74 is mutated to glutamine (Q).
(20b) G1, P2, E3 are deleted, amino acid R37 is substituted by alanine (A) and the amino acids R71 and S72 are deleted and amino acids R74 and R77 are mutated to glutamine (Q).
(21b) G1, P2, E3 are deleted, amino acid R37 is substituted by alanine (A) and the amino acids R71 and S72 are deleted and amino acids R74, R77 and R104 are mutated to glutamine (Q).
(22b) G1, P2, E3 are deleted, amino acid R37 is substituted by proline (P) and the amino acids R71 and S72 are deleted and amino acid R74 is mutated to glutamine (Q).
(23b) G1, P2, E3 are deleted, amino acid R37 is substituted by proline (P) and the amino acids R71 and S72 are deleted and amino acids R74 and R77 are mutated to glutamine (Q).
(24b) G1, P2, E3 are deleted, amino acid R37 is substituted by proline (P) and the amino acids R71 and S72 are deleted and amino acids R74, R77 and R104 are mutated to glutamine (Q).
(25b) G1, P2, E3 are deleted, amino acid R36 and R37 are both substituted by glutamine (Q) and the amino acids R71 and S72 are deleted and amino acid R74 is mutated to glutamine (Q).
(26b) G1, P2, E3 are deleted, amino acid R36 and R37 are both substituted by glutamine (Q) and the amino acids R71 and S72 are deleted and amino acids R74 and R77 are mutated to glutamine (Q).
(27b) G1, P2, E3 are deleted, amino acid R36 is substituted by glutamine (Q), R37 is substituted by alanine and the amino acids R71 and S72 are deleted and amino acids R74 and R77 are mutated to glutamine (Q).
(28b) G1, P2, E3 are deleted, amino acid R36 and R37 are both substituted by glutamine (Q) and the amino acids R71 and S72 are deleted and amino acids R74, R77 and R104 are mutated to glutamine (Q).
(29b) G1, P2, E3 are deleted, amino acid R36 is substituted by glutamine (Q), R37 is substituted by alanine and the amino acids R71 and S72 are deleted and amino acids R74, R77 and R104 are mutated to glutamine (Q).
(1c) G1, P2, E3 are deleted, amino acid R36 is substituted or deleted and the amino acids K68, S69, A70, R71 and S72 are deleted.
(2c) G1, P2, E3 are deleted, amino acid R36 is substituted by glutamine (Q) and the amino acids K68, S69, A70, R71 and S72 are deleted.
(3c) G1, P2, E3 are deleted, amino acid R37 is substituted or deleted and the amino acids K68, S69, A70, R71 and S72 are deleted.
(4c) G1, P2, E3 are deleted, amino acid R37 is substituted by glutamic acid (E) and the amino acids K68, S69, A70, R71 and S72 are deleted.
(5c) G1, P2, E3 are deleted, amino acid R37 is substituted by alanine and the amino acids K68, S69, A70, R71 and S72 are deleted.
(6c) G1, P2, E3 are deleted, amino acid R37 is substituted by proline (P) and the amino acids K68, S69, A70, R71 and S72 are deleted.
(7c) G1, P2, E3 are deleted, amino acids R36 and R37 are substituted or deleted and the amino acids K68, S69, A70, R71 and S72 are deleted.
(8c) G1, P2, E3 are deleted, amino acid R36 and R37 are both substituted by glutamine (Q) and the amino acids K68, S69, A70, R71 and S72 are deleted.
(9c) G1, P2, E3 are deleted, amino acid R36 is substituted by glutamine (Q), R37 is substituted by alanine and the amino acids K68, S69, A70, R71 and S72 are deleted.
(10c) G1, P2, E3 are deleted, amino acid R36 is substituted or deleted and the amino acids K68, S69, A70, R71 and S72 are deleted and amino acid R74 is mutated to glutamine (Q).
(11c) G1, P2, E3 are deleted, amino acid R36 is substituted or deleted and the amino acids K68, S69, A70, R71 and S72 are deleted and amino acids R74 and R77 are mutated to glutamine (Q).
(12c) G1, P2, E3 are deleted, amino acid R36 is substituted or deleted and the amino acids K68, S69, A70, R71 and S72 are deleted and amino acids R74, R77 and Q104 are mutated to glutamine (Q).
(13c) G1, P2, E3 are deleted, amino acid R36 is substituted by glutamine (Q) and the amino acids K68, S69, A70, R71 and S72 are deleted and amino acid R74 is mutated to glutamine (Q).
(14c) G1, P2, E3 are deleted, amino acid R36 is substituted by glutamine (Q) and the amino acids K68, S69, A70, R71 and S72 are deleted and amino acids R74 and R77 are mutated to glutamine (Q).
(15c) G1, P2, E3 are deleted, amino acid R36 is substituted by glutamine (Q) and the amino acids K68, S69, A70, R71 and S72 are deleted and amino acids R74, R77 and R104 are mutated to glutamine (Q).
(16c) G1, P2, E3 are deleted, amino acid R37 is substituted by glutamic acid (E) and the amino acids K68, S69, A70, R71 and S72 are deleted and amino acid R74 is mutated to glutamine (Q).
(17c) G1, P2, E3 are deleted, amino acid R37 is substituted by glutamic acid (E) and the amino acids K68, S69, A70, R71 and S72 are deleted and amino acids R74 and R77 are mutated to glutamine (Q).
(18c) G1, P2, E3 are deleted, amino acid R37 is substituted by glutamic acid (E) and the amino acids K68, S69, A70, R71 and S72 are deleted and amino acids R74, R77 and R104 are mutated to glutamine (Q). (19c) G1, P2, E3 are deleted, amino acid R37 is substituted by alanine (A) and the amino acids K68, S69, A70, R71 and S72 are deleted and amino acid R74 is mutated to glutamine (Q).
(20c) G1, P2, E3 are deleted, amino acid R37 is substituted by alanine (A) and the amino acids K68, S69, A70, R71 and S72 are deleted and amino acids R74 and R77 are mutated to glutamine (Q).
(21c) G1, P2, E3 are deleted, amino acid R37 is substituted by alanine (A) and the amino acids K68, S69, A70, R71 and S72 are deleted and amino acids R74, R77 and R104 are mutated to glutamine
(22c) G1, P2, E3 are deleted, amino acid R37 is substituted by proline (P) and the amino acids K68, S69, A70, R71 and S72 are deleted and amino acid R74 is mutated to glutamine (Q).

(23c) G1, P2, E3 are deleted, amino acid R37 is substituted by proline (P) and the amino acids K68, S69, A70, R71 and S72 72 are deleted and amino acids R74 and R77 are mutated to glutamine (Q).

(24c) G1, P2, E3 are deleted, amino acid R37 is substituted by proline (P) and the amino acids K68, S69, A70, R71 and S72 are deleted and amino acids R74, R77 and R104 are mutated to glutamine (Q).

(25c) G1, P2, E3 are deleted, amino acid R36 and R37 are both substituted by glutamine (Q) and the amino acids K68, S69, A70, R71 and S72 are deleted and amino acid R74 is mutated to glutamine (Q).

(26c) G1, P2, E3 are deleted, amino acid R36 and R37 are both substituted by glutamine (Q) and the amino acids K68, S69, A70, R71 and S72 are deleted and amino acids R74 and R77 are mutated to glutamine (Q).

27c) G1, P2, E3 are deleted, amino acid R36 is substituted by glutamine (Q), R37 is substituted by alanine and the amino acids K68, S69, A70, R71 and S72 are deleted and amino acids R74 and R77 are mutated to glutamine (Q).

(28c) G1, P2, E3 are deleted, amino acid R36 and R37 are both substituted by glutamine (Q) and the amino acids K68, S69, A70, R71 and S72 are deleted and amino acids R74, R77 and R104 are mutated to glutamine (Q).

(29c) G1, P2, E3 are deleted, amino acid R36 is substituted by glutamine (Q), R37 is substituted by alanine and the amino acids K68, S69, A70, R71 and S72 are deleted and amino acids R74, R77 and R104 are mutated to glutamine (Q).

In another embodiment the disclosure relates to the above describes proteins comprising the above described polypeptides (1 b)-(29c), wherein said molecules instead of being mutated at the positions 1-3, only the amino acid E3 is deleted (e.g. the molecule (28c) could also refer to a polypeptide comprising a human IGF-1 precursor protein fused to an immunoglobulin Fc region wherein the amino acid G42 is substituted by the amino acid amino acid serine and wherein the amino acid(s) E3 are deleted, amino acid R36 and R37 are both substituted by glutamine (Q) and the amino acids K68, S69, A70, R71 and S72 are deleted and amino acids R74, R77 and R104 are mutated to glutamine (Q).)

In another embodiment the disclosure relates to the above described polypeptides (e.g. the polypeptides 1-29c), comprising an mutated E-peptide consisting of the amino acids

```
                                          (SEQ ID. NO.: 25)
a) VQAQQHTDMPKTQKEVHLKNASG,
or
                                          (SEQ ID. NO.: 26)
b) VQAQQHTDMPKTQKYQPPATNKNTKSQRRKGS.

(SEQ NO: 115)
c) VQAQQHTDMPKTQKEVHLKNASRGSAGNKNYQM
```

In a further embodiment, the disclosure provides the above described IGF-1 precursor protein being fused to an Fc region, wherein the Fc region may be directly fused to the modified IGF-1 precursor polypeptide or may be connected by a hinge region using recombinant DNA technologies well known in the art. If a DNA hinge region is used, the Fc region may be connected to any part of the modified IGF-1 precursor polypeptide. In one embodiment the Fc region is fused directly to the C-terminus of the modified IGF-1 precursor polypeptide. In another embodiment, the Fc region is linked to the C-terminus of the modified IGF-1 precursor polypeptide by a Gly Ser (-GS-) linker.

A DNA linker may be used to provide a restriction site between components for ease of manipulation. A linker may also be provided to enhance expression of the polypeptide from a host cell, to decrease steric hindrance such that the component may assume its optimal tertiary or quaternary structure and/or interact appropriately with its target molecule. For linkers and methods of identifying desirable spacers, see, for example, George et al. (2003) Protein Engineering 15:871-879.

A linker sequence may include one or more amino acids naturally connected to a receptor component, or may be an added sequence used to enhance expression of the fusion protein, provide specifically desired sites of interest, allowing component domains to form optimal tertiary structures and/or to enhance the interaction of a component with its target molecule. In one embodiment, the linker comprises one or more peptide sequences which are between 1-100 amino acids, preferably 1-25 amino acids in length. In one embodiment, the linker is 1-5 amino acids in length. In one embodiment, the linker is a three amino acid sequence; more specifically, the three amino acid sequence of Gly Pro Gly. In another embodiment, the linker is Gly Ser.

Examples of such hinge molecules include, but are not limited to, the following polypeptides:

```
                              (SEQ ID NO.: 22)
             hinge 1: CPPCPA (SEQ ID NO.: 23)
             hinge 2: DKTHTCPPCPA (SEQ ID NO.: 24)
             hinge 3: EPKSCDKTHTCPPCPA
```

Consequently, the disclosure relates to a polypeptide containing a human IGF-1 Ea-peptide precursor protein which is fused to an immunoglobulin Fc region, particularly a modified Fc region, particularly an Fc region, which is modified to modulate its binding to Fc receptor, preferably by substituting one or both of amino acids 234 and 235 to alanine as described above, wherein the amino acid glycine at position 42 is substituted by serine, wherein the numbering of the amino acids corresponds to SEQ ID NO.: 5 and wherein the immunoglobulin Fc region is fused to the IGF-1 precursor protein via a hinge region. Examples of such molecules include, but are not limited to, the following polypeptides:

```
                                    (SEQ ID NO.: 8)
          hIgF1-Ea-Fc_mut 13/2_E (SEQ ID NO.: 9)
          hIgF1-Ea-Fc_mut 13/2_A (SEQ ID NO.: 10)
          hIgF1-Ea-Fc_mut 13/2_C (SEQ ID NO.: 11)
          hIgF1-Ea-Fc_mut 13/2_F (SEQ ID NO.: 12)
          hIgF1-Ea-Fc_mut 04/2_E (SEQ ID NO.: 13)
          hIgF1-Ea-Fc_mut 04/2_A (SEQ ID NO.: 14)
          hIgF1-Ea-Fc_mut 04/2_F
```

In one particular embodiment of the disclosure, the amino acids R71 and S72 of the above described IGF-1 precursor proteins can be mutated as follows:

(1) Deletion of one or both of R71 and S72, and/or (2) Mutating one or both of R71 and S72 to a non-basic amino acid, such as alanine, and/or (3) Inserting one or more non-basic amino acids between R71 and S72, and/or (4) Placing a glycosylation site near R71 and S72 sufficient to mask the protease site, and/or (5) Site-directed pegylation using replacement of either R71 or S72, or insertion near or between R71 and S72, with a non-natural amino acid.

Methods for protein modification like site directed mutagenesis, the introduction of glycosylation sites or site directed pegylation are well known to those skilled in the art.

In one embodiment, the Fc region is modified to modulate its binding to Fc receptor. In one embodiment, the Fc region is modified to reduce its affinity for Fc receptor. In one embodiment, the Fc region is modified to reduce ADCC activity. In one embodiment, the Fc region is modified to prevent ADCC activity.

In one embodiment, the invention provides a polypeptide comprising SEQ ID NO.: 8 (hIgF1-Ea-Fc_mut 13/2_E). In one embodiment, the invention provides a polypeptide comprising SEQ ID NO.: 9 (hIgF1-Ea-Fc_mut 13/2_A). In one embodiment, the invention provides a polypeptide comprising SEQ ID NO.:10 (hIgF1-Ea-Fc_mut 13/2_C). In one embodiment, the invention provides a polypeptide comprising SEQ ID NO.: 11 (hIgF1-Ea-Fc_mut 13/2_F).

In one embodiment, the invention provides a polypeptide comprising SEQ ID NO.:12 (hIgF1-Ea-Fc_mut 04/2_E).

In one embodiment, the invention provides a polypeptide comprising SEQ ID NO.:13 (hIgF1-Ea-Fc_mut 04/2_A).

In one embodiment, the invention provides a polypeptide comprising SEQ ID NO.:14 (hIgF1-Ea-Fc_mut 04/2_F).

In one embodiment, the invention provides a polypeptide consisting of SEQ ID NOs.:8, 9, 10, 11, 12, 13 or 14.

In one embodiment, the present disclosure provides a polypeptide that is at least 95%, at least 96%, at least 96%, at least 97%, at least 98%, at least 99% identical to SEQ ID NO.: 8.

In one embodiment, the present disclosure provides a polypeptide that is at least 95%, at least 96%, at least 96%, at least 97%, at least 98%, at least 99% identical to SEQ ID NO.: 9.

In one embodiment, the present disclosure provides a polypeptide that is at least 95%, at least 96%, at least 96%, at least 97%, at least 98%, at least 99% identical to SEQ ID NO.: 10.

In one embodiment, the present disclosure provides a polypeptide that is at least 95%, at least 96%, at least 96%, at least 97%, at least 98%, at least 99% identical to SEQ ID NO.: 11.

In one embodiment, the present disclosure provides a polypeptide that is at least 95%, at least 96%, at least 96%, at least 97%, at least 98%, at least 99% identical to SEQ ID NO.: 12.

In one embodiment, the present disclosure provides a polypeptide that is at least 95%, at least 96%, at least 96%, at least 97%, at least 98%, at least 99% identical to SEQ ID NO.: 13.

In one embodiment, the present disclosure provides a polypeptide that is at least 95%, at least 96%, at least 96%, at least 97%, at least 98%, at least 99% identical to SEQ ID NO.: 14.

In one embodiment, the polypeptides of the present invention are glycosylated.

Amino Acid Mutations

As referred to above, various amino acids may be mutated to another amino acid. Typically the amino acid is replaced with an alanine residue. However, other amino acids may be used, such as non-natural amino acids or natural amino acids from another group (i.e. polar, acidic, basic or non-polar). Methods of introducing a mutation into amino acids of a protein are well known to those skilled in the art. See, e.g., Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989)). Methods comprise, but are not limited to, amplification of the DNA encoding the polypeptide functionally active variant or fragments thereof by polymerase chain reaction (PCR) conducted with mutagenic primers and assembling the fragments by assembly PCR if needed or introduction of mutations using commercially available kits such as "QuikChange™ Site-Directed Mutagenesis Kit" (Stratagene). See, e.g., Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989)). Further, mutated sequences can be obtained by synthetic gene synthesis a service provided by commercial companies (e.g. Geneart, Life Technology). The generation of a polypeptide functionally active variant or derivative to a polypeptide by replacing an amino acid that does not influence the function of a polypeptide can be accomplished by one skilled in the art.

Immunoglobulin Fc Regions

In one embodiment, the Fc region is from IgG, IgM or IgA. In one embodiment the Fc region derives from IgG. The Fc domain of IgG may be selected from the isotypes IgG1, IgG2, IgG3, and IgG4, as well as any allotype within each isotype group. In one embodiment the Fc region is a human Fc region.

The Fc region may be altered by replacing at least one amino acid residue with a different amino acid residue to alter the effector functions of the Fc region. For example, one or more amino acids can be replaced with a different amino acid residue such that the Fc region has an altered affinity for the Fc receptor or the C1 component of complement. This approach is described in further detail in U.S. Pat. No. 5,624,821 and U.S. Pat. No. 5,648,260, both by Winter et al. In particular, residues 234 and 235 may be mutated. In particular, these mutations may be to alanine. Thus in one embodiment the antibody of the invention has a mutation in the Fc region at one or both of amino acids 234 and 235. In another embodiment, one or both of amino acids 234 and 235 may be substituted to alanine. Such an Fc variant where residues 234 and 235 have been substituted for alanine is commonly referred to as "LALA". Such Fc LALA constructs have reduced ADCC activity. In one embodiment, the IGF-1 precursor protein is linked to an IgG1 LALA Fc.

Linkage

"Fused to" or "linked to" as used herein in the context of the disclosed proteins fused to/linked to an immunoglobulin Fc region, shall mean combining two polypeptides that are not naturally present in the same polypeptide.

The immunoglobulin Fc region may be directly fused to the modified IGF-1 polypeptide or may be connected by a linker using recombinant DNA technologies well known in the art. If a DNA linker is used, the Fc region may be connected to any part of the modified IGF-1 polypeptide. In one embodiment the Fc region is fused directly to the C-terminus of the modified IGF-1 polypeptide. In another embodiment, the Fc region is linked to the C-terminus of the modified IGF-1 polypeptide by a Gly Ser (-GS-) linker and/or a hinge region (SEQ IDs NO.: 22 to 24) such as for hIgF1-Ea-Fc_mut 13/2_E (SEQ IDs NO.: 8), hIgF1-Ea-Fc_mut 13/2_A (SEQ IDs NO.: 9), hIgF1-Ea-Fc_mut 13/2_C (SEQ IDs NO.: 10), hIgF1-Ea-Fc_mut 13/2_F (SEQ IDs NO.: 11), hIgF1-Ea-Fc_mut 04/2_E (SEQ IDs NO.: 12), hIgF1-Ea-Fc_mut 04/2_A (SEQ IDs NO.: 13) or hIgF1-Ea-Fc_mut 04/2_F (SEQ IDs NO.:14).

A DNA linker may be used to provide a restriction site between components for ease of manipulation. A linker may also be provided to enhance expression of the polypeptide from a host cell, to decrease steric hindrance such that the component may assume its optimal tertiary or quaternary structure and/or interact appropriately with its target molecule. For linkers and methods of identifying desirable spacers, see, for example, George et al. (2003) Protein Engineering 15:871-879.

A linker sequence may include one or more amino acids naturally connected to a receptor component, or may be an added sequence used to enhance expression of the fusion protein, provide specifically desired sites of interest, allowing component domains to form optimal tertiary structures and/or to enhance the interaction of a component with its target molecule. In one embodiment, the linker comprises one or more peptide sequences which are between 1-100 amino acids, preferably 1-25 amino acids in length. In one embodiment, the linker is 1-5 amino acids in length. In one embodiment, the linker is a three amino acid sequence; more specifically, the three amino acid sequence of Gly Pro Gly. In another embodiment, the linker is Gly Ser.

Nucleic Acids

The invention also provides nucleic acid molecules that encode the polypeptides of the invention. Preferred nucleic acid sequences are those encoding hIgF1-Ea-Fc_mut 13/2_E, hIgF1-Ea-Fc_mut 13/2_A, hIgF1-Ea-Fc_mut 13/2_C, hIgF1-Ea-Fc_mut 13/2_F, hIgF1-Ea-Fc_mut 04/2_E, hIgF1-Ea-Fc_mut 04/2_A or hIgF1-Ea-Fc_mut 04/2_F (SEQ ID NOs.: 15-21). Nucleic acid molecules of the present invention may be in the form of RNA, such as mRNA, or in the form of DNA, including, for instance cDNA or synthetic DNA. The nucleic acid molecules may be double-stranded or single-stranded. Single-stranded DNA may be the coding strand, also known as the sense strand, or it may be the non-coding strand, also referred to as the anti-sense strand.

The degeneracy of the genetic code is well known. Thus two or more different nucleic acid sequences may code for the same polypeptide sequence. Such variant nucleic acid sequences are included within the scope of the application. Indeed, it may be preferable to make conservative modifications to a nucleic acid sequence to improve expression of a polypeptide of the invention.

The invention further provides a vector comprising a nucleic acid of the invention. The vector may be a cloning or expression vector. In one embodiment, the nucleic acid may be comprised within an expression vector carrying elements needed for efficient expression well known by the skilled person in the art. Elements include for example a promoter, such as for example the Cytomegalovirus (CMV) enhancer-promoter, a signal sequence for secretion, such as the natural or any other sequence known to facilitate secretion, a polyadenylation signal and transcription terminator, for example derived from Bovine Growth Hormone (BGH) gene, an element allowing episomal replication and replication in prokaryotes (e.g. SV40 origin and ColE1 or others known in the art) and elements to allow selection, such as ampicillin resistance gene and zeocin or hygromycin marker.

In one embodiment the invention provides an isolated nucleic acid molecule comprising a nucleotide sequence selected from the group consisting of:
a) the polynucleotide sequence set forth in SEQ ID NO.: 15 or a complement thereof;
b) a polynucleotide sequence comprising a sequence having at least 90%, at least 95%, at least 96%, at least 97%, at least 98% or at least 99% sequence identity to the entirety of the sequence set forth in SEQ ID NO.: 15;
c) the polynucleotide sequence set forth in SEQ ID NO.: 16 or a complement thereof;
d) a polynucleotide sequence comprising a sequence having at least 90%, at least 95%, at least 96%, at least 97%, at least 98% or at least 99% sequence identity to the entirety of the sequence set forth in SEQ ID NO.: 16;
e) the polynucleotide sequence set forth in SEQ ID NO.: 17 or a complement thereof;
f) a polynucleotide sequence comprising a sequence having at least 90%, at least 95%, at least 96%, at least 97%, at least 98% or at least 99% sequence identity to the entirety of the sequence set forth in SEQ ID NO.: 17;
g) the polynucleotide sequence set forth in SEQ ID NO.: 18 or a complement thereof;
h) a polynucleotide sequence comprising a sequence having at least 90%, at least 95%, at least 96%, at least 97%, at least 98% or at least 99% sequence identity to the entirety of the sequence set forth in SEQ ID NO.: 18;
i) the polynucleotide sequence set forth in SEQ ID NO.: 19 or a complement thereof;
j) a polynucleotide sequence comprising a sequence having at least 90%, at least 95%, at least 96%, at least 97%, at least 98% or at least 99% sequence identity to the entirety of the sequence set forth in SEQ ID NO.: 19;
k) the polynucleotide sequence set forth in SEQ ID NO.: 20 or a complement thereof;
l) a polynucleotide sequence comprising a sequence having at least 90%, at least 95%, at least 96%, at least 97%, at least 98% or at least 99% sequence identity to the entirety of the sequence set forth in SEQ ID NO.: 20;
m) the polynucleotide sequence set forth in SEQ ID NO.: 21 or a complement thereof;
n) a polynucleotide sequence comprising a sequence having at least 90%, at least 95%, at least 96%, at least 97%, at least 98% or at least 99% sequence identity to the entirety of the sequence set forth in SEQ ID NO.: 21.

In another embodiment the disclosure relates to the above described IGF-1 variant polypeptides, wherein said human IGF-1 precursor proteins are pegylated. The pegylation is particularly preferred for IGF-1 precursor proteins that are not fused to an immunoglobulin Fc region of a human IgG. Conjugation to poly(ethylene glycol) (PEG; pegylation) have proven to be beneficial in prolonging the half-life of therapeutic proteins drugs. It is expected that pegylation of the IGF precursor polypeptides of the invention may result in similar pharmaceutical advantages. Methods of pegylation of IGF-1 are well known in the art. See, for example, US Patent Application Publication 2006/0154865, which describes the beneficial properties of lysine-monopegylated IGF-1. Such lysine-monopegylation can be adapted for the precursor IGF polypeptides of the invention. In addition, pegylation can be achieved in any part of a polypeptide of the invention by the introduction of a nonnatural amino acid. Certain nonnatural amino acids can be introduced by the technology described in Deiters et al., J Am Chem Soc 125:11782-11783, 2003; Wang and Schultz, Science 301: 964-967, 2003; Wang et al., Science 292:498-500, 2001; Zhang et al., Science 303:371-373, 2004 or in U.S. Pat. No. 7,083,970. Briefly, some of these expression systems involve site-directed mutagenesis to introduce a nonsense codon, such as an amber TAG, into the open reading frame encoding a polypeptide of the invention. Such expression vectors are then introduced into a host that can utilize a tRNA specific for the introduced nonsense codon and charged with the nonnatural amino acid of choice. Particular nonnatural amino acids that are beneficial for purpose of conjugating moieties to the polypeptides of the invention include those with acetylene and azido side chains. The IGF precursor polypeptides containing these novel amino acids can then be pegylated at these chosen sites in the protein. In addition, such pegylated IGF molecules without the E-peptide are also useful as therapeutics.

Production of the IGF-1 Variants of the Invention in Mammalian Cells

The production of native human IGF-1 in prokaryotic expression systems is well known to the person skilled in the art. Expression in eukaryotic cells, in particular mammalian host cells, is sometimes preferred because such eukaryotic cells are more likely than prokaryotic cells to assemble and secrete a properly folded and immunologically active protein.

Mammalian host cells for expressing the recombinant antibodies of the invention include Chinese Hamster Ovary (CHO cells) (including dhfr− CHO cells, described Urlaub and Chasin, 1980 Proc. Natl. Acad. Sci. USA 77:4216-4220 used with a DHFR selectable marker, e.g. as described in R. J. Kaufman and P. A. Sharp, 1982 Mol. Biol. 159:601-621), HEK293 cells (Human Embryonic Kidney 293 cells), NSO murine myeloma cells, COS cells and SP2 cells. Preferred host cells are CHO K1 derivative cells. However, expression of recombinant IGF-1 in CHO cell lines result in cell growth inhibition and low titers (see FIGS. 11/12). Stable knockdown/knockout of IGF-1-R in CHO cells using "zinc finger nuclease" technology resulted in an improved cell growth and higher IGF-1 protein titers (FIGS. 14, 15, 16). CHO cells with reduced expression of IGF-1-R (si/shRNA knockdown) which were stable transfected with plasmids encoding IGF-1 produced ca. 5 fold higher pool titer compared to stable transfected wild type CHO cells. Even higher pool titer could be measured after stable transfection of IGF-1-R knockout cell lines. A 5-20 fold titer increase of recombinant IGF-1 could be detected compared to the wild type CHO cell line. In summary these data show that knockdown or knockout of the IGF-1 receptor genes in mammalian cell lines can significantly improve the production of IGF-1 and variants thereof.

Hence, a suitable method for the production of recombinant IGF-1 or variants thereof in mammalian cells, for example a CHO cell, wherein said mammalian cell being deficient in the expression of a functional Insulin like growth factor 1 receptor (IGF-1R) comprises the following step:

a. Producing a mammalian cell being deficient in the expression of the Insulin like growth factor 1 receptor;
b. Transforming the cell of step a. with an expression vector comprising a nucleic acid molecule encoding an IGF-1 or a variant thereof;
c. Selecting a cell of step b. being transformed;
d. Cultivating the cell selected in step c. under conditions allowing the expression of the IGF-1 or a variant thereof; and
e. Harvesting the IGF-1 or a variant thereof from the mammalian cells cultivated in step d, wherein alternatively the order of steps a. and b. can be reversed or both steps can be performed at the same time.

The skilled person knows how to transform, select and cultivate genetically modified mammalian cells, e.g. CHO cells, like CHO-K1 derivative cells, CHO-DUXB11 derivative cells or CHO-DG44 cells. Selection protocols are routinely used to facilitate selection of cells that are likely to have integrated the recombinant DNA encoding the desired therapeutic protein, like growth factors, e.g. IGF-1. Antibiotic resistance or the ability to grow in a nutritionally selective medium conferred by a gene co-integrated on the transformation vector is routinely used. (see Weber, W. and Fussenegger, M. (2003) Inducible gene expression in mammalian cells, in Gene transfer and expression in mammalian cells, (Makrides, S. C., Ed.), Elsevier: Amsterdam, pp. 589-604) (Efficient selection for high-expression transfectants with a novel eukaryotic vector: Niwa Hitoshi, Yamamura Ken-ichi, Miyazaki Jun-ichi). The two most common CHO expression systems for recombinant protein production utilize dihydrofolate reductase (DHFR)-based methotrexate (MTX) selection or glutamine synthetase (GS)-based methionine sulfoximine (MSX) selection (Rita Costa A, Elisa Rodrigues M, Henriques M, Azeredo J, Oliveira R. Eur J Pharm Biopharm. 2010 February; 74(2):127-38. Epub 2009 Oct. 22. Guidelines to cell engineering for monoclonal antibody production).

Vectors particularly suitable for producing polypeptides in mammalian cells, particularly rodent cells such as CHO and DHFR gene defective CHO cells have been disclosed in the patent application WO09080720A. There are several appropriate methods known in the prior art for introducing an expression vector into a mammalian host cell. Respective methods include but are not limited to calcium phosphate transfection, electroporation, lipofection, biolistic- and polymer-mediated genes transfer. Suitable host cells are described above. After introduction of the expression vector nucleic acid into the host cell(s), the obtained transformants are cultured under selective conditions suitable for assaying the expression of the mammalian selectable marker gene enclosed in the expression cassette (MSM). This means, that for example when the mammalian selectable marker gene is an antibiotic resistance gene, transformants are cultured in a medium containing the corresponding antibiotic active in mammalian cells and the transformants which are viable under such conditions are selected, thus enabling the obtainment of transformants which express the marker gene and thus incorporated the vector. Additionally, a second selection step may be performed by culturing the transformants in a selection medium adapted for selecting the amplifiable, selectable marker gene comprised in the expression cassette (MASM). E.g. in case DHFR is used as an amplifiable, selectable marker gene, the transformants can be cultured in a nucleotide or purine-free medium in the presence of a DHFR inhibitor. In case an inducible promoter is used in at least one expression cassette, a corresponding induction signal should be provided in order to commence expression of the polypeptide. In order to make use of the DHFR selection/amplification system, said host cells may be cultured in the presence of a DHFR inhibitor. Suitable DHFR inhibitors are antifolates such as e.g. MTX. The concentration of antifolate/MTX used depends on the host cell and the DHFR variant incorporated in the vector. The concentration range can be chosen for multistep amplification procedures in DHFR" host cells for example at values around 5 nM-20 nM ranging to values of 500 nM to 1000 nM or even higher for secondary or further amplification steps. For DHFR+ cells starting concentrations are usually higher in the range of 100 nM to 750 nM, preferably 500 nM in the first steps and 500 nM to 1000 nM and above for further amplification steps. Suitable DHFR variants are described above.

In order to make use of the GS selection/amplification system said host cells may be cultured in the presence of e.g. MSX. The concentration of MSX used depends on the host cell. The concentration range can be chosen between from about 15 to 150 micromolar, 20 to 100 micromolar and 25 to 50 micromolar. These ranges are particularly suitable for NSO and CHO cells.

Pharmaceutical Compositions

In another aspect, the present invention provides a composition, e.g. a pharmaceutical composition, containing one or a combination of the above described IGF-1 variants, formulated together with a pharmaceutically acceptable carrier. Pharmaceutical compositions of the invention also can be administered in combination therapy, i.e. combined with other agents. For example, the IGF-1 variants of the present invention can be combined with at least one muscle mass/strength increasing agent, for example, anti-ActRIIB antibody, IGF-2 or variants IGF-2, an anti-myostatin antibody, a myostatin propeptide, a myostatin decoy protein that binds ActRIIB but does not activate it, a beta 2 agonist, a Ghrelin agonist, a SARM, GH agonists/mimetics or follistatin. Examples of therapeutic agents that can be used in combination therapy are described in greater detail below in the section on uses of the IGF-1 variants of the invention.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutically acceptable carrier include any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g. by injection or infusion). Depending on the route of administration, the active compound, i.e. antibody, immunoconjuage, or bispecific molecule, may be coated in a material to protect the compound from the action of acids and other natural conditions that may inactivate the compound.

A pharmaceutical composition of the invention also may include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin. Sterile injectable solutions can be prepared by incorporating the active compound in the required amount in an appropriate solvent with one or a combination of agents enumerated above, as required, followed by sterilization microfiltration. Generally, dispersions are prepared by incorporating the active compound into a sterile vehicle that contains a basic dispersion medium and the required other agents from those enumerated above. In the case of sterile powders for the preparation of sterile injectable solutions, the methods of preparation are vacuum drying and freeze-drying (lyophilization) that yield a powder of the active agent plus any additional desired agent from a previously sterile-filtered solution thereof.

The amount of active agent which can be combined with a carrier material to produce a single dosage form will vary depending upon the subject being treated, and the particular mode of administration. The amount of active agent which can be combined with a carrier material to produce a single dosage form will generally be that amount of the composition which produces a therapeutic effect. Generally, out of one hundred percent, this amount will range from about 0.01 percent to about ninety-nine percent of active agent, from about 0.1 percent to about 70 percent, or from about 1 percent to about 30 percent of active agent in combination with a pharmaceutically acceptable carrier.

Dosage regimens are adjusted to provide the optimum desired response (e.g. a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals.

A therapeutically effective amount of a polypeptide in the context of administrating the IGF-1 variants of the disclosure or composition comprising said IGF-1 variants, ranges from about 0.001 to 100 mg/kg, or 0.01 to 30 mg/kg, and more usually 0.1 to 10 mg/kg of the host body weight. For example dosages can be about 0.1 mg/kg body weight, can be about 0.2 mg/kg body weight, can be about 0.3 mg/kg body weight, can be about 1 mg/kg body weight, can be about 3 mg/kg body weight, can be about 5 mg/kg body weight or about 10 mg/kg body weight. The skilled person knows to identify a suitable effective dose, which will vary depending on the rout of administration (e.g. intraveneously or subcutaneously). An exemplary treatment regime entails administration once per day, once every week, once every two weeks, once every three weeks, once every four weeks or once a month. Such administration may be carried out intraveneously or subcutaneously. Dosage regimens for IGF-1 variants of the invention include 0.1 mg/kg body weight or 0.2 mg/kg body weight or 0.3 mg/kg body weight or 0.5 mg/kg body weight or 1 mg/kg body weight or 3 mg/kg body weight or 10 mg/kg body weight by intravenous administration. Alternatively, the composition can be a sustained release formulation, in which case less frequent administration is required. Dosage and frequency vary depending on the half-life of the antibody in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime. Actual dosage levels of the active agents in the pharmaceutical compositions of the present invention may be varied so as to obtain an amount of the active agent which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Administration of a therapeutically effective dose of an IGF-1 variant comprised in the compositions of the invention can result in a decrease in severity of disease symptoms, an increase in frequency and duration of disease symptom-free periods, or a prevention of impairment or disability due to the disease affliction i.e. an increase in muscle mass and/or function or decrease/reduction of wound area in burn patients.

Patients will receive an effective amount of the polypeptide active ingredient i.e. an amount that is sufficient to detect, treat, ameliorate, or prevent the disease or disorder in question. Therapeutic effects may also include reduction in physical symptoms. The optimum effective amount and concentration of a therapeutic protein for any particular subject will depend upon various factors, including the patient's age size health and/or gender, the nature and extent of the condition, the activity of the particular therapeutic protein, the rate of its clearance by the body, and also on any possible further therapeutic(s) administered in combination with the therapeutic protein. The effective amount delivered for a given situation can be determined by routine experimentation and is within the judgment of a clinician. Dosage can be by a single dose schedule or a multiple dose schedule.

A composition of the present invention can be administered by one or more routes of administration using one or more of a variety of methods known in the art. As will be appreciated by the skilled artisan, the route and/or mode of administration will vary depending upon the desired results. Routes of administration for the therapeutic proteins of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion. In one embodiment the antibody comprising composition is administered intravenously. In another embodiment the antibody is administered subcutaneously.

Alternatively, an IGF-1 variant comprising composition of the invention can be administered by a nonparenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g. Sustained and Controlled Release Drug Delivery Systems, J. R. Robinson, ed., Marcel Dekker, Inc., New York, 1978. Therapeutic compositions can be administered with medical devices known in the art. For example, in one embodiment, a therapeutic composition of the invention can be administered with a needleless hypodermic injection device, such as the devices shown in U.S. Pat. Nos. 5,399,163; 5,383,851; 5,312,335; 5,064,413; 4,941,880; 4,790,824 or 4,596,556. Examples of well known implants and modules useful in the present invention include: U.S. Pat. No. 4,487,603, which shows an implantable micro-infusion pump for dispensing medication at a controlled rate; U.S. Pat. No. 4,486,194, which shows a therapeutic device for administering medicants through the skin; U.S. Pat. No. 4,447,233, which shows a medication infusion pump for delivering medication at a precise infusion rate; U.S. Pat. No. 4,447,224, which shows a variable flow implantable infusion apparatus for continuous drug delivery; U.S. Pat. No. 4,439,196, which shows an osmotic drug delivery system having multi-chamber compartments; and U.S. Pat. No. 4,475,196, which shows an osmotic drug delivery system. Many other such implants, delivery systems, and modules are known to those skilled in the art and include those made by MicroCHIPS™ (Bedford, Mass.).

In certain embodiments, the human IGF-1 variant comprising composition of the invention can be formulated to ensure proper distribution in vivo. For example, the blood-brain barrier (BBB) excludes many highly hydrophilic compounds. To ensure that the therapeutic compounds of the invention cross the BBB (if desired); they can be formulated, for example, in liposomes. For methods of manufacturing liposomes, see, e.g. U.S. Pat. Nos. 4,522,811; 5,374,548; and 5,399,331. The liposomes may comprise one or more moieties which are selectively transported into specific cells or organs, thus enhance targeted drug delivery (see, e.g. V. V. Ranade, 1989 J. Clin Pharmacol. 29:685). Exemplary targeting moieties include folate or biotin (see, e.g. U.S. Pat. No. 5,416,016); mannosides (Umezawa et al., 1988 Biochem. Biophys. Res. Commun. 153:1038); antibodies (P. G. Bloeman et al., 1995 FEBS Lett. 357:140; M. Owais et al., 1995 Antimicrob. Agents Chemother. 39:180); surfactant protein A receptor (Briscoe et al., 1995 Am. J. Physiol. 1233:134); p 120 (Schreier et al., 1994 J. Biol. Chem. 269:9090); see also K. Keinanen; M. L. Laukkanen, 1994 FEBSLett. 346:123; J. J. Killion; I. J. Fidler, 1994 Immunomethods 4:273.

Target Diseases and Disorders

The invention provides a polypeptide, nucleic acid or pharmaceutical composition of the invention for use in therapy. The invention further provides a polypeptide, nucleic acid or pharmaceutical composition of the invention for use in the treatment of a pathological disorder. The invention further provides use of a polypeptide, nucleic acid or pharmaceutical composition of the invention in the manufacture of a medicament for the treatment of a pathological disorder. The invention further provides a method of treating a patient suffering from a pathological disorder comprising administering a therapeutically effective amount of a polypeptide, nucleic acid or pharmaceutical composition of the invention to said patient.

The pathological disorder may be a musculoskeletal disease or disorder, such as muscle atrophy. There are many causes of muscle atrophy, including as a result of treatment with a glucocorticoid such as cortisol, dexamethasone, betamethasone, prednisone, methylprednisolone, or prednisolone. The muscle atrophy can also be a result of denervation due to nerve trauma or a result of degenerative, metabolic, or inflammatory neuropathy (e.g., Guillian-Barré syndrome, peripheral neuropathy, or exposure to environmental toxins or drugs).

In addition, the muscle atrophy can be a result of myopathy, such as myotonia; a congenital myopathy, including nemalene myopathy, multi/minicore myopathy and myotubular (centronuclear) myopathy; mitochondrial myopathy; familial periodic paralysis; inflammatory myopathy; metabolic myopathy, such as caused by a glycogen or lipid storage disease; dermatomyositisis; polymyositis; inclusion body myositis; myositis ossificans; rhabdomyolysis and myoglobinurias.

In another embodiment of the disclosure, the pharmaceutical composition of the invention can be used for the treatment of Kennedy Disease or chronic kidney disease The myopathy may be caused by a muscular dystrophy syndrome, such as Duchenne, Becker, myotonic, fascioscapulohumeral, Emery-Dreifuss, oculopharyngeal, scapulohumeral, limb girdle, Fukuyama, a congenital muscular dystrophy, or hereditary distal myopathy. The musculoskeletal disease can also be osteoporosis, a bone fracture, short stature, or dwarfism.

In addition, the muscle atrophy can be a result of an adult motor neuron disease such as amyotrophic lateral sclerosis; infantile spinal muscular atrophy, juvenile spinal muscular atrophy, autoimmune motor neuropathy with multifocal conductor block, paralysis due to stroke or spinal cord injury, skeletal immobilization due to trauma, prolonged bed rest, voluntary inactivity, involuntary inactivity, metabolic stress or nutritional insufficiency, cancer, AIDS, fasting, a thyroid gland or adrenal gland or pituitary gland disorder, diabetes, benign congenital hypotonia, central core disease, liver diseases (examples such as fibrosis, cirrhosis), sepsis, renal failure, congestive heart failure, ageing, space travel or time spent in a zero gravity environment.

In a particular embodiment, the pharmaceutical composition of the invention can be used for the treatment of burn patients including adult and pediatric burn injury, suffering from loss of lean body mass and/or muscle wasting.

Examples of age-related conditions that may be treated include sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, frailty, memory loss, wrinkles, impaired kidney function, and age-related hearing loss; metabolic disorders, including Type II Diabetes, Metabolic Syndrome, hyperglycemia, and obesity.

In a particular embodiment, the pharmaceutical composition of the invention can be used for the treatment of chronic obstructive pulmonary disease (COPD) patients In another embodiment of the disclosure the pharmaceutical composition of the invention can be used for the treatment of muscle atrophy. In a particular embodiment the disclosure relates to the use of the pharmaceutical composition of the invention for the treatment of muscle atrophy, wherein the atrophy group is selected from the group consisting of obesity-associated sarcopenia, sarcopenia, and diabetes-associated muscle atrophy.

Other conditions that may be treated include acute and/or chronic renal disease or failure, liver fibrosis or cirrhosis, cancer such as pancreatic, gastrointestinal (including esophageal, gastric, and colon), lung, prostate, lymphoma, or breast cancer; Parkinson's Disease; conditions associated with neuronal death, such as ALS (amyotrophic lateral sclerosis), brain atrophy, or dementia and anemia; chronic infections such as tuberculosis, whether caused by *Mycobacterium tuberculosis* or by atypical mycobacteria; chronic fungal infections; and opportunistic infections in the setting of immune suppression, whether iatrogenic or due to AIDS.

Further conditions include cachexia, cachexia associated with a rheumatoid arthritis and cachexia associated with cancer.

In another embodiment the disclosure relates to method of treating a muscle disorder, the method comprising administering a therapeutically effective amount, as described above, of the polypeptides of the invention. The need of treatment with the disclosed polypeptides or compositions comprising them to increase muscle mass can result from one of the above mentioned conditions, particularly as a consequence of a musculoskeletal disease or disorder, such as muscle atrophy, wherein the muscle disorder is a muscle atrophy selected from the group consisting of obesity-associated sarcopenia, sarcopenia, and diabetes-associated muscle atrophy.

Additionally, the disclosure relates to method of treating a burn injury, a chronic obstructive pulmonary disease (COPD), an age related condition like sarcopenia, the Kennedy disease, or a chronic kidney disease, comprising administering a therapeutically effective amount to a patient, as described above, of the polypeptides of the invention.

In another embodiment, the disclosure relates to a method for increasing muscle mass. In a particular embodiment, the disclosure relates to a method for increasing muscle mass in a patient in need thereof. The need to increase muscle mass can result from one of the above mentioned conditions, particularly as a consequence of a musculoskeletal disease or disorder, such as muscle atrophy. The need to increase muscle mass can also result from a burn injury, a chronic obstructive pulmonary disease (COPD), an age related condition like sarcopenia, the Kennedy disease, or a chronic kidney disease.

Patient Administration

A pharmaceutical composition of the invention can be administered to a patient. Administration will typically be via a syringe. Thus the invention provides a delivery device (e.g. a syringe) including a pharmaceutical composition of the invention.

Various delivery systems are known and can be used to administer the polypeptide of the invention, e.g., encapsulation in liposomes, microparticles, microcapsules, recombinant cells capable of expressing the protein, receptor-mediated endocytosis (see, e.g., Wu and Wu, J Biol Chem 262:4429-4432, 1987), construction of a nucleic acid as part of a retroviral, adeno-associated viral, adenoviral, poxviral (e.g., avipoxviral, particularly fowlpoxviral) or other vector, etc. Methods of introduction can be enteral or parenteral and include but are not limited to intradermal, intramuscular, intraperitoneal, intravenous, subcutaneous, pulmonary, intranasal, intraocular, epidural, and oral routes. The polypeptides can be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

In another embodiment, the pharmaceutical composition can be delivered in a vesicle, in particular a liposome (see Langer, Science 249:1527-1533, 1990). In yet another embodiment, the active agent can be delivered in a controlled release system. In one embodiment, a pump may be used.

Patient Groups

Patients who can benefit from the proposed treatment include patients recovering from acute or critical illness requiring intensive care or prolonged hospitalization (more than 1 week); frail elderly patients with sarcopenia; young adults recovering from severe trauma, such as motor vehicle accidents, severe burns, combat injuries, and other traumatic injuries; patients with chronic diseases known to cause cachexia, as listed above; and patients with muscle diseases, as listed above. Since loss of muscle is a common complication of most illnesses that are either severe or prolonged, it is anticipated that reversal of muscle wasting will speed the recovery and return to function of patients who experience muscle loss regardless of the root cause of this loss.

Combination Therapy

This treatment may be combined with any treatment aimed at the primary cause of the muscle wasting process. Such combinations may include corticosteroids, immune suppressive agents, anti-cytokine agents, anti-cancer drugs; growth factors such as erythropoeitin, G-CSF, GM-CSF, or others; drugs used for the treatment of diabetes (including insulin and oral hypoglycemic agents), anti-tuberculosis drugs, and antibiotics. Combinations may include both small molecule and biomolecule agents.

The pharmaceutical compositions of the invention may be administered as the sole active agent or in conjunction with, e.g. as an adjuvant to or in combination to, other drugs e.g. an ActRIIB antibody, an ActRIIA antibody, a soluble ActRIIB decoy mimetic, an anti-myostatin antibody, a myostatin propeptide, a myostatin decoy protein that binds ActRIIB but does not activate it, a beta 2 agonist, a Ghrelin agonist, a SARM, GH agonists/mimetics or follistatin. For example, the drug of the invention may be used in combination with an ActRIIB antibody as disclosed in WO2010125003.

Sequences

| SEQ ID NO. | DNA/PROT. | Description | Sequence |
|---|---|---|---|
| 1 | PROT. | hIGF-1 without the leader sequence | GPETLCGAELVDALQFVCGDRGFYFNKPTGYGSSSRRAPQTGIVDECCFRSCDLRLEMYCAPLKPAKSA |
| 2 | PROT. | Ea peptide | RSVRAQRHTDMPKTQKEVHLKNASRGSAGNKNYRM |
| 3 | PROT. | Eb peptide | RSVRAQRHTDMPKTQKYQPPSTNKNTKSQRRKGWPKTHPGGEQKEGTEASLQIRGKKKEQRREIGSRNAECRGKKGK |
| 4 | PROT. | Ec peptide | RSVRAQRHTDMPKTQKYQPPSTNKNTKSQRRKGSTFEERK |
| 5 | PROT. | Wild type IGF-1-Ea without the leader sequence | GPETLCGAELVDALQFVCGDRGFYFNKPTGYGSSSRRAPQTGIVDECCFRSCDLRLEMYCAPLKPAKSARSVRAQRHTDMPKTQKEVHLKNASRGSAGNKNYRM |
| 6 | PROT. | hIGF1-Ea-D1-3, R37A, D71-72, 77-fc domain | TLCGAELVDALQFVCGDRGFYFNKPTGYGSSRAAPQTGIVDECCFRSCDLRLEMYCAPLKPAKSAVRAQHTDMPKTQKEVHLKNASRGSAGNKNYRMGSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 7 | PROT. | hIGF1-Ea-D1-3, R37A, D71-72, R77Q-fc domain | TLCGAELVDALQFVCGDRGFYFNKPTGYGSSRAAPQTGIVDECCFRSCDLRLEMYCAPLKPAKSAVRAQQHTDMPKTQKEVHLKNASRGSAGNKNYRMGSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 8 | PROT. | hIGF1-Ea-Fc mut 13/2_E | TLCGAELVDALQFVCGDRGFYFNKPTGYGSSSQAAPQTSIVDECCFRSCDLRLEMYCAPLKPAVQAQQHTDMPKTQKEVHLKNASRGSAGNKNYQMDKTHTCPPCPAPEAAGGPSVFLFPPKPKDTLMISRTPEVTCVVVDVSHEDPEVKFNMYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 9 | PROT. | hIGF1-Ea-Fc mut 13/2_A | TLCGAELVDALQFVCGDRGFYFNKPTGYGSSSQAAPQTSIVDECCFRSCDLRLEMYCAPLKPAVQAQQHTDMPKTQKEVHLKNASRGSAGNKNYQMCPPCPAPEAAGGPSVFLFPPKPKDTLMISRTPEVTCVVVDVSHEDPEVKFNVYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 10 | PROT. | hIGF1-Ea-Fc mut 13/2_C | TLCGAELVDALQFVCGDRGFYFNKPTGYGSSSQAAPQTSIVDECCFRSCDLRLEMYCAPLKPAVQAQQHTDMPKTQKEVHLKNASGCPPCPAPEAAGGPSVFLFPPKDTLMISRTPEVTCVVVDVSHEDPEVKFNWYVDGVEVHNAKTKPREEQYNSTYRVVSVLTVLHQDWLNGKEYKCKV |

| SEQ ID NO. | DNA/ PROT. | Description | Sequence |
|---|---|---|---|
| 11 | PROT. | hIgF1-Ea-Fc mut 13/2_F | SNKALPAPIEKTISKAKGQPREPQVVTLPSREEMTKNQVSLTCLVKGFYPSDIAVEWESNGQ PENNYKTTPPVLDSDGSFFLYSKLTVDKSRWQQGNVFSCSVMHEALHNHYTQKSLSLSPGK |
| 11 | PROT. | hIgF1-Ea-Fc mut 13/2_F | TLCGAELVDALQFVCGDRGFYFNKPTGYGSSSQAAPQTSIVDECCFRSCDLRRLEMYCAPLK PAVQAQQHTDMPKTQKEVHLKNASGDKTHTCPPCPAPEAAGGPSVFLFPPKPKDTLMISRTP EVTCVVVDVSHEDPEVKFNVVYVDGVEVHNAKTKPREEQYNSTYRVVSVLTVLHQDWLNGKE YKCKVSNKALPAPIEKTISKAKGQPREPQVVTLPPSREEMTKNQVSLTCLVKGFYPSDIAVEWE SNGQPENNYKTTPPVLDSDGSFFLYSKLTVDKSRWQQGNVFSCSVMHEALHNHYTQKSLSL SPGK |
| 12 | PROT. | hIgF1-Ea-Fc mut 04/2_E | TLCGAELVDALQFVCGDRGFYFNKPTGYGSSSREAPQTSIVDECCFRSCDLRRLEMYCAPLK PAVQAQQHTDMPKTQKEVHLKNASRGSADNNYQMDKTHTCPPCPAPEAAGGPSVFLFPPK PKDTLMISRTPEVTCVVVDVSHEDPEVKFNWYVDGVEVHNAKTKPREEQYNSTYRVVSVLTV LHQDWLNGKEYKCKVSNKALPAPIEKTISKAKGQPREPQVVTLPPSREEMTKNQVSLTCLVKG FYPSDIAVEWESNGQPENNYKTTPPVLDSDGSFFLYSKLTVDKSRWQQGNVFSCSVMHEALH NHYTQKSLSLSPGK |
| 13 | PROT. | hIgF1-Ea-Fc mut 13/2_A | TLCGAELVDALQFVCGDRGFYFNKPTGYGSSSREAPQTSIVDECCFRSCDLRRLEMYCAPLK PAVQAQQHTDMPKTQKEVHLKNASRGSAGNKNYQMCPPCPAPEAAGGPSVFLFPPKPKDTL MISRTPEVTCVVVDVSHEDPEVKFNWYVDGVEVHNAKTKPREEQYNSTYRVVSVLTVLHQD WLNGKEYKCKVSNKALPAPIEKTISKAKGQPREPQVVTLPPSREEMTKNQVSLTCLVKGFYPS DIAVEWESNGQPENNYKTTPPVLDSDGSFFLYSKLTVDKSRWQQGNVFSCSVMHEALHNHY TQKSLSLSPGK |
| 14 | PROT. | hIgF1-Ea-Fc mut 04/2_F | TLCGAELVDALQFVCGDRGFYFNKPTGYGSSSREAPQTSIVDECCFRSCDLRRLEMYCAPLK PAVQAQQHTDMPKTQKEVHLKNASGDKTHTCPPCPAPEAAGGPSVFLFPPKPKDTLMISRTP EVTCVVVDVSHEDPEVKFNWYVDGVEVHNAKTKPREEQYNSTYRVVSVLTVLHQDWLNGKE YKCKVSNKALPAPIEKTISKAKGQPREPQVVTLPPSREEMTKNQVSLTCLVKGFYPSDIAVEWE SNGQPENNYKTTPPVLDSDGSFFLYSKLTVDKSRWQQGNVFSCSVMHEALHNHYTQKSLSL SPGK |
| 15 | DNA | hIgF1-Ea-Fc mut 13/2_E | acgctctgcggggctgagctgttggatgctgtcttcagttcgtcgtgtggagacagggcttttattcaacaagcccacagggtatgctc cagcagtcaggggcgcctcagacaagcactgtggatgagtgctgctccggagcctgatctaaggaggctggagatgtattgcg cacccctcaagcctgccgtccaggccagcaagaactcacacatgatctccccagaagaccccaccgtgccagcgctgaagcagt agagggagtgcagtcttccctccccccaaaacccaaggacaccccaaggaccaccatcctgatctccccgagtcactgctggtggac gtgagccacgaagaccctgaggtcaagttcaagtggtatgatggcgtggaggtgcataatgccaagacaaagccccgggga ggagcagtacaacagcacgtaccgtgtggtcagcgtcctcaccgtcctgcaccaggactggctgaatggcaaggagtacaagtg caaggtctccaacaaagccctcccagccccccatccgggaggagatgaccaagaaccaggtcagcctgacctgcctggtcaaag gcttctatcccagcgacat cgccgtggagtgggagagcaatgggcagccggagaacaactacaagaccacgcctcccgtgctggactccgacggctccttc ctctacagcaagctcaccgtggacaagagcaggtggcagcaggggaacgtcttctcatgctccgtgatgcatgaggctctgcacaa ccactacacgcagaagagcctctccctgtcccgggtaaa |
| 16 | DNA | hIgF1-Ea-Fc mut 13/2_A | acgctctgcggggctgagctgttggatgctgtcttcagttcgtcgtgtggagacagggcttttattcaacaagcccacagggtatgctc cagcagtcaggggcgcctcagacaagcactgtggatgagtgctgctccggagcctgtgatctaaggaggctggagatgtattgcg cacccctcaagcctgccgtccaggccagcaagaactcacacatgatctccccagaagaagtacatttgaagaacgcaagt ctgagggagtgcagcagtgctgcccaaaaacccaaggatgccccaccgtgcccagcacctgaagcagcggggaccgtcagtcttcct cttccccccaaaacccaaggacaccctcatgatctcccgacccctgaggtcacatgcgtggtggtggacgtgagccacgaagac |

| SEQ ID NO. | DNA/ PROT. | Description | Sequence |
|---|---|---|---|
| 17 | DNA | hIgF1-Ea-Fc mut 13/2_C | cctgaggtcaagttcaactggtacgtggacggcgtggaggtgcataatgccaagacaaagccgcgggaggagcagtacaacag cacgtaccgggtggtcagcgtcctcaccgtcctgcaccaggactggctgaatggcaaggagtacaagtgcaaggtctccaacaaa gcccctcccagcctatcgagaaaaccatctccaaagccaaagggcagccccgagaaccacaggtgtacaccctgcccccatc ccgggaggagatgaccaagaaccaggtcagcctgacctgcctggtcaaaggcttctatcccagcgacatcgccgtggagtgga gcaatgggcagccggagaacaactacaagaccacgcctcccgtgctggactccgacggctccttcttcctctacagcaagctca ccgtggacaagagcaggtggcagcaggggaacgtcttctcatgctccgtgatgcatgaggctctgcacaaccactacacgcag aagcctctccctgtctccgggtaaa |
| 18 | DNA | hIgF1-Ea-Fc mut 13/2_F | acgcttctgcgggctgagctgctgtgatgctcttcagttcgtcgtgtggagacaggggctttttattcaacaagccacagggtatggctc cagcagtcaggcggcgcctcagcctgcgtcgtggatgatgtcttccggagtcgtgatctaaggaagtacatttgaagacgcaagt cacccctccaagcctgcgtccagtgccagcgacatgccaagacaaagccgcggagtcaacaaggtgatatgacgccctcatga gggtgccacccctgaggtcacatgcgtggtggtggacgtgagccacgaagacccctgaggtcaagttcaactggtacgtggacggc gtggaggtgcataatgccaagacaaagccgcgggaggagcagtacaacagcacgtaccgtgtggtcagcgtcctcaccgtcctg caccaggactggctgaatggcaaggagtacaagtgcaaggtctccaacaaagcccttcctagccccatcgagaaaaccatctcc aaagcccaaaggtcagccccgagaaccacaggtgtacaccctgcccccatcccgggaggagatgaccaagaaccaggtcagc ctgacctgcctggtcaaaggcttctatcccagcgacatcgccgtggagtgggagagcaatgggcagccggagaacaactacaag accacgcctcccgtgctggactccgacggctccttcttcctctacagcaagctcaccgtggacaagagcaggtggcagcagggga acgtcttctcatgctccgtgatgcatgaggctctgcacaaccactacacgcagaagagcctctccctgtctc cgggtaaa |
| 19 | DNA | hIgF1-Ea-Fc mut 04/2_E | acgcttctgcggggctgagctgctgtgatgctcttcagttcgtcgtgtggagacaggggctttttattcaacaagccacagggtatggctc cagcagtcaggcggaggcctcagcctgcgtccagtccagcgacatgccaagacaaagccgcggagtcaacaaggtgatatgacgccctcatga gggacaaactcacacagcaaaaccctcactacagatgtgaccagatgcacaccctgaggtgacacacctggaggtcacatgcgtggtggtggac gtgagccacgaagacccctgaggtcaagttcaactggtacgtggacggcgtggaggtgcataatgccaagacaaagccgcggga ggagcagtacaacagcacgtaccgtgtggtcagcgtcctcaccgtcctgcaccaggactggctgaatggcaaggagtacaagtgt caaggtctccaacaaagcccttcctagccccatcgagaaaaccatctccaaagcccaaaggtcagccccgagaaccacaggtgt acaccctgccccatcccgggaggagatggccagcagagaccaagaaccaggtcagcctgacctgcctggtcaaaggcttctat cccagcgacatcgccgtggagtgggagaagcaatgggcagccggagaacaactacaagaccacgcctcccgtgctggactccgacggctccttcttcctctacagcaagctcaccgtggacaagagcaggtggcagcaggggaacgtcttctcatgctccgtgatgcatgaggctctgcacaa ccactacacgcagaagagcctctccctgtctccgggtaaa |
| 20 | DNA | hIgF1-Ea-Fc mut 04/2_A | acgcttctgcgggctgagctgctgtgatgctcttcagttcgtcgtgtggagacaggggctttttattcaacaagccacagggtatggctc cagcagtcaggcggagcgcctcagcctgcgtccagtgatgatgtcttccggagtcgtgatctaaggaagtacatttgaagacgcaagt caccccctccaagcctgcgtccagtgccagcgacatgccaagacaaagccgcgggagtcaacaaggtgatatgacgccacacaa |

| SEQ ID NO. | DNA/ PROT. | Description | Sequence |
|---|---|---|---|
| | | | agagggagtgcaggaacaagaactaccagatgtgcccaccgtgcccagcacctgaagcagcggggggaccgtcagtcttcct cttccccccaaaacccaaggacaccctcatgatctccggacccctgaggtcacatgcgtggtggtggacgtgagccacgaagac cctgaggtcaagttcaactggtacgtggacggcgtggaggtgcataatgccaagacaaagccgcgggaggagcagtacaacag cacgtaccgggtggtcagcgtcctcaccgtcctgcaccaggactggctgaatggcaaggagtacaagtgcaaggtctccaacaaa gccctcccagcccccatcgagaaaaccatctccaaagccaaagggcagccccgagaaccacaggtgtacaccctgcccccatc ccgggaggagatgaccaagaaccaggtcagcctgacctgcctggtcaaaggcttctatcccagcgacatcgccgtggagtgga gcaatgggcagccggagaacaactacaagaccacgcctcccgtgctggactccgacggctccttcttcctctacagcaagctca ccgtggacaagagcaggtggcagcaggggaacgtcttctcatgctccgtgatgcatgaggctctgcacaaccactacacgcagaa gagcctctccctgtctccgggtaaa |
| 21 | DNA | hIgF1-Ea-Fc mut 04/2_F | acgctctgcggggctgagctggtggatgctcttcagttcgtctgtgtggagacaggcgctttatttcaacaagcccacagggtatgctc cagcagctcggacgcctccagcaagcatcgtggatgagtccgagctgctggatgagtttcctaaggaggctgaagtgttattgcg cacccccaagcctgccgtcctcaggcccaagccgacatgccaagatgccaagacgcggggaccgtcagtcttccccccaaaaccc gggacacccctcatgatctccggacccctgaggtcacatgcgtggtggtggacgtgagccacgaagaccctgaggtcaagttca actggtacgtggacggcgtggaggtgcataatgccaagacaaagccgcgggaggagcagtacaacagcacgtaccgggtggtc agcgtcctcaccgtcctgcaccaggactggctgaatggcaaggagtacaagtgcaaggtctccaacaaagccctcccagccccc atcgagaaaaccatctccaaagccaaagggcagccccgagaaccacaggtgtacaccctgcccccatcccgggaggagatgac caagaaccaggtcagcctgacctgcctggtcaaaggcttctatcccagcgacatcgccgtggagtgggagagcaatgggcagcc ggagaacaactacaagaccacgcctcccgtgctggactccgacggctccttcttcctctacagcaagctcaccgtggacaagagca ggtggcagcaggggaacgtcttctcatgctccgtgatgcatgaggctctgcacaaccactacacgcagaagagcctctccctgtctc cgggtaaa |
| 22 | PROT. | hinge 1 | CPPCPA |
| 23 | PROT. | hinge 2 | DKTHTCPPCPA |
| 24 | PROT. | hinge 3 | EPKSCDKTHTCPPCPA |
| 25 | PROT. | mutated Ea-peptide 1 | VQAQQHTDMPKTQKEVHLKNASG |
| 26 | PROT. | mutated E-peptide | VQAQQHTDMPKTQKYQPPATNKNTKSQRRKGS |
| 27 | PROT. | hIgP1-Ea-mut 03 | GPTLCGAELVDALQFVCGDRGFYFNKPTGYGSSSRAAPQTGIVDECCFRSCDLRRLEMYCAP LKPAKSAVRAQRHTDMPKTQKEVHLKNASRGSAGNKNYRM |
| 28 | DNA | hIgP1-Ea-mut 03 | ggaccgacgctctgcggggctgagctggtggatgctcttcagttcgtgatgtcttcagttcgtgtgtggagacaggcgctttatttcaacaagcccacaggt atggctcccagcagtcgggcggcgcccagtcggcgcccagtcggcgcccagacaaggcatcgtggatgagtgctgcttccggagctgtgatctgcgg agactgctggaatgtactgcccccgctaaggcctgccaagtcagtgcagccagaccagacattgcccacaagacaggacattt tattgccaagtcccctgtcagtgcaagtagtgatgctgtgcccaccgacattgccagacccaagaccagaaggcctacagga tgcagaacgcaagtagaggagtgcaggaaaacaagaactacaggatg |
| 29 | PROT. | hIgP1-Ea-mut 02 | TLCGAELVDALQFVCGDRGFYFNKPTGYGSSSRAAPQTSIVDECCFRSCDLRRLEMYCAPLK PAKSAVOAQQHTDMPKTQKEVHLKNASRGSAGNKNYQMGSDKTHTCPPCPAPEAAGGPSV FLFPPKPKDTLMISRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQQGNVFSCSV MHEALHNHYTQKSLSLSPGK |

| SEQ ID NO. | DNA/ PROT. | Description | Sequence |
|---|---|---|---|
| 30 | PROT. | hIgF1-Ea-Fc_mut 04 | TLCGAELVDALQFVCGDRGFYFNKPTGYGSSSREAPQTGIVDECCFRSCDLRRLEMYCAPLK<br>PAKSAVQAQQHTDMPKTQKEVHLKNASRGSAGNKNYQMGSDKTHTCPPCPAPEAAGGPSV<br>FLFPPKPKDTLMISRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDKSRWQQGNVFSCSV<br>MHEALHNHYTQKSLSLSPGK |
| 31 | PROT. | hIgF1-Ea-Fc_mut 13 | TLCGAELVDALQFVCGDRGFYFNKPTGYGSSSQAAPQTGIVDECCFRSCDLRRLEMYCAPLK<br>PAKSAVQAQQHTDMPKTQKEVHLKNASRGSAGNKNYQMGSDKTHTCPPCPAPEAAGGPSV<br>FLFPPKPKDTLMISRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDKSRWQQGNVFSCSV<br>MHEALHNHYTQKSLSLSPGK |
| 32 | PROT. | Example 8 | TLCGAELVDALQFVCGDRGFYFNKPTGYGSSSRAPQTSIVDECCFRSCDLRRLEMYCAPLK<br>PAKSAVRAQRHTDMPKTQKEVHLKNASRGSAGNKNYRM |
| 33 | PROT. | Example 9 | TLCGAELVDALQFVCGDRGFYFNKPTGYGSSSREAPQTSIVDECCFRSCDLRRLEMYCAPLK<br>PAKSAVRAQRHTDMPKTQKEVHLKNASRGSAGNKNYRM |
| 34 | PROT. | Example 10 | TLCGAELVDALQFVCGDRGFYFNKPTGYGSSSRRAPQTSIVDECCFRSCDLRRLEMYCAPLK<br>PAKSAVRAQRHTDMPKTQKEVHLKNASRGSAGNKNYRM |
| 35 | PROT. | Example 11 | TLCGAELVDALQFVCGDRGFYFNKPTGYGSSSRPAPQTSIVDECCFRSCDLRRLEMYCAPLK<br>PAKSAVRAQRHTDMPKTQKEVHLKNASRGSAGNKNYRM |
| 36 | PROT. | Example 12 | TLCGAELVDALQFVCGDRGFYFNKPTGYGSSSQQAPQTSIVDECCFRSCDLRRLEMYCAPLK<br>PAKSAVRAQRHTDMPKTQKEVHLKNASRGSAGNKNYRM |
| 37 | PROT. | Example 13 | TLCGAELVDALQFVCGDRGFYFNKPTGYGSSSQAAPQTSIVDECCFRSCDLRRLEMYCAPLK<br>PAKSAVRAQRHTDMPKTQKEVHLKNASRGSAGNKNYRM |
| 38 | PROT. | Example 14 | TLCGAELVDALQFVCGDRGFYFNKPTGYGSSSQRAPQTSIVDECCFRSCDLRRLEMYCAPLK<br>PAKSAVQAQQHTDMPKTQKEVHLKNASRGSAGNKNYRM |
| 39 | PROT. | Example 15 | TLCGAELVDALQFVCGDRGFYFNKPTGYGSSSQRAPQTSIVDECCFRSCDLRRLEMYCAPLK<br>PAKSAVQAQQHTDMPKTQKEVHLKNASRGSAGNKNYRM |
| 40 | PROT. | Example 16 | TLCGAELVDALQFVCGDRGFYFNKPTGYGSSSQRAPQTSIVDECCFRSCDLRRLEMYCAPLK<br>PAKSAVQAQQHTDMPKTQKEVHLKNASRGSAGNKNYQM |
| 41 | PROT. | Example 17 | TLCGAELVDALQFVCGDRGFYFNKPTGYGSSSREAPQTSIVDECCFRSCDLRRLEMYCAPLK<br>PAKSAVRAQRHTDMPKTQKEVHLKNASRGSAGNKNYRM |
| 42 | PROT. | Example 18 | TLCGAELVDALQFVCGDRGFYFNKPTGYGSSSREAPQTSIVDECCFRSCDLRRLEMYCAPLK<br>PAKSAVQAQQHTDMPKTQKEVHLKNASRGSAGNKNYRM |

| SEQ ID NO. | DNA/PROT. | Description | Sequence |
|---|---|---|---|
| 43 | PROT. | Example 19 | TLCGAELVDALQFVCGDRGFYFNKPTGYGSSSREAPQTSIVDECCFRSCDLRRLEMYCAPLK PAKSAVQAQQHTDMPKTQKEVHLKNASRGSAGNKNYQM |
| 44 | PROT. | Example 20 | TLCGAELVDALQFVCGDRGFYFNKPTGYGSSSRAAPQTSIVDECCFRSCDLRRLEMYCAPLK PAKSAVQAQQHTDMPKTQKEVHLKNASRGSAGNKNYQM |
| 45 | PROT. | Example 21 | TLCGAELVDALQFVCGDRGFYFNKPTGYGSSSRAAPQTSIVDECCFRSCDLRRLEMYCAPLK PAKSAVQAQQHTDMPKTQKEVHLKNASRGSAGNKNYRM |
| 46 | PROT. | Example 22 | TLCGAELVDALQFVCGDRGFYFNKPTGYGSSSRAAPQTSIVDECCFRSCDLRRLEMYCAPLK PAKSAVQAQQHTDMPKTQKEVHLKNASRGSAGNKNYRM |
| 47 | PROT. | Example 23 | TLCGAELVDALQFVCGDRGFYFNKPTGYGSSSRPAPQTSIVDECCFRSCDLRRLEMYCAPLK PAKSAVQAQQHTDMPKTQKEVHLKNASRGSAGNKNYQM |
| 48 | PROT. | Example 24 | TLCGAELVDALQFVCGDRGFYFNKPTGYGSSSRPAPQTSIVDECCFRSCDLRRLEMYCAPLK PAKSAVQAQQHTDMPKTQKEVHLKNASRGSAGNKNYRM |
| 49 | PROT. | Example 25 | TLCGAELVDALQFVCGDRGFYFNKPTGYGSSSRPAPQTSIVDECCFRSCDLRRLEMYCAPLK PAKSAVQAQRHTDMPKTQKEVHLKNASRGSAGNKNYRM |
| 50 | PROT. | Example 26 | TLCGAELVDALQFVCGDRGFYFNKPTGYGSSSRPAPQTSIVDECCFRSCDLRRLEMYCAPLK PAKSAVQAQRHTDMPKTQKEVHLKNASRGSAGNKNYRM |
| 51 | PROT. | Example 27 | TLCGAELVDALQFVCGDRGFYFNKPTGYGSSSQQAPQTSIVDECCFRSCDLRRLEMYCAPLK PAKSAVQAQQHTDMPKTQKEVHLKNASRGSAGNKNYRM |
| 52 | PROT. | Example 28 | TLCGAELVDALQFVCGDRGFYFNKPTGYGSSSQQAPQTSIVDECCFRSCDLRRLEMYCAPLK PAKSAVQAQQHTDMPKTQKEVHLKNASRGSAGNKNYRM |
| 53 | PROT. | Example 29 | TLCGAELVDALQFVCGDRGFYFNKPTGYGSSSQAAPQTSIVDECCFRSCDLRRLEMYCAPLK PAKSAVQAQQHTDMPKTQKEVHLKNASRGSAGNKNYQM |
| 54 | PROT. | Example 30 | TLCGAELVDALQFVCGDRGFYFNKPTGYGSSSQAAPQTSIVDECCFRSCDLRRLEMYCAPLK PAKSAVQAQQHTDMPKTQKEVHLKNASRGSAGNKNYQM |
| 55 | PROT. | Example 31 | TLCGAELVDALQFVCGDRGFYFNKPTGYGSSSQRAPQTSIVDECCFRSCDLRRLEMYCAPLK PAVRAQRHTDMPKTQKEVHLKNASRGSAGNKNYRM |
| 56 | PROT. | Example 32 | TLCGAELVDALQFVCGDRGFYFNKPTGYGSSSREAPQTSIVDECCFRSCDLRRLEMYCAPLK PAVRAQRHTDMPKTQKEVHLKNASRGSAGNKNYRM |
| 57 | PROT. | Example 33 | TLCGAELVDALQFVCGDRGFYFNKPTGYGSSSRAAPQTSIVDECCFRSCDLRRLEMYCAPLK PAVRAQRHTDMPKTQKEVHLKNASRGSAGNKNYRM |
| 58 | PROT. | Example 34 | TLCGAELVDALQFVCGDRGFYFNKPTGYGSSSRPAPQTSIVDECCFRSCDLRRLEMYCAPLK PAVRAQRHTDMPKTQKEVHLKNASRGSAGNKNYRM |

| SEQ ID NO. | DNA/ PROT. | Description | Sequence |
|---|---|---|---|
| 59 | PROT. | Example 35 | TLCGAELVDALQFVCGDRGFYFNKPTGYGSSSQQAPQTSIVDECCFRSCDLRRLEMYCAPLK PAQVRAQRHTDMPKTQKEVHLKNASRGSAGNKNYRM |
| 60 | PROT. | Example 36 | TLCGAELVDALQFVCGDRGFYFNKPTGYGSSSQAAPQTSIVDECCFRSCDLRRLEMYCAPLK PAVRAQRHTDMPKTQKEVHLKNASRGSAGNKNYRM |
| 61 | PROT. | Example 37 | TLCGAELVDALQFVCGDRGFYFNKPTGYGSSSQRAPQTSIVDECCFRSCDLRRLEMYCAPLK PAVQAQHTDMPKTQKEVHLKNASRGSAGNKNYRM |
| 62 | PROT. | Example 38 | TLCGAELVDALQFVCGDRGFYFNKPTGYGSSSQRAPQTSIVDECCFRSCDLRRLEMYCAPLK PAVQAQRHTDMPKTQKEVHLKNASRGSAGNKNYRM |
| 63 | PROT. | Example 39 | TLCGAELVDALQFVCGDRGFYFNKPTGYGSSSQRAPQTSIVDECCFRSCDLRRLEMYCAPLK PAVQAQHTDMPKTQKEVHLKNASRGSAGNKNYQM |
| 64 | PROT. | Example 40 | TLCGAELVDALQFVCGDRGFYFNKPTGYGSSSREAPQTSIVDECCFRSCDLRRLEMYCAPLK PAVQAQRHTDMPKTQKEVHLKNASRGSAGNKNYRM |
| 65 | PROT. | Example 41 | TLCGAELVDALQFVCGDRGFYFNKPTGYGSSSREAPQTSIVDECCFRSCDLRRLEMYCAPLK PAVQAQHTDMPKTQKEVHLKNASRGSAGNKNYQM |
| 66 | PROT. | Example 42 | TLCGAELVDALQFVCGDRGFYFNKPTGYGSSSREAPQTSIVDECCFRSCDLRRLEMYCAPLK PAVQAQHTDMPKTQKEVHLKNASRGSAGNKNYRM |
| 67 | PROT. | Example 43 | TLCGAELVDALQFVCGDRGFYFNKPTGYGSSSRAAPQTSIVDECCFRSCDLRRLEMYCAPLK PAVQAQRHTDMPKTQKEVHLKNASRGSAGNKNYRM |
| 68 | PROT. | Example 44 | TLCGAELVDALQFVCGDRGFYFNKPTGYGSSSRAAPQTSIVDECCFRSCDLRRLEMYCAPLK PAVQAQHTDMPKTQKEVHLKNASRGSAGNKNYRM |
| 69 | PROT. | Example 45 | TLCGAELVDALQFVCGDRGFYFNKPTGYGSSSRAAPQTSIVDECCFRSCDLRRLEMYCAPLK PAVQAQHTDMPKTQKEVHLKNASRGSAGNKNYQM |
| 70 | PROT. | Example 46 | TLCGAELVDALQFVCGDRGFYFNKPTGYGSSSRPAPQTSIVDECCFRSCDLRRLEMYCAPLK PAVQAQRHTDMPKTQKEVHLKNASRGSAGNKNYQM |
| 71 | PROT. | Example 47 | TLCGAELVDALQFVCGDRGFYFNKPTGYGSSSRPAPQTSIVDECCFRSCDLRRLEMYCAPLK PAVQAQHTDMPKTQKEVHLKNASRGSAGNKNYRM |
| 72 | PROT. | Example 48 | TLCGAELVDALQFVCGDRGFYFNKPTGYGSSSRPAPQTSIVDECCFRSCDLRRLEMYCAPLK PAVQAQHTDMPKTQKEVHLKNASRGSAGNKNYQM |
| 73 | PROT. | Example 49 | TLCGAELVDALQFVCGDRGFYFNKPTGYGSSSQQAPQTSIVDECCFRSCDLRRLEMYCAPLK PAVQAQHTDMPKTQKEVHLKNASRGSAGNKNYRM |
| 74 | PROT. | Example 50 | TLCGAELVDALQFVCGDRGFYFNKPTGYGSSSQQAPQTSIVDECCFRSCDLRRLEMYCAPLK PAVQAQHTDMPKTQKEVHLKNASRGSAGNKNYRM |

| SEQ ID NO. | DNA/ PROT. | Description | Sequence |
|---|---|---|---|
| 75 | PROT. | Example 51 | TLCGAELVDALQFVCGDRGFYFNKPTGYGSSSQAAPQTSIVDECCFRSCDLRRLEMYCAPLK PAVQAQQHTDMPKTQKEVHLKNASRGSAGNKNYRM |
| 76 | PROT. | Example 52 | TLCGAELVDALQFVCGDRGFYFNKPTGYGSSSQQAPQTSIVDECCFRSCDLRRLEMYCAPLK PAVQAQQHTDMPKTQKEVHLKNASRGSAGNKNYQM |
| 77 | PROT. | Example 53 | TLCGAELVDALQFVCGDRGFYFNKPTGYGSSSQAAPQTSIVDECCFRSCDLRRLEMYCAPLK PAVQAQQHTDMPKTQKEVHLKNASRGSAGNKNYQM |
| 78 | PROT. | hIGF1-Ea-D1-3, R36Q, D68-72, R74Q, R77Q, R104Q-fc domain | TLCGAELVDALQFVCGDRGFYFNKPTGYGSSSQAAPQTGIVDECCFRSCDLRRLEMYCAPLK PAVQAQQHTDMPKTQKEVHLKNASRGSAGNKNYQM |
| 79 | PROT. | hIGF1-Ea-D1-3, R36Q, G42A, D68-72, R74Q, R77Q, R104Q-fc domain | TLCGAELVDALQFVCGDRGFYFNKPTGYGSSSQAAPQTAIVDECCFRSCDLRRLEMYCAPLK PAVQAQQHTDMPKTQKEVHLKNASRGSAGNKNYQM |
| 80 | PROT. | hIGF1-Ea-D1-3, R36Q, G42Q, D68-72, R74Q, R77Q, R104Q-fc domain | TLCGAELVDALQFVCGDRGFYFNKPTGYGSSSQAAPQTQIVDECCFRSCDLRRLEMYCAPLK PAVQAQQHTDMPKTQKEVHLKNASRGSAGNKNYQM |
| 81 | PROT. | hIGF1-Ea-D1-3, R36Q, G42P, D68-72, R74Q, R77Q, R104Q-fc domain | TLCGAELVDALQFVCGDRGFYFNKPTGYGSSSQAAPQTPIVDECCFRSCDLRRLEMYCAPLK PAVQAQQHTDMPKTQKEVHLKNASRGSAGNKNYQM |
| 82 | PROT. | hIGF1-Ea-D1-3, R36Q, G42K, D68-72, R74Q, R77Q, R104Q-fc domain | TLCGAELVDALQFVCGDRGFYFNKPTGYGSSSQAAPQTKIVDECCFRSCDLRRLEMYCAPLK PAVQAQQHTDMPKTQKEVHLKNASRGSAGNKNYQM |
| 83 | PROT. | hIGF1-Ea-D1-3, R36Q, G42E, D68- | TLCGAELVDALQFVCGDRGFYFNKPTGYGSSSQAAPQTEIVDECCFRSCDLRRLEMYCAPLK PAVQAQQHTDMPKTQKEVHLKNASRGSAGNKNYQM |

-continued

| SEQ ID NO. | DNA/ PROT. | Description | Sequence |
|---|---|---|---|
| | | 72, R74Q, R77Q, R104Q-fc domain | |
| 84 | PROT. | hIGF1-Ea-D1-3, R36Q, G42I, D68-72, R74Q, R77Q, R104Q-fc domain | TLCGAELVDALQFVCGDRGFYFNKPTGYGSSSQAAPQTIIVDECCFRSCDLRRLEMYCAPLKP AVQAQQHTDMPKTQKEVHLKNASRGSAGNKNYQM |
| 85 | PROT. | hIGF1-Ea-D1-3, R36Q, G42Y, D68-72, R74Q, R77Q, R104Q-fc domain | TLCGAELVDALQFVCGDRGFYFNKPTGYGSSSQAAPQTYIVDECCFRSCDLRRLEMYCAPLK PAVQAQQHTDMPKTQKEVHLKNASRGSAGNKNYQM |
| 86 | PROT. | hIGF1-Ea-D1-3, R36Q, D42, D68-72, R74Q, R77Q, R104Q-fc domain | TLCGAELVDALQFVCGDRGFYFNKPTGYGSSSQAAPQTIVDECCFRSCDLRRLEMYCAPLKP AVQAQQHTDMPKTQKEVHLKNASRGSAGNKNYQM |
| 87 | PROT. | hIGF1-Ea (delGPE, R37A) | TLCGAELVDALQFVCGDRGFYFNKPTGYGSSSRAAPQTGIVDECCFRSCDLRRLEMYCAPLK PAKSARSVRAQRHTDMPKTQKEVHLKNASRGSAGNKNYRM |
| 88 | DNA | hIGF1-Ea-hFc_mut2 forward primer | TGACACTATAGAATAACATCCACTTTGCC |
| 89 | DNA | hIGF1-Ea-hFc_mut2 reverse primer | TCACAGCTCCGAAGCAGCACTCATCCACGATGCTTGTCTGAGGCGCCGCCC |
| 90 | DNA | hIGF1-Ea-hFc_mut3 forward primer | TGACACTATAGAATAACATCCACTTTGCC |
| 91 | DNA | hIGF1-Ea-hFc_mut3 reverse primer | TCACAGCTCCGAAGCAGCACTCATCCACGATGGGTGTCTGAGGCGCCGCCC |
| 92 | DNA | hIGF1-Ea-hFc_mut4 forward primer | TGACACTATAGAATAACATCCACTTTGCC |

| SEQ ID NO. | DNA/ PROT. | Description | Sequence |
|---|---|---|---|
| 93 | DNA | hIGF1-Ea-hFc_mut4 reverse primer | TCACAGCTCCGAAGCAGCACTCATCCACGATGCCTGTCTGAGGCGMNNCCGACTGCTGGAGCCATACCCTGTGG |
| 94 | DNA | hIGF1-Ea-hFc_mut12 forward primer | TGACACTTATAGAATAACATCCACTTTGCC |
| 95 | DNA | hIGF1-Ea-hFc_mut12 reverse primer | TGTCTGAGGCGCCCGCACTGCTGGAGCCATACCCTGTGGGC |
| 96 | DNA | hIGF1-Ea-hFc_mut13 forward primer | TGACACTTATAGAATAACATCCACTTTGCC |
| 97 | DNA | hIGF1-Ea-hFc_mut13 reverse primer | TGTCTGAGGCGCCCTGACTGCTGGAGCCATACCCTGTGG |
| 98 | DNA | G42 mutation primer | CGGTACGTGCTGGCGTACTGCTCCTCCGCGGCTTTG |
| 99 | DNA | CHOK1 derivative knock out clone 1: copy A2 | AGCGTGCACCGAGAACAACGAATGCTGCCACCCAGAGTGCCTAGGCAGCTGCCATACAC CTGACGACAACAACCTGTGCCTGCCGGACACTACTACAAAGGCGTGTGTGTGC CTGCCTGCCACCTGGCACTTACAG(Aag)GTTCGAGGGCTGTGTGACCGCGATTTC TGCGCCAACATCCCAACGCTGAGAGCAGTGACTGACTTCATCCGCAACACGTCAGTGCT GAGTGCATGCAAGAATGTCCCTCAGGCTTCATCCGCAACGCACCCAGAGGTCAGTGG CGAGTGCATGCAAGAATGTCCCTCAGGCTTCATCCGCAACGCACCCAGAGGTCAGTGG CTCTTGTTCCCCATCCAGGAGGTGAATCTTGTTCATATTCCATGATTGTAGGAACCACCCA GAGGTTCATCCAG |
| 100 | DNA | CHOK1 derivative knock out clone 2: copy A5 | AGCGTGCACCGAGAACAACGAATGCTGCCACCCAGAGTGCCTAGGCAGCTGCCATACAC CTGACGACAACAACCTGTGCCTGCCGACACTACTACAAAGGCGTGTGTGTGC CTGCCTGCCACCTGGCACTTACAG(Agttcg)AGGGCTGGCGTGTGGACCGCGATTTC TGCGCCAACATCCCAACGCTGAGAGCAGTGACTGACTTCATCCGCAACACGTCAGTGCT CTGTGCATGCAAGAATGTCCCTCAGGCTTCATCCGCAACGCACCCAGAGGTCAGTGGCT CTTGTTCCCCATCCAGGAGGTGAATCTTGTTCATATTCCATGATTGTAGGAACCACCAGA GGTTCATCCAG |
| 101 | DNA | CHOK1 derivative knock out clone 3: copy A2 | AGCGTGCACCGAGAACAACGAATGCTGCCACCCAGAGTGCCTAGGCAGCTGCCATACAC CTGACGACAACAACCTGTGCCTGCCGACACTACTACAAAGGCGTGTGTGTGC CTGCCTGCCACCTGGCACTTACAG(Aag)GTTCGAGGGCTGTGTGACCGCGATTTC CTGCGCCAACATCCCAACGCTGAGAGCAGTGACTGACTTCATCCGCAACACGTCAGTGG CGAGTGCATGCAAGAATGTCCCTCAGGCTTCATCCGCAACGCACCCAGAGGTCAGTGG CTCTTGTTCCCCATCCAGGAGGTGAATCTTGTTCATATTCCATGATTGTAGGAACCACCCA GAGGTTCATCCAG |
| 102 | DNA | CHOK1 derivative | AGCGTGCACCGAGAACAACGAATGCTGCCACCCAGAGTGCCTAGGCAGCTGCCATACAC CTGACGACAACAACCTGTGCCTGCCGACACTACTACAAAGGCGTGTGTGTGC |

| SEQ ID NO. | DNA/ PROT. | Description | Sequence |
|---|---|---|---|
| | | knock out clone 2: copy Δ22 | CTGCCTGCCACCTGC(Aacctacaggttcgagggctgc)GCTGTGTGACCGCGATTTCTGCGC<br>CAACATCCCAACGCTGAGACAGTGACTCAGATGGCTTTGTCATCCACGATGGCAGTG<br>CATGCAAGAAATGTCCCTGCAGGCTTCATCCGCAACAGCAGTGACTCAGAGTGGCTCTTGT<br>TCCCCATCCAGGAGGTGAATCTTGTTCATATTCCATGATTGTAGGAACCACCCAGAGGTTC<br>ATCCAG |
| 103 | DNA | CHOK1 derivative knock out clone 1: copy 14 nucleotides replaced and 18 added | AGCGTGCACCGAGAACAACGAATGCTGCCACCCAGAGTGCCTAGGCAGCTGCCATACAC<br>CTGACGACAACAACCTGTGGCCTGCCGACACTACTACAAAGGCGTGTGTGC<br>CTGCCTGCCCCTGGtgaggtataggacagtattatagagagtggggcAGGGCTGGCGCTGTGTGACC<br>GCGATTTCTGCGCCAACATCCCAACGCTGAGAGCAGTGACTCAGATGGCTTTGTCATCC<br>ACGATGGCGAGTGCATGCAAGAATGTCCCTCAGGCTTCATCCGCAACAGCACCAGAGG<br>TCAGTGGCTCTTGTTCCCCATCCAGGAGGTGAATCTTGTTCATATTCCATGATTGTAGGAA<br>CCACCCAGAGGTTCATCCAG |
| 104 | DNA | CHOK1 derivative knock out clone 3: copy Δ114 | AGCGTGCACCGAGAACAACGAATGCTGCCACCCAGAGTGC(Actaggcagctgccatacacctgacga<br>caacacaacctgtgtggcctgccgacactactactacaaaggcgtgtgtgcctgcctgcccactggcacctacaggttcgaggg<br>c)TGGCCCTGTGTGGACCGCGATTTCTGCGCCAACATCCCAACGCTGAGACAGTGACT<br>CAGATGGCTTTGTCATCCACGATGGCGAGTGCATGCAAGAATGTCCCTCAGGCTTCATCC<br>GCAACAGCACCAGAGGTCAGTGGCTCTTGTTCCCCATCCAGGAGGTGAATCTTGTTCAT<br>ATTCCATGATTGTAGGAACCACCCAGAGGTTCATCCAG |
| 105 | DNA | CHO-DUXB11 derivative knock out clone: sequence Δ22 | AGCGTGCACCGAGAACAACGAATGCTGCCACCCAGAGTGCCTAGGCAGCTGCCATACAC<br>CTGACGACAACAACCTGTGTGGCCTGCCGACACTACTACAAAGGCGTGTGTGC<br>CTGCCTGCCCCTGG(Acacctacaggttcgagggctgg)CGCTGTGTGACCGCGATTTCTGCGC<br>CAACATCCCAACGCTGAGAGCAGTGACTCAGATGGCTTTGTCATCCACGATGGCAGTG<br>CATGCAAGAATGTCCCTCAGGCTTCATCCGCAACAGCACCAGAGGTCAGTGGCTCTTGT<br>TCCCCATCCAGGAGGTGAATCTTGTTCATATTCCATGATTGTAGGAACCACCCAGAGGTTC<br>ATCCAG |
| 106 | DNA | CHO-DUXB11 derivative knock out clone: sequence Δ7 | AGCGTGCACCGAGAACAACGAATGCTGCCACCCAGAGTGCCTAGGCAGCTGCCATACAC<br>CTGACGACAACAACCTGTGGCCTGCCGACACTACTACAAAGGCGTGTGTGC<br>CTGCCTGCCCCAACAACCTGCCACCTACA(Aggttcga)GGGCTGGCGCTGTGTGACCGCGATTTCT<br>GCGCCAACATCCCAACGCTGAGAGCAGTGACTCAGATGGCTTTGTCATCCACGATGGC<br>GAGTGCATGCAAGAATGTCCCTCAGGCTTCATCCGCAACAGCACCCAGAGGTCAGTGGCT<br>CTTGTTCCCCATCCAGGAGGTGAATCTTGTTCATATTCCATGATTGTAGGAACCACCCAGA<br>GGTTCATCCAG |

| SEQ ID NO. | DNA/ PROT. | Description | Sequence |
|---|---|---|---|
| 107 | DNA | CHO IGF1R zinc finger nuclease recognition sites and cutting site | CCCACCTGGCACCTACAGGT/TCGAGGGCTGGCGCTGTGTGG |
| 108 | DNA | CHO IGF1R forward sequencing primer (in intron 2-3) | CTAGCCTGTCTCTGGGACAC |
| 109 | DNA | CHO IGF1R reverse sequencing primer (in intron 3-4) | CTGGATGAACCTCTGGGTGG |
| 110 | DNA | CHO IGF1R exon 3 | TGTGCCCAAGTGTGTGCGGAAAGCGAGCGTGCACCGAGAACAACGAATGCTGCCACCCA GAGTGCCTAGGCAGTGTGCCATACACCTGACGACAACACCTGTGTGGCCTGCCGACA CTACTACTACAAAGGCGTGTGTGTCCTGCCTGCCTGGCCACCTACAGGT/TCGAGG GCTGGCGCTGTGTGGACCGCGATTTCTGCGCCAACATCCCCAACCTGAGACCAGTGAC TCAGATGGCTTTGTCATCCACGATGCAGTGCATGCAAGAATGTCCCTCAGGCTTCATC CGCAACAGCACCCAGAG |
| 111 | DNA | CHO IGF1R exon 3 and flanking introns | AAACTTAACGCGCACATCCCATAGCAAACCATTTCATAAGAAGGACTTGGCATGTGTTGTG TCCTTTCCCAGTGTGGGCTTCACAGATGGTATTACCTGTGCAGATTTCAGAGAAGTGTGT TTTTCCTAGCCTGTCTCTGGGACACCATTTAGTGCTGGTTGTGGCAGCAGATGACCCTGG GGAGGCTGTGTAGTCTCTTCATCTCACCACCTCTCCCCCTGTTCCCACAGTGCCCAA GTGTGTGCGGAAAGCGAGCGTGCACCGAGAACAACACCTGTGTGGCCTGCCGACACTA GGCAGCTGCCATACACCTGACGACAACACAACCTGTGTGGCCTGCCGACACTACTACTAC AAAGGCGTGTGTGTCCTGCCTGCCCACCTGGCCACCTACAGGT/TCGAGGGCTGGCGCT GTGTGGACCGCGATTTCTGCGCCAACATCCCCAACCTGAGAGCAGTGACTCAGATGGC |

| SEQ ID NO. | DNA/ PROT. | Description | Sequence |
|---|---|---|---|
| | | | TTTGTCATCCACGATGGCGACTGCATGCAAGAATGTCCCTCAGGCTTCATCCGCAACAGC<br>ACCCAGAGGTCAGTGCCTCTTGTTCCCCATCCAGGAGGTGAATCTTGTTCATATTCCATGA<br>TTGTAGGAACCACCCCAGAGGTTCATCCAGGGGAGGCTGTTGGAGGGTGCTGACTAA<br>GCTTGTTTTTATGAGAATCTTGGAATGCCTGGTCTGTCTTCATTTCTTTGTTTGGCTTGCT<br>TTGTTGCTTTGAAAGTGCCTTGCCTAGCCCTAGAGAGGAAGAATTAGCCTGCTG |
| 112 | DNA | Kozak sequence | CCCGCCCGCCACC |
| 113 | Prot. | hIGF1-Ea-del1-3, R37A, del71-72, R74Q, R77Q, R104Q-fc | TLCGAELVDALQFVCGDRGFYFNKPTGYGSSSRAAPQTGIVDECCFRSCDLRRLEMYCAPLK<br>PAKSAVQAQQHTDMPKTQKEVHLKNASRGSAGNKNYQMGSDKTHTCPPCPAPEAAGGPSV<br>FLFPPKPKDTLMISRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDKSRWQQGNVFSCSV<br>MHEALHNHYTQKSLSLSPGK |
| 114 | Prot. | hIGF1-Ea-hFc_mut03 | TLCGAELVDALQFVCGDRGFYFNKPTGYGSSSRAAPQTIVDECCFRSCDLRRLEMYCAPLK<br>PAKSAVQAQQHTDMPKTQKEVHLKNASRGSAGNKNYQMGSDKTHTCPPCPAPEAAGGPSV<br>FLFPPKPKDTLMISRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDKSRWQQGNVFSCSV<br>MHEALHNHYTQKSLSLSPGK |
| 115 | PROT. | mutated Ea-peptide 1 | VQAQQHTDMPKTQKEVHLKNASRGSAGNKNYQM |
| 116 | PROT | hIGF1-Ea-hFc_mut 12 | TLCGAELVDALQFVCGDRGFYFNKPTGYGSSSARAPQTIVDECCFRSCDLRRLEMYCAPLK<br>PAKSAVQAQQHTDMPKTQKEVHLKNASRGSAGNKNYQMGSDKTHTCPPCPAPEAAGGPSV<br>FLFPPKPKDTLMISRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDKSRWQQGNVFSCSV<br>MHEALHNHYTQKSLSLSPGK |
| 117 | PROT | IGF-1 (G42S) | GPETLCGAELVDALQFVCGDRGFYFNKPTGYGSSSRRAPQTSIVDECCFRSCDLRRLEMYCA<br>PLKPAKSA |
| 118 | PROT | hIGF1-Ea-mut 03-G42S | GPTLCGAELVDALQFVCGDRGFYFNKPTGYGSSSRAAPQTSIVDECCFRSCDLRRLEMYCAP<br>LKPAKSAVRAQQHTDMPKTQKEVHLKNASRGSAGNKNYRM |

MODES FOR CARRYING OUT THE INVENTION

It will be understood that the invention has been described by way of example only and modifications may be made whilst remaining within the scope and spirit of the invention.

EXAMPLES

The herein disclosed recombinant IGF-1 variants have a wildtype protein like receptor affinity (FIG. 1), but show a better pharmacokinetic in vivo profile than wildtype IGF-1 (FIG. 7) and can be used to prevent muscle atrophy with less frequent dosing (FIG. 8). In contrast to some of the prior art IGF-1 variants, which stimulate insulin receptor (InsR) phosphorylation leading to the risk of hypoglycemia, the disclose human IGF-1 precursor proteins being mutated at position G42 (deletion or specific substitutions) show a wildtype like ability to stimulate insulin receptor (InsR) phosphorylation, which diminishes said hypoglycemia risk (FIG. 5/6/19). Furthermore, in contrast to the wildtype hIGF-1 or some prior art variants thereof, the herein disclosed IGF-1 variants can be produced at high titers and without degradation in mammalian cells systems, allowing an industrial scale production.

Part A

General Methodology

A1 Reagents

Recombinant human IGF-1 was from Novartis AG and recombinant human insulin was purchased from Promocell (#C-60212).

A2 Vector Construction

Several vector assemblies according to the teachings of the present invention are feasible. As the individual elements of the vector are known in the prior art, suitable vectors can be assembled e.g. by sequencing or amplification and appropriate cloning of the basic genetic elements and expression cassettes in the desired orientation. Respective cloning methods are state of the art and also the sequence of the genetic elements described above are described in the prior art. Subsequently, the generation of vector constructs is described by way of example. However, it is understood by those of skill in the art that several other embodiments and ways to obtain respective vectors are suitable and readily available. All mammalian expression vectors (e.g. pBW679) described in this section are based on the mammalian expression vectors described in WO2009080720. The example section of WO2009080720, particularly FIG. 1, table 1 and the example section II: vector constructions (page 21-31) are herein incorporated by reference.

De novo synthesis of hIGF1-Ea-deIGPE-R37A) (SEQ ID NO.: 87) was ordered at The Blue Heron Biotech flanked by a 5'Kozak (CCCGCCCGCCCACC) (SEQ IDs NO.:112) and 5'HindIII/BamHI and 3'EcoRI restriction sites was delivered in a Blue Heron pUC vector. Recloning into pcDNA3.1 vector (Invitrogen, Life Technologies) was completed by a ligation reaction with compatible 5' BamHI and 3'EcoRI cloning sites. Construct was fully sequence controlled using T7 and BGHA specific primers. Then site directed mutagenesis (Quick Change II site directed Mutagenesis Kit, Stratagene) was done to remove the two residues R71 and S72 using the previous construct hIGF1-Ea-deIGPE-R37A/pCDNA3.1. The resulting construct hIGF1-Ea-deIGPE-R37A-deIRS was used to reclone hIGF1-Ea (deIGPE, R37A, deIRS) into mammalian expression vector pRS5a (Novartis propriety vector, NPL000961). PRS5a is a mammalian expression vector under CMV promoter, polyadenylation site from the BGH gene (bovine growth hormone) and ampicillin resistance. hIGF1-Ea (deIGPE, R37A, deIRS)/pRS5a was archived as NPL009759 (Novartis propriety vector).

hIGF1-Ea (del GPE, R37A, del RS) was amplified from NPL009759. PCR product was digested by 5'HindIII/3'BamHI and cloned into pRS5a-hIgG1 LALA vector (NPL012935, Novartis propriety vector). Several rounds of site directed mutagenesis as described above were performed to deliver the plasmid for hIGF1-Ea (deIGPE, R37A, deIRS)-[R74Q-R78Q-R104Q] (NPL017580, Novartis propriety vector). This plasmid was used as basis for further clonings described below.

Plasmid of hIGF1-Ea-hFc_mut2:

A PCR fragment that contains the G42S mutations was amplified from NPL017580 using mutagenic oligos (5' TGACACTATAGAATAACATC CACTTTGCC 3') (SEQ ID NO.: 88) and (5' TCACAGCTCCGGAAGCAGCACT-CATCCACG ATGCTTGTCTGAGGCGCCGCCC 3') (SEQ ID NO.: 89). BlpI and BspEI endonuclease restriction sited were used for cloning the generated PCR fragment back into NPL017580.

Plasmid of hIGF1-Ea-hFc_mut3:

A PCR fragment that contains the G42P mutations was amplified from NPL017580 using mutagenic oligos (5' TGACACTATAGAATAACATCCA CTTTGCC 3') (SEQ ID NO.: 90) and (5' TCACAGCTCCGGAAGCAGCACT-CATCCACGAT GGGTGTCTGAGGCGCCGCCC 3') (SEQ ID NO.: 91). BlpI and BspEI endonuclease restriction sited were used for cloning the generated PCR fragment back into NPL017580.

Plasmid of hIGF1-Ea-hFc_mut4:

A PCR fragment that contains the A37E mutation was amplified from NPL017580 using mutagenic oligos (5' TGACACTATAGAATAACATCCA CTTTGCC 3') (SEQ ID NO.: 92) and (5' TCACAGCTCCGGAAGCAGCACT-CATCCACGAT GCCTGTCTGAGGCGCMNNCCGACT-GCTGGAGCCATACCCTGTGG) (SEQ ID NO.: 93). The wobble codon is given in IUPAC nomenclature, where M stands for the bases A or C and N stands for the bases A, C, G or T. The latter oligo would carry a wobble codon for position 37. BlpI and BspEI endonuclease restriction sited were used for cloning the generated PCR fragment back into NPL017580. A37E substitution was selected by sequencing.

Plasmid of hIGF1-Ea-hFc_mut12:

A PCR fragment that contains the R36A-A37R mutation was amplified from NPL017580 using mutagenic oligos (5' TGACACTATAGAATAAC AT CCACTTTGCC 3') (SEQ ID NO.: 94) and (5' TGTCTGAGGCGCCCGCGCACT-GCTGGA GCCATACCCTGTGGGC 3') (SEQ ID NO.: 95). BlpI and SfoI endonuclease restriction sited were used for cloning the generated PCR fragment back into NPL017580.

Plasmid of hIGF1-Ea-hFc_mut13:

A PCR fragment that contains the R36Q mutation was amplified from NPL017580 (Novartis propriety vector) using mutagenic oligos (5' TGACACTATAGAATAACATC-CACTTTGCC 3') (SEQ ID NO.: 96) and (5' TGTCTGAG-GCGCCGCCTGACTGCTG GAGCCATACCCTGTGG 3') (SEQ ID NO.: 97); BlpI and SfoI endonuclease restriction sited were used for cloning the generated PCR fragment back into NPL017580.

The variants hIGF1-Ea-hFc mut4 and mut13 were further modified to introduce a different linker (i.e. SEQ ID 22 and 23): linker sequences spanning from BspEI endonuclease restriction site (corresponding to residue IGF1 F49-R50) to AleI (in the Fc portion) were ordered at Geneart. Linkers were cloned by standard cut and paste to obtain plasmids for hIGF1-Ea-hFc_mut4_E, hIGF1-Ea-hFc_mut13_E and hIGF1-Ea-hFc_mut13_A. In a next step, the mutation G42S was introduced.

Plasmid of hIGF1-Ea-hFc_Mut4/2_E and hIGF1-Ea-hFc_Mut13/2_E:

A PCR fragment that contains the G42S mutations was amplified from plasmid of hIGF1-Ea-hFc_mut2 using oligos (5' TGACACTATAGAATAACATCCACTTTGCC 3') (SEQ ID No.: 88) and (5' CGGTACGTGC TGGCGTACTGCTC-CTCCCGCGGCTTTG 3') (SEQ ID No.: 98). BspEI and SfoI endonuclease restriction sites were used for cloning the generated PCR fragment into plasmids of hIGF1-Ea-hFc_mut4_E and hIGF1-Ea-hFc_mut13_E.

Plasmid of hIGF1-Ea-hFc_mut13/2_A:

A PCR fragments that contain G42S-R36Q mutations was amplified from the plasmid of hIGF1-Ea-hFc_mut13/2_E using oligos (5' TGACACTATAGAATAACATCCACTTT-GCC 3') (SEQ ID No.: 88) and (5' CGGTACGTGC TGGCGTACTGCTCCTCCCGCGGCTTTG 3') (SEQ ID No.: 98). BspEI and SfoI endonuclease restriction sites were used for cloning the generated PCR fragment into the plasmid of hIGF1-Ea-hFc_mut13_A.

A3 Production of Recombinant Protein

Small Scale Production:

Two different transfection methods, FuGene and polyethylenimine (PEI) based, were used to produce the IGF1-Fc variants.

100 ml of HEK 293F culture was transfected with (PEI) as follows: 100 µg of plasmid DNA in water were diluted in 7 ml of FreeStyle expression medium (GIBCO, Cat. 12338026) for 10 min at room temperature. 300 µg of PEI (from 1 mg/mL PEI stock) were diluted in 7 ml FreeStyle expression medium at room temperature. The DNA and PEI solutions were then mixed together and incubated for 15 min before adding to 36 ml of HEK 293F cell culture at a density of about $1.4 \times 10^6$ cells/mL in a 500 ml shake flask. The culture was incubated in a Kuehner-Shaker ISF1-X (Kuehner) set at 100 rpm, 6% CO2 and 37° C. for 6 days. IGF1-Fc variants were then purified from cleared cell culture supernatants by Protein A chromatography using HiTrap MabSelect Sure 1 ml column (GE Healthcare) on an AKTA Avant (GE Healthcare). After base-line washing with PBS, bound material was eluted with 50 mM citrate, pH 3.0, 150 mM NaCl and immediately neutralized.

100 ml of HEK 293F culture was transfected with FuGENE HD Transfection Reagent (Roche) as follows: 100 µg of plasmid DNA in water were diluted in 1 ml of FreeStyle expression medium (GIBCO, Cat. 12338026) kept at room temperature. 400 µl of FuGENE were added to the diluted DNA and the mixture was incubated for 15 min at room temperature. The 1.4 ml of DNA-FuGENE mixture was then added to 98.6 mL of HEK 293F (Invitrogen) cell culture in a 500 ml flask having a cell density of about $0.5 \times 10^6$ cells/mL. The culture was incubated in a Kuehner-Shaker ISF1-X (Kuehner) set at 100 rpm, 6% CO2 and 37° C. for 7 days. IGF1-Fc variants were then purified from cleared cell culture supernatants by Protein A chromatography using HiTrap MabSelect Sure 1 ml column (GE Healthcare) on an AKTA Avant (GE Healthcare). After base-line washing with PBS, bound material was eluted with 50 mM citrate, pH 3.0, 150 mM NaCl and immediately neutralized.

Mid-Scale Production:

9.5 L of HEK 293 culture was transfected with polyethylenimine (PEI) as follows: 10 mg of plasmid DNA in TE buffer was incubated in 250 mL room temperature OptiMEM1 medium [Gibco Cat. No #11058-021] for 5 minutes. 20 mg of Polyethylenimine PEI (from 1 mg/mL PEI stock) was added to 250 mL room temperature OptiMEM1 medium (Gibco Cat. no#11058-021). The DNA and PEI solutions were then mixed together and incubated for 15 minutes. The 500 mL of DNA-PEI mixture was then added to 9.5 L HEK culture at a density between $0.75 \times 106$ cells/mL and $1.25 \times 106$ cells/mL. Transfected cells were inoculated at 37° C. in a 20 L Wave Cellbag (GE Healthcare, # CB0020L10-03). The Cellbag was placed on a Wave System 20/50 EHT set at 25 rpm, 7o rocking angle, 7% CO2, 0.50 lpm air, and 37° C. Fc fusion constructs were captured from concentrated culture supernatants by Protein A chromatography. After base-line washing with PBS, bound material was eluted with 50 mM citrate, pH 2.7, 140 mM NaCl and immediately neutralized. The neutralized fraction was then concentrated by ultrafiltration and sized over Superdex 200 in PBS in order to remove some contaminating aggregates. Purity of the material was >95% as judged by both SDS-PAGE and LC-MS analysis.

A4 Assessing Aggregation Level by SEC-MALS

Protein A purified IGF-1-Fc variants were tested for aggregation level by size-exclusion chromatography coupled with multi-angle light scattering detector (SEC-MALS) measurements were performed on an Agilent 1200 HPLC system (Agilent Technologies) connected to a triangle light scattering detector (miniDAWN Treos, Wyatt Technology, Santa Barbara, Calif., USA). The concentration of the sample was followed online with a differential refractometer (Optilab rEX, Wyatt Technology) using a specific refractive index increment (dn/dc) value of 0.186 ml/g. Sample volumes of 50 ul were injected on a Superdex 200 10/300 GL column (GE Healthcare). The data were recorded and processed using the ASTRA V software (Wyatt Technology). To determine the detector delay volumes and normalization coefficients for the MALS detector, a BSA sample (Sigma, A8531) was used as reference. Neither despiking nor a band broadening correction was applied.

A5 Cell Culture

Human skeletal muscle (skMC) cells were obtained from Cambrex (#CC-2561). Human primary myoblasts were cultured in growth medium [SkGM containing 20% fetal bovine serum (FBS, #2-01F40-1, Amimed) and 0.1% gentamycin]. After 4-5 days (at 37° C., 5% CO2 and 95% humidity) cells were seeded in growth medium at a density of 150.000 cells/well and grown (at 37° C., 5% CO2 and 95% humidity). At day 3 after seeding skMC myoblasts were used for signaling experiments. NIH3T3-IGF-1R and NIH3T3-InsR were maintained in DMEM containing 10% FBS, 100 U/ml penicillin, and 100 µg/ml streptomycin. Primary cynomolgus myoblasts were isolated from the gastrocnemius of a *Macaca fascicularis*, cynomolgus monkey. Cells were cultured in SkBM containing 20% fetal bovine serum (FBS, #2-01F40-1, Amimed) and 0.1% gentamycin (Life Technologies, #15750-037). 3T3-L1 adipocytes and C2C12 cells were obtained from American Type Culture collection (ATCC-CL-173 and ATCC; #91031101, respectively). 3T3-L1 adipocytes were maintained in DMEM, High Glucose, 1.5 g/Liter NaHCO3 (ATTC #30-2002) and differentiation was initiated by addition of DMEM, containing 10% FCS, 1% penicillin/streptomycin, 0.5 mM IBMX, 1 µM dexamethasone. C2C12 myoblasts were differentiated at day 3 after seeding. To do so, cells were washed once with differentiation medium (DM) consisting of DMEM supplemented with 2% heat inactivated horse serum (HS; #US 14-403F, Cambrex), 1% penicillin/streptomycin and 1% glutamine and then incubated in DM for 72 hours at 37° C., 5% CO2 and 95% humidity.

A6 Biacore

The binding properties were characterized by SPR using a Biacore T200 instrument at 25° C. Three CM5 chips (GE, BR-1005-30) were prepared by applying the standard amine coupling procedure. Flow cell 1 was blank immobilized to serve as reference, whereas IGF-1 and hIGF-1-Ea-Fc-_mut_13/2_A were immobilized on the measuring flow cells 2 and 3. Immobilization levels were adapted to the individual interaction and ranged from 20-143 RU (IGF-1) and from 32-113 RU (hIGF-1-Ea-Fc_mut_13/2_A). Dilution series of rec. human IGF-1R (R&D Systems, 391-GR) were prepared in running buffer, 1x HBS-EP+ (Teknova, H8022) containing 30 mM citrate and 0.05% BSA, and injected on the chip at a flow rate of 50 µl/min. The analyte concentration ranges were adapted to the individual interaction and ranged from 1000-3.9 nM (IGF-1R). Ligands were regenerated by injecting gentle Ag/Ab elution buffer (Thermo Scientific, 21027) for 90 sec at 50 µl/min. Kinetic rate constants and KD were calculated by fitting double-referenced sensorgrams to a 1:1 binding model.

A7 ELISA

For analysis of IGF-1R phosphorylation cells plated onto 6-well plates were cultured in growth medium for 24 (NIH3T3-IGF-1R) or 72 hours (human and cynomolgus primary myoblasts). Cells were starved for 24 (NIH3T3-IGF-1R) or 4 (human and cynomolgus primary myoblasts) hours and then stimulated with the indicated peptides for 15 min at 37° C. Cells were lysed with PhosphoSafe buffer (Cell Signaling) containing various protease inhibitors and cleared by centrifugation at 14,000×g for 15 minutes at 4° C. and IGF-1R phosphorylation levels were analyzed by ELISA using DuoSet IC human phosphor-IGF-1R kit (R&D Systems).

For analysis of insulin receptor phosphorylation NIH3T3-InsR cells were plated at a density of $0.2 \times 10^6$ cells per well of a 6-well plate and were cultured in growth medium for 24 hours. Cells were starved for 18 hours in serum-free medium and then stimulated with different ligands at 37° C. for 10 minutes. Cells were lysed as described above and InsR phosphorylation levels were analyzed by ELISA using DuoSet IC human phosphor-InsR ELISA kit (R&D Systems).

A8 Glucose Uptake

To measure glucose uptake 3T3-L1 adipocytes and C2C12 mouse myotubes cell were seeded onto 24-well plates and cultured in serum-free DMEM for 4 hours. Serum-free DMEM was then replaced with KRP buffer (130 mM NaCl, 1.3 mM MgSO4, 1.3 mM CaCl, 5 mM KCl and 10 mM Na2HPO4) or HBS (140 mM NaCl, 2.5 mM MgSO4, 1.0 mM CaCl, 5 mM KCl and 10 mM Hepes) for 3T3-L1 adipocytes and C2C12, respectively. Cells were treated for 1 hour with the specified peptides at 37° C. Glucose uptake was measured by adding 0.4 (adipocytes) or 0.8 (C2C12) µCi of [3H] 2-deoxy-D-glucose and 0.1 (adipocytes) or 0.01 (C2C12) mM 2-deoxy-D-glucose for 10 (adipocytes) or 5 (C2C12) minutes at room temperature. Medium was aspirated and the assay was terminated by adding KRP or HBS buffer containing 1 µM cytochalasin B. Cells were then washed with ice-cold PBS and lysed using 0.2 M NaOH and radioactivity analyzed by scintillation counting (see FIGS. 5/6).

A9 Pharmacokinetic Profiles

Adult male rats (n=3/group) received an intravenous (i.v.) bolus or subcutaneous injection of hIGF-1-Ea-Fc_mut 13/2_A or hIGF-1-Ea-Fc_mut 04/2_E at 10 mg/kg or hIGF-1 (1 mg/kg). Serial blood specimens were collected at 2, 4, 8, 24, 48, 72, 96, 168 and 336 hours after administration of IGF-1 variants or 0.083, 0.25, 0.5, 2, 4, 8 and 24 hours after hIGF-1 administration. Serum concentrations of recombinant proteins were determined by ELISA.

A10 Effects of hIGF-1-Ea-Fc Mut 13/2 A Against Dexamethasone-Induced Muscular Atrophy.

Dexamethasone (Dex) was dissolved in PBS to achieve a dose of 0.075 mg/kg/day with the Alzet model 2ML2 for 28 days. Dex was combined in the minipumps with hIGF-1 at a dose of 3.8 mg/kg/day in group C. Dex treatment was combined with every other day subcutaneous treatment of hIGF1-Ea-Fc_13/2_A in groups D, E and F at doses of 3, 10 and 30 mg/kg, respectively. Pumps were filled with the solution and kept for several hours at 37° C. in PBS until surgical implantation. Rats were treated subcutaneously with Temgesic at a dose of 0.02 mg/kg with a volume of 1 mL/kg at least 30 minutes before surgery, and then the pumps filled with the solution indicated above were implanted subcutaneously into the back of the rats under anesthesia with isoflurane at a concentration of 3%. Temgesic was administered subcutaneously to the rats 24 h and 48 h after the surgery. Rats in groups A, B and C were treated with daily subcutaneous injection of PBS. Body weights were measured twice per week. Four weeks after the treatment rats were euthanized with CO2, and muscles were dissected and weighed.

Part B

Working Examples

A prior art molecule comprising an Ea-peptide, wherein the protein residues E3, R71 and S72 have been deleted and the R37 amino acid has been substituted by alanine (hIGF1-Ea-Fc-mut 3) (SEQ ID NO.: 27) has been produced and tested.

Example 1: Preparation of DNA Expression Vectors 1.1 A DNA expression vector encoding the hIGF-1-Ea precursor polypeptide containing the following modifications was constructed as described above: hIgF1-Ea-Fc_mut 13/2_A (including the Fc portion from hIgG1 carrying the effector function silencing mutation L234A L235A ("LALA") (SEQ ID No.: 9); wherein G1, P2, E3 are deleted, amino acid R36 is substituted by glutamine (Q), R37 is substituted by alanine and the amino acids K68, S69, A70, R71 and S72 are deleted and amino acids R74, R77 and R104 are mutated to glutamine (Q); and which is linked to an IgG1 LALA Fc region.

This results in the following secreted protein sequence:

```
                                        (SEQ ID NO.: 9)
TLCGAELVDALQFVCGDRGFYFNKPTGYGSSSQAAPQTSIVDECCFRSCD

LRRLEMYCAPLKPAVQAQQHTDMPKTQKEVHLKNASRGSAGNKNYQMCPP

CPAPEAAGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKAL

PAPIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCSVM

HEALHNHYTQKSLSLSPGK
```

1.2 A DNA expression vector encoding the hIGF-1-Ea precursor polypeptide comprising the following modifications was constructed as described in section A2 above:

hIgF1-Ea-Fc_mut 04/2_E (including the hIgG1 LALA Fc region): a human IGF-1 precursor protein, wherein G1, P2, E3 are deleted, amino acid R37 is substituted by glutamic acid (E) and the amino acids K68, S69, A70, R71 and S72 are deleted and amino acids R74, R77 and R104 are mutated to glutamine (Q); and which is linked to an IgG1 LALA Fc region.

This results in the following secreted protein sequence:

(SEQ ID NO.: 12)
TLCGAELVDALQFVCGDRGFYFNKPTGYGSSSREAPQTSIVDECCFRSCD

LRRLEMYCAPLKPAVQAQQHTDMPKTQKEVHLKNASRGSAGNKNYQMDKT

HTCPPCPAPEAAGGPSVFLFPPKPKDTLMISRTPEVTCVVVDVSHEDPEV

KFNWYVDGVEVHNAKTKPREEQYNSTYRVVSVLTVLHQDWLNGKEYKCKV

SNKALPAPIEKTISKAKGQPREPQVYTLPPSREEMTKNQVSLTCLVKGFY

PSDIAVEWESNGQPENNYKTTPPVLDSDGSFFLYSKLTVDKSRWQQGNVF

SCSVMHEALHNHYTQKSLSLSPGK

On the basis of the principles outlined above, the following additional proteins have been produced:

Example 54
    (hIgF1-Ea-Fc_mut 13/2_E; SEQ ID NO.: 8)

Example 56
    (hIgF1-Ea-Fc_mut 13/2_C; SEQ ID NO.: 10)

Example 50
    (hIgF1-Ea-Fc_mut 13/2_F; SEQ ID NO.: 11)

Example 58
    (hIgF1-Ea-Fc_mut 04/2_A; SEQ ID NO.: 13)

Example 59
    (hIgF1-Ea-Fc_mut 04/2_F; SEQ ID NO.: 14)

1.3 A DNA expression vector encoding the hIGF-1 polypeptide containing the following modifications was constructed using DNA vector construction/DNA manipulations methods known in the art: hIgF1 G42S (SEQ ID No.: 117);

This results in the following protein sequence:

(SEQ ID NO.: 117)
GPETLCGAELVDALQFVCGDRGFYFNKPTGYGSSSRRAPQTSIVDECCFR

SCDLRRLEMYCAPLKPAKSA 1.4 A DNA expression vector encoding the hIGF-1 polypeptide containing the following modifications was constructed using DNA vector construction/DNA manipulations methods known in the art: hIgF1-Ea-mut 03-G42S (SEQ ID No.: 118);

This results in the following protein sequence:

(SEQ ID NO.: 118)
GPTLCGAELVDALQFVCGDRGFYFNKPTGYGSSSRAAPQTSIVDECCFRS

CDLRRLEMYCAPLKPAKSAVRAQRHTDMPKTQKEVHLKNASRGSAGNKNY

RM

Example 2: Protease Challenge of IGF-1-Fc Variants

Proteins produced in mammalian cell expression systems, such as for example CHO, may suffer from proteolytic degradation during expression. To efficiently assess the potential protease susceptibility during production in a standardized way, we have developed a protease challenge assay using purified protein and conditioned media from CHO cell cultures. Comparison of that assay to cleavage pattern observed for an IGF-1-Fc variant produced in CHO cell provided an assay validation. In brief, CHO cells were cultivated (37° C., 6% CO2, 85% rel humidity, 90-150 rpm) in CHODM122 media from 2E5 cells/ml to a density of up to 1E7 cells/ml. The cleared supernatant provides the conditioned media used for the assay. IGF-1-Fc variants were purified as described above (A3) and spiked in at a concentration of 100 µg/ml in conditioned media or PBS as control. After sterile filtration, samples were incubated at 37° C. up to 20 days and samples to be analysed at various time points were taken. The different degradation products could be well isolated by standard SDS-PAGE techniques (NuPAGE Bis-Tris, Invitrogen) and the intensity of the degradation bands was quantified densitometrically. The results are shown in FIG. 17.

Example 3: High Affinity Binding of hIGF-1 and Analogues to Recombinant Human IGF-1R High affinity binding of hIGF-1 and IGF-1 variants to rhIGF1R was measured using surface plasmon resonance (Biacore). A direct binding assay was performed. Human IGF-1-Ea_Fc_Mut_13/2_A and hIGF-1 were immobilized on a chip and the IGF-1 receptor served as analyte in solution. The resulting sensorgrams were fitted to a 1:1 interaction model to calculate the equilibrium dissociation constants (KD). The results show that binding of hIGF-1-Ea_Fc_Mut_13/2_A to IGF-1R is comparable to hIGF-1 (FIG. 1).

Example 4: Induction of IGF-1R phosphorylation

The ability of hIGF-1 and hIGF-1 variants to stimulate phosphorylation of the IGF-1R was first evaluated in NIH3T3 cells overexpressing human IGF-1R (NIH3T3-IGF-1R) by ELISA. In these cells IGF-1R phosphorylation was induced in a concentration-dependent manner by all tested peptides. Logistic curve fitting of the averaged ELISA data showed that the potency ($EC_{50}$) of hIGF1-Ea-D1-3, R37A, D71-72, R77Q-Fc and hIGF1-Ea-Fc_mut_04/2_E was decreased compared hIGF-1 (FIG. 2A-B). However, logistic curve fitting of the averaged ELISA data yielded a very comparable maximal response value for all tested peptides (FIG. 2C-D). The ability of hIGF-1 variants and hIGF-1 to stimulate phosphorylation of endogenous IGF-1R was evaluated in primary human myoblasts and in cynomolgus myoblasts. In these cells IGF-1R phosphorylation was induced in a concentration-dependent manner by all tested peptides (FIG. 4B-C) Logistic curve fitting of the averaged ELISA data showed that the potency ($EC_{50}$) of hIGF-1 variants was E was decreased compared hIGF-1 (FIG. 4A). However, logistic curve fitting of the averaged ELISA data yielded a very comparable maximal response value for all tested peptides (FIG. 4).

Example 5: Specificity Versus Insulin Receptor

To test whether the amino acid modifications of IGF-1 variants affect receptor specificity, the effects of IGF-1 variant peptides on InsR phosphorylation were analyzed in NIH3T3 overexpressing the human InsR by ELISA. We treated NIH3T3-InsR cell transfectants with different concentrations of IGF-1 variants, hIGF-1 and insulin. Equimolar concentrations of the indicated peptides were used. The results of these experiments are shown in FIG. 3/18. Modifications did affect receptor specificity of most IGF-1 variants with the exception of variants bearing the G42S mutation (hIGF1-Ea-Fc_mut_02, hIGF1-Ea-Fc_mut_03, hIGF1-Ea-Fc_mut_04/2_E and hIGF1-Ea-Fc_mut_13/2_A) which were shown to maintain receptor specificity and be week inducers of InsR phosphorylation even at concentrations at which insulin would give maximal responses. Surprisingly, hIGF1-Ea Fc_mut_13/2_A and hIGF1-Ea Fc_mut_04/2_E were shown to be significantly less potent than IGF-1 on effector functions driven by rapid insulin receptor binding (e.g. glucose uptake in differentiated adipocytes) as shown in FIGS. 5B and D and in FIG. 6. In contrast, hIGF1-Ea Fc_mut_13/2_A and hIGF1-Ea Fc_mut_04/2_E and hIGF-1 were equipotent for IGF-1R-mediated functions such as glucose uptake in C2C12 myotubes (FIGS. 5A and C). Introduction of the G42S mutation into the IGF-1 protein (resulting in the IGF-1 G42S variant of SEQ ID NO.:117) as well as into the hIGF1-Ea-mut 03 protein (resulting in the hIGF1-Ea-mut 03-G42S variant of SEQ ID NO.:118) reduced the InsR phosphorylation (FIG. 18) in the NIH3T3-InsR cells. Furthermore, said mutations have an impact on the glucose uptake in adipocytes and C2C12 myotubes, respectively (FIG. 19)

Example 6: Determination of Serum Concentration

Serum concentrations of hIGF1-Ea-Fc-mut_13/2_A and hIGF1-Ea.Fc_mut_04/2_E after single i.v. and s.c. dose administration in male Fischer rats (n=3) was determined by ELISA specific for hIGF-1Ea 3mut (for details see A5 above). The results of these experiments are shown in FIGS. 7-A and 7-B. The terminal half-life is around 75.3 and 50.1 hours, respectively. The maximal concentration was reached after 8 and 24 hours (Tmax) of s.c. dose administration, respectively. In contrast, following intravenous administration of hIGF-1 (1.0 mg/kg), the levels of hIGF-1 were quantifiable over a time range of 0-8 hours. After Tmax (0.083 h) was reached a rapid decline of the serum concentration of the peptide was observed resulting in an apparent terminal half-life of 1.81 h. Following subcutaneous administration of hIGF-1 (1.0 mg/kg), serum levels were quantifiable up to 8 h post dosing and the maximal concentration was observed at 0.5 h post dose. Thus the IGF-1 analogs display a much improved pharmacokinetic profile compared to human IGF-1.

Example 7: Effects of hIGF-1-Ea-Fc_Mut_13/2_A Against Dexamethasone-Induced Muscular Atrophy Since IGF-1 has been shown to stimulate protein synthesis and inhibit protein degradation in skeletal muscle, we tested whether administration of hIGF-1-Ea_Fc_mut_13/2_A in dexamethasone-treated rats might prevent muscle atrophy. Male Wistar rats were continuously infused via Alzet pump with 75 µg of dexamethasone/kg/day either alone or together with vehicle (PBS), or hIGF-1. An additional group of animals infused with dexamethasone as described above received every other day s.c. injection of hIGF-1-Ea_Fc_mut_13/2_A. All animals were treated for twenty-eight days and then sacrificed. Body weight was monitored at the start of the experiment and then at day 28 post injection.

As expected significant reductions in body and muscle weight was observed in dexamethasone-treated rats as compared to vehicle control (FIG. 8). Injection of hIGF-1-Ea_Fc_mut_13/2_A significantly reduced the loss of body and muscle weight (FIG. 8).

In addition to the above described hIGF-1-Ea precursor polypeptides variants, the following additional protein variants can be produced and used in accordance with the invention:

Example 8

(2b) G1, P2, E3 are deleted, amino acid R36 is substituted by glutamine (Q), G42 is substituted by serin and the amino acids R71 and S72 are deleted.

```
                                        (SEQ ID NO: 32)
tlcgaelvdalqfvcgdrgfyfnkptgygsssqrpapqtsivdeccfrsc dlrrlemycaplkpaksavraqrhtdmpktqkevhlknasrgsagnknyr m.
```

Example 9

(4b) G1, P2, E3 are deleted, amino acid R37 is substituted by glutamic acid (E), G42 is substituted by serin and the amino acids R71 and S72 are deleted.

```
                                       (SEQ ID NO.: 33)
tlcgaelvdalqfvcgdrgfyfnkptgygsssreapqtsivdeccfrscd lrrlemycaplkpaksavraqrhtdmpktqkevhlknasrgsagnknyr m.
```

Example 10

(5b) G1, P2, E3 are deleted, amino acid R37 is substituted by alanine, G42 is substituted by serin and the amino acids R71 and S72 are deleted.

```
                                       (SEQ ID NO.: 34)
tlcgaelvdalqfvcgdrgfyfnkptgygsssraapqtsivdeccfrscd lrrlemycaplkpaksavraqrhtdmpktqkevhlknasrgsagnknyr m.
```

Example 11

(6b) G1, P2, E3 are deleted, amino acid R37 is substituted by proline (P), G42 is substituted by serin and the amino acids R71 and S72 are deleted.

```
                                       (SEQ ID NO.: 35)
tlcgaelvdalqfvcgdrgfyfnkptgygsssrpapqtsivdeccfrscd lrrlemycaplkpaksavraqrhtdmpktqkevhlknasrgsagnknyr m.
```

Example 12

(8b) G1, P2, E3 are deleted, amino acid R36 and R37 are both substituted by glutamine (Q), G42 is substituted by serin and the amino acids R71 and S72 are deleted. tlcgaelvdalqfvcgdrgfyfnkptgygsssqqapqtsivdeccfrscdlrrlemycaplkpaksavraqrhtdmpktqkevhlkn asrgsagnknyrm (SEQ ID NO.:36).

Example 13

(9b) G1, P2, E3 are deleted, amino acid R36 is substituted by glutamine (Q), R37 is substituted by alanine, G42 is substituted by serin and the amino acids R71 and S72 are deleted.

(SEQ ID NO.: 37)
tlcgaelvdalqfvcgdrgfyfnkptgygsssqaapqtsivdeccfrscd lrrlemycaplkpaksavraqrhtdmpktqkevhlknasrgsagnknyr m.

Example 14

(13b) G1, P2, E3 are deleted, amino acid R36 is substituted by glutamine (Q), G42 is substituted by serin, the amino acids R71 and S72 are deleted and amino acid R74 is mutated to glutamine (Q).

(SEQ ID NO.: 38)
tlcgaelvdalqfvcgdrgfyfnkptgygsssqrapqtsivdeccfrscd lrrlemycaplkpaksavqaqrhtdmpktqkevhlknasrgsagnknyr m.

Example 15

(14b) G1, P2, E3 are deleted, amino acid R36 is substituted by glutamine (Q), G42 is substituted by serin, the amino acids R71 and S72 are deleted and amino acids R74 and R77 are mutated to glutamine (Q).

(SEQ ID NO.: 39)
tlcgaelvdalqfvcgdrgfyfnkptgygsssqrapqtsivdeccfrscd lrrlemycaplkpaksavqaqqhtdmpktqkevhlknasrgsagnknyr m.

Example 16

(15b) G1, P2, E3 are deleted, amino acid R36 is substituted by glutamine (Q), G42 is substituted by serin, the amino acids R71 and S72 are deleted and amino acids R74, R77 and R104 are mutated to glutamine (Q).

(SEQ ID NO.: 40)
tlcgaelvdalqfvcgdrgfyfnkptgygsssqrapqtsivdeccfrscd lrrlemycaplkpaksavqaqqhtdmpktqkevhlknasrgsagnknyq m.

Example 17

(16b) G1, P2, E3 are deleted, amino acid R37 is substituted by glutamic acid (E), G42 is substituted by serin, the amino acids R71 and S72 are deleted and amino acid R77 is mutated to glutamine (Q).

(SEQ ID NO.: 41)
tlcgaelvdalqfvcgdrgfyfnkptgygsssreapqtsivdeccfrscd lrrlemycaplkpaksavraqqhtdmpktqkevhlknasrgsagnknyr m.

Example 18

(17b) G1, P2, E3 are deleted, amino acid R37 is substituted by glutamic acid (E), G42 is substituted by serin, the amino acids R71 and S72 are deleted and amino acids R74 and R77 are mutated to glutamine (Q).

(SEQ ID NO.: 42)
tlcgaelvdalqfvcgdrgfyfnkptgygsssreapqtsivdeccfrscd lrrlemycaplkpaksavqaqqhtdmpktqkevhlknasrgsagnknyr m.

Example 19

(18b) G1, P2, E3 are deleted, amino acid R37 is substituted by glutamic acid (E), G42 is substituted by serin, the amino acids R71 and S72 are deleted and amino acids R74, R77 and R104 are mutated to glutamine (Q).

(SEQ ID NO.: 43)
tlcgaelvdalqfvcgdrgfyfnkptgygsssreapqtsivdeccfrscd lrrlemycaplkpaksavqaqqhtdmpktqkevhlknasrgsagnknyq m.

Example 20

(19b) G1, P2, E3 are deleted, amino acid R37 is substituted by alanine (A), G42 is substituted by serin, the amino acids R71 and S72 are deleted and amino acid R74 is mutated to glutamine (Q).

(SEQ ID NO.: 44)
tlcgaelvdalqfvcgdrgfyfnkptgygsssraapqtsivdeccfrscd lrrlemycaplkpaksavqaqrhtdmpktqkevhlknasrgsagnknyr m.

Example 21

(20b) G1, P2, E3 are deleted, amino acid R37 is substituted by alanine (A), G42 is substituted by serin, the amino acids R71 and S72 are deleted and amino acids R74 and R77 are mutated to glutamine (Q).

```
                                        (SEQ ID NO.: 45)
tlcgaelvdalqfvcgdrgfyfnkptgygsssraapqtsivdeccfrscd
lrrlemycaplkpaksavqaqqhtdmpktqkevhlknasrgsagnknyr
m.
```

Example 22

(21b) G1, P2, E3 are deleted, amino acid R37 is substituted by alanine (A), G42 is substituted by serin, the amino acids R71 and S72 are deleted and amino acids R74, R77 and R104 are mutated to glutamine (Q).

```
                                        (SEQ ID NO.: 46)
tlcgaelvdalqfvcgdrgfyfnkptgygsssraapqtsivdeccfrscd
lrrlemycaplkpaksavqaqqhtdmpktqkevhlknasrgsagnknyq
m.
```

Example 23

(22b) G1, P2, E3 are deleted, amino acid R37 is substituted by proline (P), G42 is substituted by serin, the amino acids R71 and S72 are deleted and amino acid R74 is mutated to glutamine (Q).

```
                                        (SEQ ID NO.: 47)
tlcgaelvdalqfvcgdrgfyfnkptgygsssrpapqtsivdeccfrscd
lrrlemycaplkpaksavqaqrhtdmpktqkevhlknasrgsagnknyr
m.
```

Example 24

(23b) G1, P2, E3 are deleted, amino acid R37 is substituted by proline (P), G42 is substituted by serin, the amino acids R71 and S72 are deleted and amino acids R74 and R77 are mutated to glutamine (Q).

```
                                        (SEQ ID NO.: 48)
tlcgaelvdalqfvcgdrgfyfnkptgygsssrpapqtsivdeccfrscd
lrrlemycaplkpaksavqaqqhtdmpktqkevhlknasrgsagnknyr
m.
```

Example 25

(24b) G1, P2, E3 are deleted, amino acid R37 is substituted by proline (P), G42 is substituted by serin, the amino acids R71 and S72 are deleted and amino acids R74, R77 and R104 are mutated to glutamine (Q).

```
                                        (SEQ ID NO.: 49)
tlcgaelvdalqfvcgdrgfyfnkptgygsssrpapqtsivdeccfrscd
lrrlemycaplkpaksavqaqqhtdmpktqkevhlknasrgsagnknyq
m.
```

Example 26

(25b) G1, P2, E3 are deleted, amino acid R36 and R37 are both substituted by glutamine (Q), G42 is substituted by serin, the amino acids R71 and S72 are deleted and amino acid R74 is mutated to glutamine (Q).

```
                                        (SEQ ID NO.: 50)
tlcgaelvdalqfvcgdrgfyfnkptgygsssqqapqtsivdeccfrscd
lrrlemycaplkpaksavqaqrhtdmpktqkevhlknasrgsagnknyr
m.
```

Example 27

(26b) G1, P2, E3 are deleted, amino acid R36 and R37 are both substituted by glutamine (Q), G42 is substituted by serin, the amino acids R71 and S72 are deleted and amino acids R74 and R77 are mutated to glutamine (Q).

```
                                        (SEQ ID NO.: 51)
tlcgaelvdalqfvcgdrgfyfnkptgygsssqqapqtsivdeccfrscd
lrrlemycaplkpaksavqaqqhtdmpktqkevhlknasrgsagnknyr
m.
```

Example 28

(27b) G1, P2, E3 are deleted, amino acid R36 is substituted by glutamine (Q), R37 is substituted by alanine, G42 is substituted by serin, the amino acids R71 and S72 are deleted and amino acids R74 and R77 are mutated to glutamine (Q).

```
                                        (SEQ ID NO.: 52)
tlcgaelvdalqfvcgdrgfyfnkptgygsssqaapqtsivdeccfrscd
lrrlemycaplkpaksavqaqqhtdmpktqkevhlknasrgsagnknyr
m.
```

Example 29

(28b) G1, P2, E3 are deleted, amino acid R36 and R37 are both substituted by glutamine (Q), G42 is substituted by serin, the amino acids R71 and S72 are deleted and amino acids R74, R77 and R104 are mutated to glutamine (Q).

```
                                        (SEQ ID NO.: 53)
tlcgaelvdalqfvcgdrgfyfnkptgygsssqqapqtsivdeccfrscd
lrrlemycaplkpaksavqaqqhtdmpktqkevhlknasrgsagnknyq
m.
```

Example 30

(29b) G1, P2, E3 are deleted, amino acid R36 is substituted by glutamine (Q), R37 is substituted by alanine, G42 is substituted by serin, the amino acids R71 and S72 are deleted and amino acids R74, R77 and R104 are mutated to glutamine (Q).

(SEQ ID NO.: 54)
tlcgaelvdalqfvcgdrgfyfnkptgygsssqaapqtsivdeccfrscd
lrrlemycaplkpaksavqaqqhtdmpktqkevhlknasrgsagnknyq
m.

Example 31

(2c) G1, P2, E3 are deleted, amino acid R36 is substituted by glutamine (Q), G42 is substituted by serin, the amino acids K68, S69, A70, R71 and S72 are deleted.

(SEQ ID NO.: 55)
tlcgaelvdalqfvcgdrgfyfnkptgygsssqrapqtsivdeccfrscd
lrrlemycaplkpavraqrhtdmpktqkevhlknasrgsagnknyrm.

Example 32

(4c) G1, P2, E3 are deleted, amino acid R37 is substituted by glutamic acid (E), G42 is substituted by serin, the amino acids K68, S69, A70, R71 and S72 are deleted.

(SEQ ID NO.: 56)
tlcgaelvdalqfvcgdrgfyfnkptgygsssreapqtsivdeccfrscd
lrrlemycaplkpavraqrhtdmpktqkevhlknasrgsagnknyrm.

Example 33

(5c) G1, P2, E3 are deleted, amino acid R37 is substituted by alanine, G42 is substituted by serin, the amino acids K68, S69, A70, R71 and S72 are deleted.

(SEQ ID NO.: 57)
tlcgaelvdalqfvcgdrgfyfnkptgygsssraapqtsivdeccfrscd
lrrlemycaplkpavraqrhtdmpktqkevhlknasrgsagnknyrm.

Example 34

(6c) G1, P2, E3 are deleted, amino acid R37 is substituted by proline (P), G42 is substituted by serin, the amino acids K68, S69, A70, R71 and S72 are deleted.

(SEQ ID NO.: 58)
tlcgaelvdalqfvcgdrgfyfnkptgygsssrpapqtsivdeccfrscd
lrrlemycaplkpavraqrhtdmpktqkevhlknasrgsagnknyrm.

Example 35

(8c) G1, P2, E3 are deleted, amino acid R36 and R37 are both substituted by glutamine (Q), G42 is substituted by serin and the amino acids K68, S69, A70, R71 and S72 are deleted.

(SEQ ID NO.: 59)
tlcgaelvdalqfvcgdrgfyfnkptgygsssqqapqtsivdeccfrscd
lrrlemycaplkpaqvraqrhtdmpktqkevhlknasrgsagnknyrm.

Example 36

(9c) G1, P2, E3 are deleted, amino acid R36 is substituted by glutamine (Q), R37 is substituted by alanine, G42 is substituted by serin, the amino acids K68, S69, A70, R71 and S72 are deleted.

(SEQ ID NO.: 60)
tlcgaelvdalqfvcgdrgfyfnkptgygsssqaapqtsivdeccfrscd
lrrlemycaplkpavraqrhtdmpktqkevhlknasrgsagnknyrm.

Example 37

(13c) G1, P2, E3 are deleted, amino acid R36 is substituted by glutamine (Q), G42 is substituted by serin and the amino acids K68, S69, A70, R71 and S72 are deleted and amino acid R74 is mutated to glutamine (Q).

(SEQ ID NO.: 61)
tlcgaelvdalqfvcgdrgfyfnkptgygsssqrapqtsivdeccfrscd
lrrlemycaplkpavqaqrhtdmpktqkevhlknasrgsagnknyrm.

Example 38

(14c) G1, P2, E3 are deleted, amino acid R36 is substituted by glutamine (Q), G42 is substituted by serin and the amino acids K68, S69, A70, R71 and S72 are deleted and amino acid R74 and R77 are mutated to glutamine (Q).

(SEQ ID NO.: 62)
tlcgaelvdalqfvcgdrgfyfnkptgygsssqrapqtsivdeccfrscd
lrrlemycaplkpavqaqqhtdmpktqkevhlknasrgsagnknyrm.

Example 39

(15c) G1, P2, E3 are deleted, amino acid R36 is substituted by glutamine (Q), G42 is substituted by serin, the amino acids K68, S69, A70, R71 and S72 are deleted and amino acids R74, R77 and R104 are mutated to glutamine (Q).

(SEQ ID NO.: 63)
tlcgaelvdalqfvcgdrgfyfnkptgygsssqrapqtsivdeccfrscd
lrdemycaplkpavqaqqhtdmpktqkevhlknasrgsagnknyqm.

Example 40

(16c) G1, P2, E3 are deleted, amino acid R37 is substituted by glutamic acid (E), G42 is substituted by serin, the amino acids K68, S69, A70, R71 and S72 are deleted and amino acid R74 is mutated to glutamine (Q).

(SEQ ID NO.: 64)
tlcgaelvdalqfvcgdrgfyfnkptgygsssreapqtsivdeccf
rscdlrrlemycaplkpavqaqrhtdmpktqkevhlknasrgsagn
knyrm.

Example 41

(17c) G1, P2, E3 are deleted, amino acid R37 is substituted by glutamic acid (E), G42 is substituted by serin, the amino acids K68, S69, A70, R71 and S72 are deleted and amino acids R74 and R77 are mutated to glutamine (Q).

(SEQ ID NO.: 65)
tlcgaelvdalqfvcgdrgfyfnkptgygsssreapqtsivdeccf rscdlrrlemycaplkpavqaqqhtdmpktqkevhlknasrgsagn knyrm.

Example 42

(18c) G1, P2, E3 are deleted, amino acid R37 is substituted by glutamic acid (E), G42 is substituted by serin, the amino acids K68, S69, A70, R71 and S72 are deleted and amino acids R74, R77 and R104 are mutated to glutamine (Q).

(SEQ ID NO.: 66)
tlcgaelvdalqfvcgdrgfyfnkptgygsssreapqtsivdeccf rscdlrrlemycaplkpavqaqqhtdmpktqkevhlknasrgsagn knyqm.

Example 43

(19c) G1, P2, E3 are deleted, amino acid R37 is substituted by alanine (A), G42 is substituted by serin, the amino acids K68, S69, A70, R71 and S72 are deleted and amino acid R74 is mutated to glutamine (Q).

(SEQ ID NO.: 67)
tlcgaelvdalqfvcgdrgfyfnkptgygsssraapqtsivdeccf rscdlrrlemycaplkpavqaqrhtdmpktqkevhlknasrgsagn knyrm.

Example 44

(20c) G1, P2, E3 are deleted, amino acid R37 is substituted by alanine (A), G42 is substituted by serin, the amino acids K68, S69, A70, R71 and S72 are deleted and amino acids R74 and R77 are mutated to glutamine (Q).

(SEQ ID NO.: 68)
tlcgaelvdalqfvcgdrgfyfnkptgygsssraapqtsivdeccf rscdlrrlemycaplkpavqaqqhtdmpktqkevhlknasrgsagn knyrm.

Example 45

(21c) G1, P2, E3 are deleted, amino acid R37 is substituted by alanine (A), G42 is substituted by serin, the amino acids K68, S69, A70, R71 and S72 are deleted and amino acids R74, R77 and R104 are mutated to glutamine (Q).

(SEQ ID NO.: 69)
tlcgaelvdalqfvcgdrgfyfnkptgygsssraapqtsivdeccf rscdlrrlemycaplkpavqaqqhtdmpktqkevhlknasrgsagn knyqm.

Example 46

(22c) G1, P2, E3 are deleted, amino acid R37 is substituted by proline (P), G42 is substituted by serin, the amino acids K68, S69, A70, R71 and S72 are deleted and amino acid R74 is mutated to glutamine (Q).

(SEQ ID NO.: 70)
tlcgaelvdalqfvcgdrgfyfnkptgygsssrpapqtsivdeccf rscdlrrlemycaplkpavqaqrhtdmpktqkevhlknasrgsagn knyrm.

Example 47

(23c) G1, P2, E3 are deleted, amino acid R37 is substituted by proline (P), G42 is substituted by serin, the amino acids K68, S69, A70, R71 and S72 72 are deleted and amino acids R74 and R77 are mutated to glutamine (Q).

(SEQ ID NO.: 71)
tlcgaelvdalqfvcgdrgfyfnkptgygsssrpapqtsivdeccf rscdlrrlemycaplkpavqaqqhtdmpktqkevhlknasrgsagn knyrm.

Example 48

(24c) G1, P2, E3 are deleted, amino acid R37 is substituted by proline (P), G42 is substituted by serin, the amino acids K68, S69, A70, R71 and S72 are deleted and amino acids R74, R77 and R104 are mutated to glutamine (Q).

(SEQ ID NO.: 72)
tlcgaelvdalqfvcgdrgfyfnkptgygsssrpapqtsivdeccf rscdlrrlemycaplkpavqaqqhtdmpktqkevhlknasrgsagn knyqm.

Example 49

(25c) G1, P2, E3 are deleted, amino acid R36 and R37 are both substituted by glutamine (Q), G42 is substituted by serin, the amino acids K68, S69, A70, R71 and S72 are deleted and amino acid R74 is mutated to glutamine (Q).

(SEQ ID NO.: 73)
tlcgaelvdalqfvcgdrgfyfnkptgygsssqqapqtsivdeccf rscdlrrlemycaplkpavqaqrhtdmpktqkevhlknasrgsagn knyrm.

Example 50

(26c) G1, P2, E3 are deleted, amino acid R36 and R37 are both substituted by glutamine (Q), G42 is substituted by serin, the amino acids K68, S69, A70, R71 and S72 are deleted and amino acids R74 and R77 are mutated to glutamine (Q).

(SEQ ID NO.: 74)
tlcgaelvdalqfvcgdrgfyfnkptgygsssqqapqtsivdeccf rscdlrrlemycaplkpavqaqqhtdmpktqkevhlknasrgsagn knyrm.

Example 51

(27c) G1, P2, E3 are deleted, amino acid R36 is substituted by glutamine (Q), R37 is substituted by alanine, G42 is substituted by serin, the amino acids K68, S69, A70, R71 and S72 are deleted and amino acids R74 and R77 are mutated to glutamine (Q).

(SEQ ID NO.: 75)
tlcgaelvdalqfvcgdrgfyfnkptgygsssqaapqtsivdeccf rscdlrrlemycaplkpavqaqqhtdmpktqkevhlknasrgsagn knyrm.

Example 52

(28c) G1, P2, E3 are deleted, amino acid R36 and R37 are both substituted by glutamine (Q), G42 is substituted by serin, the amino acids K68, S69, A70, R71 and S72 are deleted and amino acids R74, R77 and R104 are mutated to glutamine (Q).

(SEQ ID NO.: 76)
tlcgaelvdalqfvcgdrgfyfnkptgygsssqqapqtsivdeccf rscdlrrlemycaplkpavqaqqhtdmpktqkevhlknasrgsagn knyqm.

Example 53

(29c) G1, P2, E3 are deleted, amino acid R36 is substituted by glutamine (Q), R37 is substituted by alanine, G42 is substituted by serin, the amino acids K68, S69, A70, R71 and S72 are deleted and amino acids R74, R77 and R104 are mutated to glutamine (Q).

(SEQ ID NO.: 77)
tlcgaelvdalqfvcgdrgfyfnkptgygsssqaapqtsivdeccf rscdlrrlemycaplkpavqaqqhtdmpktqkevhlknasrgsagn knyqm.

Example 54: Expression of Recombinant IGF-1 in CHO IGF-1 Receptor Deficient Cell Lines Expression of recombinant IGF-1 in CHO cell lines resulted in cell growth inhibition and low titers. In FIG. 11 titer measurements of hIGF-1 Ea 3mut (SEQ ID NO.: 27) during a bioreactor process is shown. The maximum titer measurement of hIGF-1Ea 3mut was 8 ug/ml which corresponds to 100 mg/L of an antibody titer (based on molar mass). The average titer measurements of a recombinant antibody in bioreactor process are around 3 g/L. One cause of the low titer of IGF-1 is reduced cell growth and low cell viability of IGF-1 expressing cells. During an antibody expression process CHO-K1 derivative cell cells grow up to 2-2.5×10$^7$ cells/ml and the cell viability is over 97% during the first 230-260 h cultivation time. In contrast CHO-K1 derivative cells expressing IGF-1 grow only up to 0.5-0.9× 10$^7$ cells/ml and the cell viability drops already after 80 h under 97% (see FIG. 11).

The reduced cell growth could also be detected during co-cultivation of non-transfected CHO-K1 derivative cells with IGF-1. FIG. 12 shows that parental CHO-K1 derivative cells grow up to 2.5×10$^7$ cells/ml. During co-cultivation of CHO-K1 derivative cells with wildtype IGF-1 or hIGF-1Ea 3mut (50 mg/L) cell growth is also significant inhibited (0.9×107 cells/ml).

In the next step a specific IGF-IR tyrosine kinase inhibitor (NVPAEW541 (In vivo antitumor activity of NVPAEW541—A novel, potent, and selective inhibitor of the IGF-IR kinase; Carlos García-Echeverría et al.; Cancer Cell; Published Online Feb. 26, 2004 DOI: 10.1016/S1535610804000510) was added during IGF-1 co-cultivation experiments in CHO-DUXB11 derivative cells. The cell growth inhibition could be prevented (see FIG. 13). This verifies that IGF-1-R triggers a signal into the cell resulting in cell growth inhibition.

In the next step a knockout of IGF-1R using zinc finger nuclease technique (ZFN) was performed in CHO-K1 derivative cell and CHO-DUXB11 derived cell lines. ZFN which are specific binding in the region of exon 3 of IGF-1R were designed. Two plasmids, each of them encoding for one subunit of the IGF-1R specific ZFN, were co-transfected in CHO-K1 derivative cell or CHO-DUXB11 derived cells. Each ZFN subunit binds specific 18 base pair long sequences; therefore overall a 36 bp sequence is specific recognized (avoiding random cutting on other locations of the genome). The endonuclease domain of FokI is reengineered to function only as heterodimer in order to cleave DNA. The ZFN dimer creates targeted double strand breaks at exon 3 of IGF-1R. Through the error prone cellular process of non-homologous end joining, this double strand break can result in modification of the DNA sequence and therefor creates a functional knockout of the targeted gene. For CHO-K1 derivative cell three knock out clones were generated (knock out on both alleles and frame shift mutations): Clone 1: Δ2 (SEQ ID NO.: 99), clone 2: Δ5 (SEQ ID NO.: 100) and clone 3: Δ2 (SEQ ID NO.: 101), Clone 1: +18 (and 14 bps substitution) (SEQ ID NO.: 103), clone 2: Δ22 (SEQ ID NO.: 102) and clone 3: Δ114 (SEQ ID NO.: 104).

CHO-DUXB11 derived cell line is in contrast to CHO-K1 derivative cell polyclonal and polyploidy which made the knockout of the IGF-1R challenging (more than 2 IGF-1R copies/genome had to be knocked out). We have generated several unique knockout clones with frame sift mutation and validated two of them with TOPO cloning and sequencing. Clone 12: Δ7 (50%) (SEQ ID NO.: 106)/Δ22 (50%) (SEQ ID NO.: 105), clone 19: Δ7 (14.5%)/Δ16 (44%)/Δ22 (18%)/Δ22mut (15%). The percentages in brackets are based on the frequency how often this mutation is occurring out of 32 sequenced bacterial colonies. For clone 19 it can be assumed that 6 IGF-1R allels are existent (3×Δ16, 1×Δ7, 1×Δ22, 1×Δ22mut). The three generated CHO-K1 derivative cell IGF-1R KO clones were co-cultivated with IGF-1 and no cell growth inhibition could be detected (see FIG. 14).

The two generated IGF-1R KO CHO-DUXB11 derived clones were also cultivated in the presence/absence of IGF-1. Similar as CHO-K1 IGF-1R KO clones an improved cell growth could be detected for the KO clones in comparison to the wild-type CHO-DUXB11 derived cells (see FIG. 15). One of the KO clones showed no cell growth inhibition in the presence of IGF-1 and the other KO clone had in the presence of IGF-1 a similar max. viable cell count as the CHO-DUXB11 derived cell without IGF-1 co-cultivation.

Cloning Strategy of Vector pBW806 (hIGF1-Ea-Fc_Mut 13/2_A).

Vector pBW806, encoding the hIGF1-Ea-fc_mut 13/2_A, was prepared following two consecutive cloning steps. In a first step plasmid 11AARNSC_hIGF1-Ea-fc_mut 13/2_E_pMA-T (Novartis propriety vector) was digested with XbaI and AscI in order to extract the de novo synthesized Fc region. In parallel pBW679 (Novartis propriety vector) was digested with AscI and XbaI generating the corresponding backbone fragment carrying transcriptional and translational regulatory elements as well as a G418/DHFR selection/amplification marker. Both digested elements were ligated by their compatible ends resulting in the intermediate vector pBW805. In a second step plasmid 11AARNUC_hIGF1-Ea-fc_mut 13/2_A_pMA-T (Novartis propriety vector) was digested with XbaI and Sse232I in order to extract the n-terminal region of the hIGF1-Ea-fc_mut 13/2_A fusion protein. In parallel the intermediate vector pBW805 was subsequently digested with Sse232I and XbaI delivering the desired backbone fraction which finally was ligated with the 11AARNUC_hIGF1-Ea-fc_mut 13/2_A_pMA-T fragment resulting in the final expression vector pBW806.

Cloning Strategy of Vector pBW807 (hIGF1-Ea-Fc_Mut 13/2_C).

Vector pBW807, encoding the hIGF1-Ea-fc_mut 13/2_C, was prepared following two consecutive cloning steps. In a first step plasmid 11AARNSC_hIGF1-Ea-fc_mut 13/2_E_pMA-T (Novartis propriety vector) was digested with XbaI and AscI in order to extract the de novo synthesized Fc region. In parallel pBW679 (Novartis propriety vector) was digested with AscI and XbaI generating the corresponding backbone fragment carrying transcriptional and translational regulatory elements as well as a G418/DHFR selection/amplification marker. Both digested elements were ligated by their compatible ends resulting in the intermediate vector pBW805. In a second step plasmid 11AARNWC_hIGF1-Ea-fc_mut 13/2_C_pMA-T (Novartis propriety vector) was digested with XbaI and Sse232I in order to extract the n-terminal region of the hIGF1-Ea-fc_mut 13/2_C fusion protein. In parallel the intermediate vector pBW805 was subsequently digested with Sse232I and XbaI delivering the desired backbone fraction which finally was ligated with the 11AARNUC_hIGF1-Ea-fc_mut 13/2_C_pMA-T (Novartis propriety vector) fragment resulting in the final expression vector pBW807.

Cloning Strategy of Vector pBW808 (hIgF1-Ea-Fc_Mut 13/2_F).

Vector pBW808, encoding the hIgF1-Ea-Fc_mut 13/2_F (Novartis propriety vector), was prepared following two consecutive cloning steps. In a first step plasmid 11AARN-SC_hIGF1-Ea-fc_mut 13/2_E_pMA-T (Novartis propriety vector) was digested with XbaI and AscI in order to extract the de novo synthesized Fc region. In parallel pBW679 (Novartis propriety vector) was digested with AscI and XbaI generating the corresponding backbone fragment carrying transcriptional and translational regulatory elements as well as a G418/DHFR selection/amplification marker. Both digested elements were ligated by their compatible ends resulting in the intermediate vector pBW805. In a second step plasmid 11AARNYC_hIgF1-Ea-Fc_mut 13/2_F_pMA-T (Novartis propriety vector) was digested with XbaI and Sse232I in order to extract the n-terminal region of the hIgF1-Ea-Fc_mut 13/2_Fc fusion protein. In parallel the intermediate vector pBW805 was subsequently digested with Sse232I and XbaI delivering the desired backbone fraction which finally was ligated with the 11AARNUC_hIgF1-Ea-Fc_mut 13/2_F_pMA-T (Novartis propriety vector) fragment resulting in the final expression vector pBW808.

Cloning Strategy of Vector pBW809 (hIGF1-Ea-Fc_Mut 04/2_E).

Vector pBW809, encoding the HIGF1-EA-FC_MUT 04/2_E Fc fusion sequence, was prepared following two consecutive cloning steps. In a first step plasmid 11AARN-SC_hIGF1-Ea-fc_mut 13/2_E_pMA-T (Novartis propriety vector) was digested with XbaI and AscI in order to extract the de novo synthesized Fc region. In parallel pBW679 (Novartis propriety vector) was digested with AscI and XbaI generating the corresponding backbone fragment carrying transcriptional and translational regulatory elements as well as a G418/DHFR selection/amplification marker. Both digested elements were ligated by their compatible ends resulting in the intermediate vector pBW805. In a second step plasmid 11AARN2C_hIGF1-Ea-fc_mut 04/2_E_pMA-T (Novartis propriety vector) was digested with XbaI and Sse232I in order to extract the n-terminal region of the hIGF1-Ea-fc_mut 04/2_E fusion protein. In parallel the intermediate vector pBW805 was subsequently digested with Sse232I and XbaI delivering the desired backbone fraction which finally was ligated with the 11AARNUC_hIGF1-Ea-fc_mut 04/2_E_pMA-T (Novartis propriety vector) fragment resulting in the final expression vector pBW809.

Cloning Strategy of Vector pBW810 (hIGF1-Ea-Fc_Mut 04/2_A).

Vector pBW810, encoding the hIGF1-Ea-fc_mut 04/2_A, was prepared following two consecutive cloning steps. In a first step plasmid 11AARNSC_hIGF1-Ea-fc_mut 13/2_E_pMA-T (Novartis propriety vector) was digested with XbaI and AscI in order to extract the de novo synthesized Fc region. In parallel pBW679 (Novartis propriety vector) was digested with AscI and XbaI generating the corresponding backbone fragment carrying transcriptional and translational regulatory elements as well as a G418/DHFR selection/amplification marker. Both digested elements were ligated by their compatible ends resulting in the intermediate vector pBW805. In a second step plasmid 11AARN2C_hIGF1-Ea-fc_mut 04/2_A_pMA-T (Novartis propriety vector) was digested with XbaI and Sse232I in order to extract the n-terminal region of the hIGF1-Ea-fc_mut 04/2_A fusion protein. In parallel the intermediate vector pBW805 was subsequently digested with Sse232I and XbaI delivering the desired backbone fraction which finally was ligated with the 11AARNUC_hIGF1-Ea-fc_mut 04/2_A_pMA-T (Novartis propriety vector) fragment resulting in the final expression vector pBW810.

Cloning Strategy of Vector pBW410 (hIGF-1Ea 3Mut).

Vector 0610900pGA4 (Novartis propriety vector), encoding the hIGF-1Ea 3mut sequence was digested with XbaI and MluI in order to extract the de novo synthesized coding IGF sequence. In parallel pBW165 (Novartis propriety vector) was digested with MluI and XbaI generating the corresponding backbone fragment carrying transcriptional and translational regulatory elements as well as a G418/DHFR selection/amplification marker. Both digested elements were ligated by their compatible ends resulting in the final expression vector pBW410.

Cloning Strategy of Vector pBW664 (hIGF1-Ea-D1-3, R37A, D71-72, 77-Fc Domain).

Vector 0905915 (Novartis propriety vector), encoding the hIGF1-Ea-D1-3, R37A, D71-72, 77-fc domain sequence was digested with XbaI and AscI in order to extract the de novo synthesized coding IGF sequence. In parallel pBW596 (Novartis propriety vector) was digested with AscI and XbaI generating the corresponding backbone fragment carrying transcriptional and translational regulatory elements as well as a G418/DHFR selection/amplification marker. Both digested elements were ligated by their compatible ends resulting in the final expression vector pBW664.

Cloning Strategy of Vector pBW666 (hIGF1-Ea-A1-3, R37A, A71-72, R77Q-Fc Domain).

Vector 0950919 (Novartis propriety vector), encoding the hIGF1-Ea-A1-3, R37A, A 71-72, R77Q-fc domain sequence was digested with XbaI and AscI in order to extract the de novo synthesized coding IGF sequence. In parallel pBW596 (Novartis propriety vector) was digested with AscI and XbaI generating the corresponding backbone fragment carrying transcriptional and translational regulatory elements as well as a G418/DHFR selection/amplification marker. Both digested elements were ligated by their compatible ends resulting in the final expression vector pBW666.

The Δ5/Δ22 CHO-K1 derivative cell IGF-1R KO clone as well as the Δ7/Δ22 CHO-DUXB11 cell derived IGF-1R KO clone were transfected with 5 different IGF-1-FC fusion candidates (see FIG. 15). A 5-17 fold titer increase of recombinant IGF-1-FC protein could be detected on pool level compared to the wild type CHO-K1 derivative cell/CHO-DUXB11 cell derived cell line transfected with a different IGF-1-FC fusion candidate.

Two of the IGF-1-FC fusion candidates (hIGF1-Ea-fc_mut 13/2_A and hIGF1-Ea-fc_mut 04/2_E) expressed in CHO-K1 derivative cell IGF1R-KO or CHO-DUXB11 derived IGF1R-KO cell lines was cultivated in 100 L wave bioreactor (fedbatch process and temperature shift). CHO-K1 derivative cell IGF1RKO pools expressing hIGF1-Ea-fc_mut 13/2_A/4 are growing up to a max. viable cell density of $3 \times 10^7$ cells/ml, which is higher than an average AB process (average cell density is $2.2 \times 10^7$ cells/ml. In comparison to the CHO-K1 derived wildtype cells expressing IGF-1 this is a 3-6 fold increase in viable cell numbers (see FIG. 11). CHO-DUXB11 derived IGF1RKO cells expressing hIGF1-Ea-fc_mut 13/2_A/4 were growing up to a max. cell density of $1.5$-$2 \times 10^7$ cells/ml which is higher max. cell density compared to the wildtype CHO-DUXB11 derived cell line.

The CHO-DUXB11 derived IGF1R KO cells expressing hIGF1-Ea-fc_mut 13/2_A were single cell sorted and batch titer in 24 well as well as in 50 ml batch cultures determined. In FIG. 15 the 24 well titer of the 30 best hIGF1-Ea-fc_mut 13/2_A clones in CHO-DUXB11 derived IGF-1R KO clones as well as of the 30 best hIGF-1-Ea-D1-3, R37A, D71-72, 77-fc domain expressing wildtype CHO-DUXB11 derived clones are shown; in FIG. 16 the shake flask titer of the 15 best clones from each group are shown. Overall the CHO-DUXB11 cell derived IGF-1R KO clones have an 8 fold higher 24 well titer and a 7 fold higher shake flask titer.

Example 55: Cultivation of Transformed CHO Cells Expressing IGF-1 in Bioreactor

For cultivation of transformed cells expressing IGF-1 in bioreactor a Fed-Batch process was applied. The process events such as feedstart and temperature shift were timed to support cell growth and to extend the production phase by maintaining viability (Niraj Kumar, Patrick Gammell, Martin Clynes (2007) Proliferation control strategies to improve productivity and survival during CHO based production culture; Cytotechnology (2007) 53:33-46).

Example 56: Harvesting of IGF-1 from CHO Cells

As harvest procedure a standard cell separation techniques with depth filtration followed by sterile filtration was applied. The CHO cells were cultivated and harvested according to standard methods known to the person skilled in the art (e.g. Curr. Protoc. Protein Sci. 2001 May; Chapter 5: Unit 5.10. Production of recombinant proteins in mammalian cells. Chen S, Gray D, Ma J, Subramanian S; (Mahesh Prashada, Klaus Tarrach (2006) Depth filtration: Cell clarification of bioreactor offloads, Filtration & Separation Volume 43, Issue 7, September 2006, Pages 28-30).

Example 57: Design/Production and Use of ZFNs which are Specific for Exon 3 of IGF-1R Exon 3 of IGF-1R and the flanking introns were sequenced in our CHO cell lines (SEQ ID NO.: 110/111). First, exon 3 was sequenced using a hamster DNA contig covering a part of IGF-1R cDNA which comprises exon 3, as well as the mouse sequence of the IGF-1R gene. PCR primers were designed on conserved parts and resulting PCR products were sequenced. The exon 3 sequence obtained was given to Sigma to sequence the exon 3 flanking introns as well as to design two engineered ZFNs targeting IGF-1R exon 3. Each ZFN is targeting and binding to 18 nucleotides on the reverse (on the 5') respectively the forward (on the 3') DNA strand. The two binding sites are separated by the five nucleotides of the cutting site (SEQ ID NO.: 107). A product description and methods is available at Sigma in a document called '74188 CompoZr Custom ZFN Tech Bulletin'. Sigma also designed the forward and reverse PCR primers in the surrounding intron sequences (SEQ ID NO.: 108 and 109) to amplify IGF-1R exon 3 in the gDNA, giving rise to a 501 bp PCR product. Sigma provided the kit CompoZr™ (Custom Zinc Finger Nucleases, product number CSTZFN-1 KT, lot number 08021019MN) comprising 20-25 µg of two DNA vectors, coding for the reverse (pZFN1) respectively the forward (pZFN2) strand-recognizing engineered ZFN.

E. Coli were transformed—according to well-known transformation protocols—with either vector and spread on 25 µg/ml Kanamycin containing agarose plates. For each vector, 4 bacterial colonies were picked and expanded. The ZFN sequences of the four purified DNA plasmid samples of each pZFN were validated using T7 forward and BHG reverse primers and pooled. 6 µg or 10 µg of a homogeneous mix of circular pZFN1 and pZFN2 vectors were transfected in CHO-K1 derivative cell and CHO-DUXB11 derivative parental cells, three times for each quantity, such that six pools were generated (plus negative control of transfection) with each cell line. To measure the cleavage efficiency of ZFNs in the pools, the Surveyor Mutation Detection assay (Transgenomics, catalog 706025) was used at days 3 and 10 after transfection (counted as day zero), as described in a confidential protocol provided by Sigma. The genomic DNA of the pools was isolated using the GenElute Mammalian Genomic DNA Miniprep kit (Sigma, catalog G1N70-1KT), the exon 3 amplified in a PCR reaction using the forward and reverse sequencing primers of IGF-1R lying in the flanking intron sequences. The PCR product was then denatured under high temperatures. When the temperature was gradually lowered, some wild-type and mutated product hybridize to form double strand DNA with mismatches around the cleavage site, which was cleaved by an enzyme called Surveyor®. The final products were analyzed using a gel electrophorese system called lab901. For all 6 transfected pools, additional to the 501 bp perfect match PCR product, two smaller bands of approximately 277 bp and 224 bp were detected, corresponding to the fragments on either side of the cutting site, thus attesting the ZFN activity in our cells. Seven days after transfection, the pools were single cell cloned in 10×96 well plates.

In the pZFN-transfected CHO-K1 derivative cell line, 507 clones were grown in 96-well plates and were assessed for mutations using the Surveyor Mutation Detection assay described above (the genomic DNA of clones is extracted in 96-well plates using Extract-N-Amp Blood PCR kit from Sigma, catalog XNAB2). 42 clones were positive (two smaller bands detected), meaning their genome contains at least a mutated copy of exon 3, and their PCR amplified IGF-1R exon 3 is sequenced. As expected for clones generated from a pseudo-diploid CHO-K1 derived cell line, the DNA sequencing chromatograms showed at maximum two overlaying signals of same intensity, indicating two copies of the target sequence. 6 clones had mutations in both copies, among which 3 clones had mutations triggering nearby stop codons in both copies (SEQ ID NO.: 99 and 100) or a nearby stop codons in one copy and a big deletion in the other (SEQ ID NO.: 101). The sequences of the two copies in those 3 clones were confirmed by TOPO cloning (TA cloning kit, Invitrogen, cat. K4575-40; 6 bacterial colonies picked). All the 3 K.O. clones were growing at significantly higher cell densities than the parental cells, and when IGF-1 (hIGF-1Ea 3mut' (SEQ ID NO.: 27) was spiked at 50 mg/L in standard medium, were growing at similar densities than parental cells in standard medium (FIG. 8). The clone with the genotype Δ5/Δ22 (SEQ ID NO.: 100/102) was selected for transfection with the Insulin like growth factor 1 protein, e.g. the human IGF-1 (SEQ ID NO.:1 or 5) or a variant thereof (e.g. SEQ ID NOs.: 8-14).

In the pZFN-transfected CHO-DUXB11 derivative cell line, only 117 clones were grown in 96-well plates and were assessed for mutations with Surveyor assay. 28 clones had at least one mutated copy of exon 3 (two smaller bands detected), but sequencing indicated that all those clones still had wild type copies; the wild type sequence had a higher intensity in sequencing chromatograms than the mutated sequence. The CHO-DUXB11 derivative cell line is mutagenized and polyclonal; karyotypes show up to eight copies of a chromosome in some cells, making the estimation of the expected copy number of a gene difficult. Two clones, in which the mutated sequence detected (Δ22 or Δ16) triggered nearby stop codons, were selected for a second round of transfection with pZFNs; 3 pools per original clones were generated using 10 μg of mixed pZFNs. Seven days after transfection, the pools were FACS cloned in 6×96 well plates. 379 clones were grown, from which 211 were sequenced for IGF-1R exon3 (no Surveyor assay possible anymore as already a mutated sequence) and overlapping sequences visually analyzed on chromatograms. Most of the sequenced clones were heterozygotes with the wild type and the expected mutated sequence (Δ22 or Δ16); ~20% of the clones had a wild type and 2 mutated sequences (mostly with deletions around the cutting site); in two clones 4 different sequences were detected (confirmed with TOPO cloning, but one of the sequence was either wild type or only one nucleotide insertion); 2 clones were K.O. clones, both with 2 sequences detected (Δ16/Δ22 and Δ16/Δ5), but their growth in presence of IGF-1 was too little better than in parental CHO-DUXB11 derivative cell line. Thus three clones, with the genotype Δ22/Δ7/wildtype, Δ16/Δ7/wildtype and Δ16/Δ22/wildtype, were selected for a third round of transfection with pZFNs (their sequences are confirmed by TOPO cloning, with 32 bacterial colonies picked and sequenced per clone). Each of the three clones was transfected 2 times with 8 μg pZFNs. Once the two pools from each clone recovered (viability>91%, after 7-9 days), they were pooled and co-cultivated about 6-8 weeks in presence of 50 mg/l IGF-1 (to select the more resistant cells). Two days before FACS cloning they were split without IGF-1 (to allow binding of IGF-1-Cy5 and select the 5% less fluorescent cells). The three pools were FACS cloned in a total of 9×96 well plates.

A PCR primer binding the wild type cutting site sequence in IGF-1R exon 3 was designed, allowing an efficient screening of mutated clones. The PCR was performed together with the forward sequencing primer for IGF-1R; assuming the PCR always works, if a clone was PCR negative, either there was no wild type sequence, or the clone did not grow well (too little DNA extracted so few cells grown). From the 389 grown clones such screened, 58 were negative and were sequenced. In 30 of those clones the wild type sequence was not detected, and for 22 clones mutations are were frameshifts (13 clones with the two sequences Δ22/Δ7, from the clone Δ22/Δ7/wild-type). Their growth with and without 50 mg/l IGF-1 was evaluated, and the best growing clone with IGF-1 (also among the best growing clone without IGF-1), with the sequences Δ22/Δ7 (verified by TOPO cloning), was selected for transfection with DNA constructs encoding the proteins of SEQ IDs No.: 8-14.

The invention claimed is:

1. A polypeptide comprising a human IGF-1 protein variant of SEQ ID NO: 1 wherein the amino acid glycine at position 42 is mutated to serine.

2. The polypeptide of claim 1, wherein the human IGF-1 protein variant is fused to an immunoglobulin Fc region of a human IgG, optionally by a peptide hinge region.

3. The polypeptide of claim 1, wherein the polypeptide is glycosylated.

4. A pharmaceutical composition comprising the polypeptide of claim 1 and a pharmaceutically acceptable carrier.

5. A polypeptide comprising a human IGF-1 protein variant of SEQ ID NO: 1 wherein the human IGF-1 protein variant has the following modifications:
   a. amino acid E3 is deleted,
   b. amino acid G42 is mutated to serine, and
   c. amino acid R37 is mutated to alanine.

6. A polypeptide comprising a human IGF-1 protein variant of SEQ ID NO: 1 wherein the human IGF-1 protein variant comprises the following modifications:
   a. amino acids G1, P2, E3 are deleted;
   b. amino acid G42 is mutated to serine;
   c. amino acid R36 is mutated to glutamine; and
   d. amino acid R37 is mutated to alanine.

7. A pharmaceutical composition comprising the polypeptide of claim 6 and a pharmaceutically acceptable carrier.

8. The polypeptide of claim 6, wherein the human IGF-1 protein variant is fused to an immunoglobulin Fc region of a human IgG, optionally by a peptide hinge region.

9. A polypeptide comprising a human IGF-1 protein variant of SEQ ID NO: 1 wherein the human IGF-1 protein variant comprises the following modifications:
   a. amino acids G1, P2, E3 are deleted,
   b. amino acid G42 is mutated to serine, and
   c. amino acid R37 is mutated to alanine.

10. A pharmaceutical composition comprising the polypeptide of claim 9 and a pharmaceutically acceptable carrier.

11. The polypeptide of claim 9, wherein the human IGF-1 protein variant is fused to an immunoglobulin Fc region of a human IgG, optionally by a peptide hinge region.

12. A polypeptide comprising a human IGF-1 protein variant of SEQ ID NO: 1 wherein the amino acid G42 is substituted by the amino acid serine and wherein the amino acid(s):
   (a) G1, P2, E3 are deleted and amino acid R36 is substituted or deleted; or
   (b) G1, P2, E3 are deleted and amino acid R36 is substituted by glutamine (Q); or
   (c) G1, P2, E3 are deleted and amino acid R37 is substituted or deleted; or
   (d) G1, P2, E3 are deleted and amino acid R37 is substituted by glutamic acid (E); or
   (e) G1, P2, E3 are deleted and amino acid R37 is substituted by alanine; or
   (f) G1, P2, E3 are deleted and amino acid R37 is substituted by proline (P); or
   (g) G1, P2, E3 are deleted and amino acids R36 and R37 are substituted or deleted; or
   (h) G1, P2, E3 are deleted and amino acid R36 and R37 are both substituted by glutamine (Q); or
   (i) G1, P2, E3 are deleted, amino acid R36 is substituted by glutamine (Q) and R37 is substituted by alanine.

13. A pharmaceutical composition comprising the polypeptide of claim 12 and a pharmaceutically acceptable carrier.

14. The polypeptide of claim 12, wherein the human IGF-1 protein variant is fused to an immunoglobulin Fc region of a human IgG, optionally by a peptide hinge region.

* * * * *

SEQUENCE LISTING

```
<160> NUMBER OF SEQ ID NOS: 118

<210> SEQ ID NO 1
<211> LENGTH: 70
<212> TYPE: PRT
<213> ORGANISM: Homo Sapiens

<400> SEQUENCE: 1

Gly Pro Glu Thr Leu Cys Gly Ala Glu Leu Val Asp Ala Leu Gln Phe
1               5                   10                  15
```

```
Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65              70

<210> SEQ ID NO 2
<211> LENGTH: 35
<212> TYPE: PRT
<213> ORGANISM: Homo Sapiens

<400> SEQUENCE: 2

Arg Ser Val Arg Ala Gln Arg His Thr Asp Met Pro Lys Thr Gln Lys
1               5                   10                  15

Glu Val His Leu Lys Asn Ala Ser Arg Gly Ser Ala Gly Asn Lys Asn
            20                  25                  30

Tyr Arg Met
        35

<210> SEQ ID NO 3
<211> LENGTH: 77
<212> TYPE: PRT
<213> ORGANISM: Homo Sapiens

<400> SEQUENCE: 3

Arg Ser Val Arg Ala Gln Arg His Thr Asp Met Pro Lys Thr Gln Lys
1               5                   10                  15

Tyr Gln Pro Pro Ser Thr Asn Lys Asn Thr Lys Ser Gln Arg Arg Lys
            20                  25                  30

Gly Trp Pro Lys Thr His Pro Gly Gly Glu Gln Lys Glu Gly Thr Glu
        35                  40                  45

Ala Ser Leu Gln Ile Arg Gly Lys Lys Lys Glu Gln Arg Arg Glu Ile
    50                  55                  60

Gly Ser Arg Asn Ala Glu Cys Arg Gly Lys Lys Gly Lys
65                  70                  75

<210> SEQ ID NO 4
<211> LENGTH: 40
<212> TYPE: PRT
<213> ORGANISM: Homo Sapiens

<400> SEQUENCE: 4

Arg Ser Val Arg Ala Gln Arg His Thr Asp Met Pro Lys Thr Gln Lys
1               5                   10                  15

Tyr Gln Pro Pro Ser Thr Asn Lys Asn Thr Lys Ser Gln Arg Arg Lys
            20                  25                  30

Gly Ser Thr Phe Glu Glu Arg Lys
        35                  40

<210> SEQ ID NO 5
<211> LENGTH: 105
<212> TYPE: PRT
<213> ORGANISM: Homo Sapiens

<400> SEQUENCE: 5

Gly Pro Glu Thr Leu Cys Gly Ala Glu Leu Val Asp Ala Leu Gln Phe
```

```
              1               5                  10                 15
Val Cys Gly Asp Arg Gly Phe Tyr Phe Asn Lys Pro Thr Gly Tyr Gly
              20                 25                 30

Ser Ser Ser Arg Arg Ala Pro Gln Thr Gly Ile Val Asp Glu Cys Cys
              35                 40                 45

Phe Arg Ser Cys Asp Leu Arg Leu Glu Met Tyr Cys Ala Pro Leu
              50                 55                 60

Lys Pro Ala Lys Ser Ala Arg Ser Val Arg Ala Gln Arg His Thr Asp
65               70                 75                 80

Met Pro Lys Thr Gln Lys Glu Val His Leu Lys Asn Ala Ser Arg Gly
                 85                 90                 95

Ser Ala Gly Asn Lys Asn Tyr Arg Met
                 100                105
```

<210> SEQ ID NO 6
<211> LENGTH: 328
<212> TYPE: PRT
<213> ORGANISM: Artificial Sequence
<220> FEATURE:
<223> OTHER INFORMATION: Mutated human IGF-1 protein: hIGF1-Ea-D1-3,
      R37A, D71-72, 77-fc domain

<400> SEQUENCE: 6

```
Thr Leu Cys Gly Ala Glu Leu Val Asp Ala Leu Gln Phe Val Cys Gly
1               5                  10                 15

Asp Arg Gly Phe Tyr Phe Asn Lys Pro Thr Gly Tyr Gly Ser Ser Ser
              20                 25                 30

Arg Ala Ala Pro Gln Thr Gly Ile Val Asp Glu Cys Cys Phe Arg Ser
              35                 40                 45

Cys Asp Leu Arg Arg Leu Glu Met Tyr Cys Ala Pro Leu Lys Pro Ala
              50                 55                 60

Lys Ser Ala Val Arg Ala Gln His Thr Asp Met Pro Lys Thr Gln Lys
65               70                 75                 80

Glu Val His Leu Lys Asn Ala Ser Arg Gly Ser Ala Gly Asn Lys Asn
                 85                 90                 95

Tyr Arg Met Gly Ser Asp Lys Thr His Thr Cys Pro Pro Cys Pro Ala
              100                105                110

Pro Glu Ala Ala Gly Gly Pro Ser Val Phe Leu Phe Pro Pro Lys Pro
              115                120                125

Lys Asp Thr Leu Met Ile Ser Arg Thr Pro Glu Val Thr Cys Val Val
              130                135                140

Val Asp Val Ser His Glu Asp Pro Glu Val Lys Phe Asn Trp Tyr Val
145              150                155                160

Asp Gly Val Glu Val His Asn Ala Lys Thr Lys Pro Arg Glu Glu Gln
                 165                170                175

Tyr Asn Ser Thr Tyr Arg Val Val Ser Val Leu Thr Val Leu His Gln
              180                185                190

Asp Trp Leu Asn Gly Lys Glu Tyr Lys Cys Lys Val Ser Asn Lys Ala
              195                200                205

Leu Pro Ala Pro Ile Glu Lys Thr Ile Ser Lys Ala Lys Gly Gln Pro
              210                215                220

Arg Glu Pro Gln Val Tyr Thr Leu Pro Pro Ser Arg Glu Glu Met Thr
225              230                235                240

Lys Asn Gln Val Ser Leu Thr Cys Leu Val Lys Gly Phe Tyr Pro Ser
                 245                250                255
```

```
Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
        275                 280                 285

Ser Lys Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly Lys
                325

<210> SEQ ID NO 7
<211> LENGTH: 329
<212> TYPE: PRT
<213> ORGANISM: Artificial Sequence
<220> FEATURE:
<223> OTHER INFORMATION: Mutated human IGF-1 protein: hIGF1-Ea-D1-3,
      R37A, D71-72, R77Q-fc domain

<400> SEQUENCE: 7

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Val Arg Ala Gln Gln His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Arg Met Gly Ser Asp Lys Thr His Thr Cys Pro Pro Cys Pro
            100                 105                 110

Ala Pro Glu Ala Ala Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285
```

```
Tyr Ser Lys Leu Thr Val Asp Lys Ser Arg Trp Gln Gln Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 8
<211> LENGTH: 324
<212> TYPE: PRT
<213> ORGANISM: Artificial Sequence
<220> FEATURE:
<223> OTHER INFORMATION: Mutated human IGF-1 protein: hIgF1-Ea-Fc_mut
      13/2_E

<400> SEQUENCE: 8

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
                20                  25                  30

Gln Ala Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
50                  55                  60

Val Gln Ala Gln Gln His Thr Asp Met Pro Lys Thr Gln Lys Glu Val
65                  70                  75                  80

His Leu Lys Asn Ala Ser Arg Gly Ser Ala Gly Asn Lys Asn Tyr Gln
                85                  90                  95

Met Asp Lys Thr His Thr Cys Pro Pro Cys Pro Ala Pro Glu Ala Ala
            100                 105                 110

Gly Gly Pro Ser Val Phe Leu Phe Pro Pro Lys Pro Lys Asp Thr Leu
        115                 120                 125

Met Ile Ser Arg Thr Pro Glu Val Thr Cys Val Val Val Asp Val Ser
    130                 135                 140

His Glu Asp Pro Glu Val Lys Phe Asn Trp Tyr Val Asp Gly Val Glu
145                 150                 155                 160

Val His Asn Ala Lys Thr Lys Pro Arg Glu Glu Gln Tyr Asn Ser Thr
                165                 170                 175

Tyr Arg Val Val Ser Val Leu Thr Val Leu His Gln Asp Trp Leu Asn
            180                 185                 190

Gly Lys Glu Tyr Lys Cys Lys Val Ser Asn Lys Ala Leu Pro Ala Pro
        195                 200                 205

Ile Glu Lys Thr Ile Ser Lys Ala Lys Gly Gln Pro Arg Glu Pro Gln
    210                 215                 220

Val Tyr Thr Leu Pro Pro Ser Arg Glu Glu Met Thr Lys Asn Gln Val
225                 230                 235                 240

Ser Leu Thr Cys Leu Val Lys Gly Phe Tyr Pro Ser Asp Ile Ala Val
                245                 250                 255

Glu Trp Glu Ser Asn Gly Gln Pro Glu Asn Asn Tyr Lys Thr Thr Pro
            260                 265                 270

Pro Val Leu Asp Ser Asp Gly Ser Phe Phe Leu Tyr Ser Lys Leu Thr
        275                 280                 285

Val Asp Lys Ser Arg Trp Gln Gln Gly Asn Val Phe Ser Cys Ser Val
    290                 295                 300

Met His Glu Ala Leu His Asn His Tyr Thr Gln Lys Ser Leu Ser Leu
```

Ser Pro Gly Lys

<210> SEQ ID NO 9
<211> LENGTH: 319
<212> TYPE: PRT
<213> ORGANISM: Artificial Sequence
<220> FEATURE:
<223> OTHER INFORMATION: Mutated human IGF-1 protein: hIgF1-Ea-Fc_mut 13/2_A

<400> SEQUENCE: 9

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Ala Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
50                  55                  60

Val Gln Ala Gln Gln His Thr Asp Met Pro Lys Thr Gln Lys Glu Val
65                  70                  75                  80

His Leu Lys Asn Ala Ser Arg Gly Ser Ala Gly Asn Lys Asn Tyr Gln
                85                  90                  95

Met Cys Pro Pro Cys Pro Ala Pro Glu Ala Ala Gly Gly Pro Ser Val
            100                 105                 110

Phe Leu Phe Pro Pro Lys Pro Lys Asp Thr Leu Met Ile Ser Arg Thr
        115                 120                 125

Pro Glu Val Thr Cys Val Val Val Asp Val Ser His Glu Asp Pro Glu
130                 135                 140

Val Lys Phe Asn Trp Tyr Val Asp Gly Val Glu Val His Asn Ala Lys
145                 150                 155                 160

Thr Lys Pro Arg Glu Glu Gln Tyr Asn Ser Thr Tyr Arg Val Val Ser
                165                 170                 175

Val Leu Thr Val Leu His Gln Asp Trp Leu Asn Gly Lys Glu Tyr Lys
            180                 185                 190

Cys Lys Val Ser Asn Lys Ala Leu Pro Ala Pro Ile Glu Lys Thr Ile
        195                 200                 205

Ser Lys Ala Lys Gly Gln Pro Arg Glu Pro Gln Val Tyr Thr Leu Pro
210                 215                 220

Pro Ser Arg Glu Glu Met Thr Lys Asn Gln Val Ser Leu Thr Cys Leu
225                 230                 235                 240

Val Lys Gly Phe Tyr Pro Ser Asp Ile Ala Val Glu Trp Glu Ser Asn
                245                 250                 255

Gly Gln Pro Glu Asn Asn Tyr Lys Thr Thr Pro Pro Val Leu Asp Ser
            260                 265                 270

Asp Gly Ser Phe Phe Leu Tyr Ser Lys Leu Thr Val Asp Lys Ser Arg
        275                 280                 285

Trp Gln Gln Gly Asn Val Phe Ser Cys Ser Val Met His Glu Ala Leu
290                 295                 300

His Asn His Tyr Thr Gln Lys Ser Leu Ser Leu Ser Pro Gly Lys
305                 310                 315

<210> SEQ ID NO 10
<211> LENGTH: 309
<212> TYPE: PRT

<213> ORGANISM: Artificial Sequence
<220> FEATURE:
<223> OTHER INFORMATION: Mutated human IGF-1 protein: hIgF1-Ea-Fc_mut 13/2_C

<400> SEQUENCE: 10

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Ala Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Val Gln Ala Gln Gln His Thr Asp Met Pro Lys Thr Gln Lys Glu Val
65                  70                  75                  80

His Leu Lys Asn Ala Ser Gly Cys Pro Pro Cys Pro Ala Pro Glu Ala
                85                  90                  95

Ala Gly Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser His Glu Asp Pro Glu Val Lys Phe Asn Trp Tyr Val Asp Gly Val
    130                 135                 140

Glu Val His Asn Ala Lys Thr Lys Pro Arg Glu Glu Gln Tyr Asn Ser
145                 150                 155                 160

Thr Tyr Arg Val Val Ser Val Leu Thr Val Leu His Gln Asp Trp Leu
                165                 170                 175

Asn Gly Lys Glu Tyr Lys Cys Lys Val Ser Asn Lys Ala Leu Pro Ala
            180                 185                 190

Pro Ile Glu Lys Thr Ile Ser Lys Ala Lys Gly Gln Pro Arg Glu Pro
        195                 200                 205

Gln Val Tyr Thr Leu Pro Pro Ser Arg Glu Glu Met Thr Lys Asn Gln
    210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Lys Leu
            260                 265                 270

Thr Val Asp Lys Ser Arg Trp Gln Gln Gly Asn Val Phe Ser Cys Ser
        275                 280                 285

Val Met His Glu Ala Leu His Asn His Tyr Thr Gln Lys Ser Leu Ser
    290                 295                 300

Leu Ser Pro Gly Lys
305

<210> SEQ ID NO 11
<211> LENGTH: 314
<212> TYPE: PRT
<213> ORGANISM: Artificial Sequence
<220> FEATURE:
<223> OTHER INFORMATION: Mutated human IGF-1 protein: hIgF1-Ea-Fc_mut 13/2_F

<400> SEQUENCE: 11

Thr Leu Cys Gly Ala Glu Leu Val Asp Ala Leu Gln Phe Val Cys Gly

```
  1               5                  10                 15
Asp Arg Gly Phe Tyr Phe Asn Lys Pro Thr Gly Tyr Gly Ser Ser Ser
                 20                 25                 30

Gln Ala Ala Pro Gln Thr Ser Ile Val Asp Glu Cys Cys Phe Arg Ser
                 35                 40                 45

Cys Asp Leu Arg Arg Leu Glu Met Tyr Cys Ala Pro Leu Lys Pro Ala
    50                  55                 60

Val Gln Ala Gln Gln His Thr Asp Met Pro Lys Thr Gln Lys Glu Val
65                  70                  75                  80

His Leu Lys Asn Ala Ser Gly Asp Lys Thr His Thr Cys Pro Pro Cys
                85                  90                  95

Pro Ala Pro Glu Ala Ala Gly Gly Pro Ser Val Phe Leu Phe Pro Pro
                100                 105                 110

Lys Pro Lys Asp Thr Leu Met Ile Ser Arg Thr Pro Glu Val Thr Cys
                115                 120                 125

Val Val Val Asp Val Ser His Glu Asp Pro Glu Val Lys Phe Asn Trp
130                 135                 140

Tyr Val Asp Gly Val Glu Val His Asn Ala Lys Thr Lys Pro Arg Glu
145                 150                 155                 160

Glu Gln Tyr Asn Ser Thr Tyr Arg Val Val Ser Val Leu Thr Val Leu
                    165                 170                 175

His Gln Asp Trp Leu Asn Gly Lys Glu Tyr Lys Cys Lys Val Ser Asn
                180                 185                 190

Lys Ala Leu Pro Ala Pro Ile Glu Lys Thr Ile Ser Lys Ala Lys Gly
                195                 200                 205

Gln Pro Arg Glu Pro Gln Val Tyr Thr Leu Pro Pro Ser Arg Glu Glu
                210                 215                 220

Met Thr Lys Asn Gln Val Ser Leu Thr Cys Leu Val Lys Gly Phe Tyr
225                 230                 235                 240

Pro Ser Asp Ile Ala Val Glu Trp Ser Asn Gly Gln Pro Glu Asn
                245                 250                 255

Asn Tyr Lys Thr Thr Pro Pro Val Leu Asp Ser Asp Gly Ser Phe Phe
                260                 265                 270

Leu Tyr Ser Lys Leu Thr Val Asp Lys Ser Arg Trp Gln Gln Gly Asn
                275                 280                 285

Val Phe Ser Cys Ser Val Met His Glu Ala Leu His Asn His Tyr Thr
                290                 295                 300

Gln Lys Ser Leu Ser Leu Ser Pro Gly Lys
305                 310

<210> SEQ ID NO 12
<211> LENGTH: 324
<212> TYPE: PRT
<213> ORGANISM: Artificial Sequence
<220> FEATURE:
<223> OTHER INFORMATION: Mutated human IGF-1 protein: hIgF1-Ea-Fc_mut
      04/2_E

<400> SEQUENCE: 12

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
                20                  25                  30

Arg Glu Ala Pro Gln Thr Ser Ile Val Asp Glu Cys Cys Phe Arg Ser
                35                  40                  45
```

Cys Asp Leu Arg Arg Leu Glu Met Tyr Cys Ala Pro Leu Lys Pro Ala
    50                  55                  60

Val Gln Ala Gln Gln His Thr Asp Met Pro Lys Thr Gln Lys Glu Val
65                  70                  75                  80

His Leu Lys Asn Ala Ser Arg Gly Ser Ala Gly Asn Lys Asn Tyr Gln
                85                  90                  95

Met Asp Lys Thr His Thr Cys Pro Pro Cys Pro Ala Pro Glu Ala Ala
            100                 105                 110

Gly Gly Pro Ser Val Phe Leu Phe Pro Pro Lys Pro Lys Asp Thr Leu
            115                 120                 125

Met Ile Ser Arg Thr Pro Glu Val Thr Cys Val Val Val Asp Val Ser
130                 135                 140

His Glu Asp Pro Glu Val Lys Phe Asn Trp Tyr Val Asp Gly Val Glu
145                 150                 155                 160

Val His Asn Ala Lys Thr Lys Pro Arg Glu Glu Gln Tyr Asn Ser Thr
                165                 170                 175

Tyr Arg Val Val Ser Val Leu Thr Val Leu His Gln Asp Trp Leu Asn
            180                 185                 190

Gly Lys Glu Tyr Lys Cys Lys Val Ser Asn Lys Ala Leu Pro Ala Pro
            195                 200                 205

Ile Glu Lys Thr Ile Ser Lys Ala Lys Gly Gln Pro Arg Glu Pro Gln
210                 215                 220

Val Tyr Thr Leu Pro Pro Ser Arg Glu Glu Met Thr Lys Asn Gln Val
225                 230                 235                 240

Ser Leu Thr Cys Leu Val Lys Gly Phe Tyr Pro Ser Asp Ile Ala Val
                245                 250                 255

Glu Trp Glu Ser Asn Gly Gln Pro Glu Asn Asn Tyr Lys Thr Thr Pro
            260                 265                 270

Pro Val Leu Asp Ser Asp Gly Ser Phe Phe Leu Tyr Ser Lys Leu Thr
            275                 280                 285

Val Asp Lys Ser Arg Trp Gln Gln Gly Asn Val Phe Ser Cys Ser Val
290                 295                 300

Met His Glu Ala Leu His Asn His Tyr Thr Gln Lys Ser Leu Ser Leu
305                 310                 315                 320

Ser Pro Gly Lys

<210> SEQ ID NO 13
<211> LENGTH: 319
<212> TYPE: PRT
<213> ORGANISM: Artificial Sequence
<220> FEATURE:
<223> OTHER INFORMATION: Mutated human IGF-1 protein: hIgF1-Ea-Fc_mut
      04/2_A

<400> SEQUENCE: 13

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
                20                  25                  30

Arg Glu Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
    50                  55                  60

Val Gln Ala Gln Gln His Thr Asp Met Pro Lys Thr Gln Lys Glu Val
65                  70                  75                  80

```
His Leu Lys Asn Ala Ser Arg Gly Ser Ala Gly Asn Lys Asn Tyr Gln
                85                  90                  95

Met Cys Pro Pro Cys Pro Ala Pro Glu Ala Ala Gly Gly Pro Ser Val
           100                 105                 110

Phe Leu Phe Pro Pro Lys Pro Lys Asp Thr Leu Met Ile Ser Arg Thr
       115                 120                 125

Pro Glu Val Thr Cys Val Val Val Asp Val Ser His Glu Asp Pro Glu
   130                 135                 140

Val Lys Phe Asn Trp Tyr Val Asp Gly Val Glu Val His Asn Ala Lys
145                 150                 155                 160

Thr Lys Pro Arg Glu Glu Gln Tyr Asn Ser Thr Tyr Arg Val Val Ser
               165                 170                 175

Val Leu Thr Val Leu His Gln Asp Trp Leu Asn Gly Lys Glu Tyr Lys
           180                 185                 190

Cys Lys Val Ser Asn Lys Ala Leu Pro Ala Pro Ile Glu Lys Thr Ile
       195                 200                 205

Ser Lys Ala Lys Gly Gln Pro Arg Glu Pro Gln Val Tyr Thr Leu Pro
   210                 215                 220

Pro Ser Arg Glu Glu Met Thr Lys Asn Gln Val Ser Leu Thr Cys Leu
225                 230                 235                 240

Val Lys Gly Phe Tyr Pro Ser Asp Ile Ala Val Glu Trp Glu Ser Asn
               245                 250                 255

Gly Gln Pro Glu Asn Asn Tyr Lys Thr Thr Pro Pro Val Leu Asp Ser
           260                 265                 270

Asp Gly Ser Phe Phe Leu Tyr Ser Lys Leu Thr Val Asp Lys Ser Arg
       275                 280                 285

Trp Gln Gln Gly Asn Val Phe Ser Cys Ser Val Met His Glu Ala Leu
   290                 295                 300

His Asn His Tyr Thr Gln Lys Ser Leu Ser Leu Ser Pro Gly Lys
305                 310                 315

<210> SEQ ID NO 14
<211> LENGTH: 314
<212> TYPE: PRT
<213> ORGANISM: Artificial Sequence
<220> FEATURE:
<223> OTHER INFORMATION: Mutated human IGF-1 protein: hIgF1-Ea-Fc_mut
      04/2_F

<400> SEQUENCE: 14

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
               20                  25                  30

Arg Glu Ala Pro Gln Thr Ser Ile Val Asp Glu Cys Cys Phe Arg Ser
           35                  40                  45

Cys Asp Leu Arg Arg Leu Glu Met Tyr Cys Ala Pro Leu Lys Pro Ala
       50                  55                  60

Val Gln Ala Gln Gln His Thr Asp Met Pro Lys Thr Gln Lys Glu Val
65                  70                  75                  80

His Leu Lys Asn Ala Ser Gly Asp Lys Thr His Thr Cys Pro Pro Cys
                85                  90                  95

Pro Ala Pro Glu Ala Ala Gly Gly Pro Ser Val Phe Leu Phe Pro Pro
           100                 105                 110

Lys Pro Lys Asp Thr Leu Met Ile Ser Arg Thr Pro Glu Val Thr Cys
       115                 120                 125
```

Val Val Val Asp Val Ser His Glu Asp Pro Glu Val Lys Phe Asn Trp
    130                 135                 140

Tyr Val Asp Gly Val Glu Val His Asn Ala Lys Thr Lys Pro Arg Glu
145                 150                 155                 160

Glu Gln Tyr Asn Ser Thr Tyr Arg Val Val Ser Val Leu Thr Val Leu
                165                 170                 175

His Gln Asp Trp Leu Asn Gly Lys Glu Tyr Lys Cys Lys Val Ser Asn
            180                 185                 190

Lys Ala Leu Pro Ala Pro Ile Glu Lys Thr Ile Ser Lys Ala Lys Gly
        195                 200                 205

Gln Pro Arg Glu Pro Gln Val Tyr Thr Leu Pro Pro Ser Arg Glu Glu
    210                 215                 220

Met Thr Lys Asn Gln Val Ser Leu Thr Cys Leu Val Lys Gly Phe Tyr
225                 230                 235                 240

Pro Ser Asp Ile Ala Val Glu Trp Glu Ser Asn Gly Gln Pro Glu Asn
                245                 250                 255

Asn Tyr Lys Thr Thr Pro Pro Val Leu Asp Ser Asp Gly Ser Phe Phe
            260                 265                 270

Leu Tyr Ser Lys Leu Thr Val Asp Lys Ser Arg Trp Gln Gln Gly Asn
        275                 280                 285

Val Phe Ser Cys Ser Val Met His Glu Ala Leu His Asn His Tyr Thr
    290                 295                 300

Gln Lys Ser Leu Ser Leu Ser Pro Gly Lys
305                 310

<210> SEQ ID NO 15
<211> LENGTH: 972
<212> TYPE: DNA
<213> ORGANISM: Artificial Sequence
<220> FEATURE:
<223> OTHER INFORMATION: DNA encoding a mutated human IGF-1 protein:
      hIgF1-Ea-Fc_mut 13/2_E

<400> SEQUENCE: 15
acgctctgcg gggctgagct ggtggatgct cttcagttcg tgtgtggaga caggggcttt      60
tatttcaaca agcccacagg gtatggctcc agcagtcagg cggcgcctca gacaagcatc     120
gtggatgagt gctgcttccg gagctgtgat ctaaggaggc tggagatgta ttgcgcaccc     180
ctcaagcctg ccgtccaggc ccagcagcac accgacatgc caagaccca gaaggaagta     240 catttgaaga acgcaagtag agggagtgca ggaaacaaga actaccagat ggacaaaact     300
cacacatgcc caccgtgccc agcacctgaa gcagcggggg gaccgtcagt cttcctcttc     360 ccccaaaac ccaaggacac cctcatgatc tcccggaccc ctgaggtcac atgcgtggtg     420
gtggacgtga gccacgaaga ccctgaggtc aagttcaact ggtacgtgga cggcgtggag     480
gtgcataatg ccaagacaaa gccgcgggag gagcagtaca acagcacgta ccgggtggtc     540
agcgtcctca ccgtcctgca ccaggactgg ctgaatggca aggagtacaa gtgcaaggtc     600
tccaacaaag ccctcccagc ccccatcgag aaaaccatct ccaaagccaa agggcagccc     660
cgagaaccac aggtgtacac cctgccccca tcccgggagg agatgaccaa gaaccaggtc     720
agcctgacct gcctggtcaa aggcttctat cccagcgaca tcgccgtgga gtgggagagc     780
aatgggcagc cggagaacaa ctacaagacc acgcctcccg tgctggactc cgacggctcc     840
ttcttcctct acagcaagct caccgtggac aagagcaggt ggcagcaggg gaacgtcttc     900
tcatgctccg tgatgcatga ggctctgcac aaccactaca cgcagaagag cctctccctg     960
tctccgggta aa                                                              972

<210> SEQ ID NO 16
<211> LENGTH: 957
<212> TYPE: DNA
<213> ORGANISM: Artificial Sequence
<220> FEATURE:
<223> OTHER INFORMATION: DNA encoding a mutated human IGF-1 protein:
      hIgF1-Ea-Fc_mut 13/2_A

<400> SEQUENCE: 16
acgctctgcg gggctgagct ggtggatgct cttcagttcg tgtgtggaga caggggcttt    60
tatttcaaca agcccacagg gtatggctcc agcagtcagg cggcgcctca gacaagcatc   120
gtggatgagt gctgcttccg gagctgtgat ctaaggaggc tggagatgta ttgcgcaccc   180
ctcaagcctg ccgtccaggc ccagcagcac accgacatgc ccaagaccca gaaggaagta   240
catttgaaga acgcaagtag agggagtgca ggaaacaaga actaccagat gtgcccaccg   300
tgcccagcac ctgaagcagc gggggaccg tcagtcttcc tcttcccccc aaaacccaag   360
gacaccctca tgatctcccg gacccctgag gtcacatgcg tggtggtgga cgtgagccac   420
gaagaccctg aggtcaagtt caactggtac gtggacggcg tggaggtgca taatgccaag   480
acaaagccgc gggaggagca gtacaacagc acgtaccggg tggtcagcgt cctcaccgtc   540
ctgcaccagg actggctgaa tggcaaggag tacaagtgca aggtctccaa caaagccctc   600
ccagccccca tcgagaaaac catctccaaa gccaaagggc agccccgaga accacaggtg   660
tacaccctgc cccatcccg ggaggagatg accaagaacc aggtcagcct gacctgcctg   720
gtcaaaggct tctatcccag cgacatcgcc gtggagtggg agagcaatgg gcagccggag   780
aacaactaca agaccacgcc tcccgtgctg gactccgacg gctccttctt cctctacagc   840
aagctcaccg tggacaagag caggtggcag caggggaacg tcttctcatg ctccgtgatg   900
catgaggctc tgcacaacca ctacacgcag aagagcctct ccctgtctcc gggtaaa     957

<210> SEQ ID NO 17
<211> LENGTH: 927
<212> TYPE: DNA
<213> ORGANISM: Artificial Sequence
<220> FEATURE:
<223> OTHER INFORMATION: DNA encoding a mutated human IGF-1 protein:
      hIgF1-Ea-Fc_mut 13/2_C

<400> SEQUENCE: 17
acgctctgcg gggctgagct ggtggatgct cttcagttcg tgtgtggaga cagggggcttt   60
tatttcaaca agcccacagg gtatggctcc agcagtcagg cggcgcctca gacaagcatc   120
gtggatgagt gctgcttccg gagctgtgat ctaaggaggc tggagatgta ttgcgcaccc   180
ctcaagcctg ccgtccaggc ccagcagcac accgacatgc ccaagaccca gaaggaagta   240
catttgaaga acgcaagtgg gtgcccaccg tgcccagcac ctgaagcagc gggggaccg   300
tcagtcttcc tcttcccccc aaaacccaag gacaccctca tgatctcccg gacccctgag   360
gtcacatgcg tggtggtgga cgtgagccac gaagaccctg aggtcaagtt caactggtac   420
gtggacggcg tggaggtgca taatgccaag acaaagccgc gggaggagca gtacaacagc   480
acgtaccggg tggtcagcgt cctcaccgtc ctgcaccagg actggctgaa tggcaaggag   540
tacaagtgca aggtctccaa caaagccctc ccagccccca tcgagaaaac catctccaaa   600
gccaaagggc agccccgaga accacaggtg tacaccctgc cccatcccg ggaggagatg     660

```
accaagaacc aggtcagcct gacctgcctg gtcaaaggct tctatcccag cgacatcgcc    720
gtggagtggg agagcaatgg gcagccggag aacaactaca agaccacgcc tcccgtgctg    780
gactccgacg gctccttctt cctctacagc aagctcaccg tggacaagag caggtggcag    840
caggggaacg tcttctcatg ctccgtgatg catgaggctc tgcacaacca ctacacgcag    900
aagagcctct ccctgtctcc gggtaaa                                        927
```

<210> SEQ ID NO 18
<211> LENGTH: 942
<212> TYPE: DNA
<213> ORGANISM: Artificial Sequence
<220> FEATURE:
<223> OTHER INFORMATION: DNA encoding a mutated human IGF-1 protein:
      hIgF1-Ea-Fc_mut 13/2_F

<400> SEQUENCE: 18

```
acgctctgcg gggctgagct ggtggatgct cttcagttcg tgtgtggaga caggggcttt    60
tatttcaaca agcccacagg gtatggctcc agcagtcagg cggcgcctca gacaagcatc    120
gtggatgagt gctgcttccg gagctgtgat ctaaggaggc tggagatgta ttgcgcaccc    180
ctcaagcctg ccgtccaggc ccagcagcac accgacatgc ccaagaccca gaaggaagta    240
catttgaaga acgcaagtgg ggacaaaact cacacatgcc caccgtgccc agcacctgaa    300
gcagcggggg gaccgtcagt cttcctcttc cccccaaaac ccaaggacac cctcatgatc    360
tcccggaccc ctgaggtcac atgcgtggtg gtggacgtga gccacgaaga ccctgaggtc    420
aagttcaact ggtacgtgga cggcgtggag gtgcataatg ccaagacaaa gccgcgggag    480
gagcagtaca acagcacgta ccgggtggtc agcgtcctca ccgtcctgca ccaggactgg    540
ctgaatggca aggagtacaa gtgcaaggtc tccaacaaag ccctcccagc ccccatcgag    600
aaaaccatct ccaaagccaa agggcagccc cgagaaccac aggtgtacac cctgccccca    660
tcccgggagg agatgaccaa gaaccaggtc agcctgacct gcctggtcaa aggcttctat    720
cccagcgaca tcgccgtgga gtgggagagc aatgggcagc cggagaacaa ctacaagacc    780
acgcctcccg tgctggactc cgacggctcc ttcttcctct acagcaagct caccgtggac    840
aagagcaggt ggcagcaggg gaacgtcttc tcatgctccg tgatgcatga ggctctgcac    900
aaccactaca cgcagaagag cctctccctg tctccgggta aa                      942
```

<210> SEQ ID NO 19
<211> LENGTH: 972
<212> TYPE: DNA
<213> ORGANISM: Artificial Sequence
<220> FEATURE:
<223> OTHER INFORMATION: DNA encoding a mutated human IGF-1 protein:
      hIgF1-Ea-Fc_mut 04/2_E

<400> SEQUENCE: 19

```
acgctctgcg gggctgagct ggtggatgct cttcagttcg tgtgtggaga caggggcttt    60
tatttcaaca agcccacagg gtatggctcc agcagtcggg aggcgcctca gacaagcatc    120
gtggatgagt gctgcttccg gagctgtgat ctaaggaggc tggagatgta ttgcgcaccc    180
ctcaagcctg ccgtccaggc ccagcagcac accgacatgc ccaagaccca gaaggaagta    240
catttgaaga acgcaagtag agggagtgca ggaaacaaga actaccagat ggacaaaact    300
cacacatgcc caccgtgccc agcacctgaa gcagcggggg gaccgtcagt cttcctcttc    360
cccccaaaac ccaaggacac cctcatgatc tcccggaccc ctgaggtcac atgcgtggtg    420
gtggacgtga gccacgaaga ccctgaggtc aagttcaact ggtacgtgga cggcgtggag    480
```

```
gtgcataatg ccaagacaaa gccgcgggag gagcagtaca acagcacgta ccgggtggtc      540
agcgtcctca ccgtcctgca ccaggactgg ctgaatggca aggagtacaa gtgcaaggtc      600
tccaacaaag ccctcccagc ccccatcgag aaaaccatct ccaaagccaa agggcagccc      660
cgagaaccac aggtgtacac cctgccccca tcccgggagg agatgaccaa gaaccaggtc      720
agcctgacct gcctggtcaa aggcttctat cccagcgaca tcgccgtgga gtgggagagc      780
aatgggcagc cggagaacaa ctacaagacc acgcctcccg tgctggactc cgacggctcc      840
ttcttcctct acagcaagct caccgtggac aagagcaggt ggcagcaggg gaacgtcttc      900
tcatgctccg tgatgcatga ggctctgcac aaccactaca cgcagaagag cctctccctg      960
tctccgggta aa                                                          972

<210> SEQ ID NO 20
<211> LENGTH: 957
<212> TYPE: DNA
<213> ORGANISM: Artificial Sequence
<220> FEATURE:
<223> OTHER INFORMATION: DNA encoding a mutated human IGF-1 protein:
      hIgF1-Ea-Fc_mut 04/2_A

<400> SEQUENCE: 20
acgctctgcg gggctgagct ggtggatgct cttcagttcg tgtgtggaga caggggcttt      60
tatttcaaca agcccacagg gtatggctcc agcagtcggg aggcgcctca gacaagcatc      120
gtggatgagt gctgcttccg gagctgtgat ctaaggaggc tggagatgta ttgcgcaccc      180
ctcaagcctg ccgtccaggc ccagcagcac accgacatgc ccaagaccca gaaggaagta      240
catttgaaga acgcaagtag agggagtgca ggaaacaaga actaccagat gtgccaccg      300 tgcccagcac ctgaagcagc gggggacccg tcagtcttcc tcttcccccc aaaacccaag      360
gacaccctca tgatctcccg gacccctgag gtcacatgcg tggtggtgga cgtgagccac      420
gaagaccctg aggtcaagtt caactggtac gtggacggcg tggaggtgca taatgccaag      480
acaaagccgc gggaggagca gtacaacagc acgtaccggg tggtcagcgt cctcaccgtc      540
ctgcaccagg actggctgaa tgcaaggag tacaagtgca aggtctccaa caaagccctc      600
ccagccccca tcgagaaaac catctccaaa gccaagggc agccccgaga accacaggtg      660
tacaccctgc cccatcccg ggaggagatg accaagaacc aggtcagcct gacctgcctg      720
gtcaaaggct tctatcccag cgacatcgcc gtggagtggg agagcaatgg gcagccggag      780
aacaactaca agaccacgcc tcccgtgctg gactccgacg gctccttctt cctctacagc      840
aagctcaccg tggacaagag caggtggcag caggggaacg tcttctcatg ctccgtgatg      900
catgaggctc tgcacaacca ctacacgcag aagagcctct ccctgtctcc gggtaaa       957

<210> SEQ ID NO 21
<211> LENGTH: 942
<212> TYPE: DNA
<213> ORGANISM: Artificial Sequence
<220> FEATURE:
<223> OTHER INFORMATION: DNA encoding a mutated human IGF-1 protein:
      hIgF1-Ea-Fc_mut 04/2_F

<400> SEQUENCE: 21
acgctctgcg gggctgagct ggtggatgct cttcagttcg tgtgtggaga caggggcttt      60
tatttcaaca agcccacagg gtatggctcc agcagtcggg aggcgcctca gacaagcatc      120
gtggatgagt gctgcttccg gagctgtgat ctaaggaggc tggagatgta ttgcgcaccc      180
```

```
ctcaagcctg ccgtccaggc ccagcagcac accgacatgc ccaagaccca gaaggaagta    240
catttgaaga acgcaagtgg ggacaaaact cacacatgcc caccgtgccc agcacctgaa    300
gcagcggggg gaccgtcagt cttcctcttc cccccaaaac ccaaggacac cctcatgatc    360
tcccggaccc ctgaggtcac atgcgtggtg gtggacgtga gccacgaaga ccctgaggtc    420
aagttcaact ggtacgtgga cggcgtggag gtgcataatg ccaagacaaa gccgcgggag    480
gagcagtaca acagcacgta ccgggtggtc agcgtcctca ccgtcctgca ccaggactgg    540
ctgaatggca aggagtacaa gtgcaaggtc tccaacaaag ccctcccagc ccccatcgag    600
aaaaccatct ccaaagccaa agggcagccc cgagaaccac aggtgtacac cctgcccccca   660 tcccgggagg agatgaccaa gaaccaggtc agcctgacct gcctggtcaa aggcttctat    720
cccagcgaca tcgccgtgga gtgggagagc aatgggcagc cggagaacaa ctacaagacc    780
acgcctcccg tgctggactc cgacggctcc ttcttcctct acagcaagct caccgtggac    840
aagagcaggt ggcagcaggg gaacgtcttc tcatgctccg tgatgcatga ggctctgcac    900
aaccactaca cgcagaagag cctctccctg tctccgggta aa                      942
```

<210> SEQ ID NO 22
<211> LENGTH: 6
<212> TYPE: PRT
<213> ORGANISM: Artificial Sequence
<220> FEATURE:
<223> OTHER INFORMATION: artificial peptide hinge region

<400> SEQUENCE: 22

Cys Pro Pro Cys Pro Ala
1               5

<210> SEQ ID NO 23
<211> LENGTH: 11
<212> TYPE: PRT
<213> ORGANISM: Artificial Sequence
<220> FEATURE:
<223> OTHER INFORMATION: artificial peptide hinge region

<400> SEQUENCE: 23

Asp Lys Thr His Thr Cys Pro Pro Cys Pro Ala
1               5                   10

<210> SEQ ID NO 24
<211> LENGTH: 16
<212> TYPE: PRT
<213> ORGANISM: Artificial Sequence
<220> FEATURE:
<223> OTHER INFORMATION: artificial peptide hinge region

<400> SEQUENCE: 24

Glu Pro Lys Ser Cys Asp Lys Thr His Thr Cys Pro Pro Cys Pro Ala
1               5                   10                  15

<210> SEQ ID NO 25
<211> LENGTH: 23
<212> TYPE: PRT
<213> ORGANISM: Artificial Sequence
<220> FEATURE:
<223> OTHER INFORMATION: mutated human IGF-1 Ea peptide

<400> SEQUENCE: 25

Val Gln Ala Gln Gln His Thr Asp Met Pro Lys Thr Gln Lys Glu Val
1               5                   10                  15

His Leu Lys Asn Ala Ser Gly

<210> SEQ ID NO 26
<211> LENGTH: 32
<212> TYPE: PRT
<213> ORGANISM: Artificial Sequence
<220> FEATURE:
<223> OTHER INFORMATION: mutated human IGF-1 E peptide

<400> SEQUENCE: 26

```
Val Gln Ala Gln Gln His Thr Asp Met Pro Lys Thr Gln Lys Tyr Gln
1               5                   10                  15

Pro Pro Ala Thr Asn Lys Asn Thr Lys Ser Gln Arg Arg Lys Gly Ser
            20                  25                  30
```

<210> SEQ ID NO 27
<211> LENGTH: 102
<212> TYPE: PRT
<213> ORGANISM: Artificial Sequence
<220> FEATURE:
<223> OTHER INFORMATION: Mutated human IGF-1 protein: hIGF1-Ea-mut 03

<400> SEQUENCE: 27

```
Gly Pro Thr Leu Cys Gly Ala Glu Leu Val Asp Ala Leu Gln Phe Val
1               5                   10                  15

Cys Gly Asp Arg Gly Phe Tyr Phe Asn Lys Pro Thr Gly Tyr Gly Ser
            20                  25                  30

Ser Ser Arg Ala Ala Pro Gln Thr Gly Ile Val Asp Glu Cys Cys Phe
        35                  40                  45

Arg Ser Cys Asp Leu Arg Arg Leu Glu Met Tyr Cys Ala Pro Leu Lys
50                  55                  60

Pro Ala Lys Ser Ala Val Arg Ala Gln Arg His Thr Asp Met Pro Lys
65                  70                  75                  80

Thr Gln Lys Glu Val His Leu Lys Asn Ala Ser Arg Gly Ser Ala Gly
                85                  90                  95

Asn Lys Asn Tyr Arg Met
            100
```

<210> SEQ ID NO 28
<211> LENGTH: 306
<212> TYPE: PRT
<213> ORGANISM: Artificial Sequence
<220> FEATURE:
<223> OTHER INFORMATION: DNA encoding the mutated human IGF-1 protein: hIGF1-Ea-mut 03

<400> SEQUENCE: 28

```
Gly Gly Ala Cys Cys Gly Ala Cys Gly Cys Thr Cys Thr Gly Cys Gly
1               5                   10                  15

Gly Gly Gly Cys Thr Gly Ala Gly Cys Thr Gly Gly Thr Gly Gly Ala
            20                  25                  30

Thr Gly Cys Thr Cys Thr Thr Cys Ala Gly Thr Thr Cys Gly Thr Gly
        35                  40                  45

Thr Gly Thr Gly Gly Ala Gly Ala Cys Ala Gly Gly Gly Gly Cys Thr
50                  55                  60

Thr Thr Thr Ala Thr Thr Thr Cys Ala Ala Cys Ala Ala Gly Cys Cys
65                  70                  75                  80

Cys Ala Cys Ala Gly Gly Gly Thr Ala Thr Gly Gly Cys Thr Cys Cys
                85                  90                  95

Ala Gly Cys Ala Gly Thr Cys Gly Gly Gly Cys Gly Gly Cys Gly Cys
```

```
                100                 105                 110
Cys Thr Cys Ala Gly Ala Cys Ala Gly Gly Cys Ala Thr Cys Gly Thr
            115                 120                 125
Gly Gly Ala Thr Gly Ala Gly Thr Gly Cys Thr Gly Cys Thr Thr Cys
        130                 135                 140
Cys Gly Gly Ala Gly Cys Thr Gly Thr Gly Ala Thr Cys Thr Ala Ala
145                 150                 155                 160
Gly Gly Ala Gly Gly Cys Thr Gly Gly Ala Gly Ala Thr Gly Thr Ala
                165                 170                 175
Thr Thr Gly Cys Gly Cys Ala Cys Cys Cys Thr Cys Ala Ala Gly
            180                 185                 190
Cys Cys Thr Gly Cys Cys Ala Ala Gly Thr Cys Ala Gly Cys Thr Gly
        195                 200                 205
Thr Cys Cys Gly Thr Gly Cys Cys Cys Ala Gly Cys Gly Cys Cys Ala
    210                 215                 220
Cys Ala Cys Cys Gly Ala Cys Ala Thr Gly Cys Cys Cys Ala Ala Gly
225                 230                 235                 240
Ala Cys Cys Cys Ala Gly Ala Ala Gly Gly Ala Ala Gly Thr Ala Cys
                245                 250                 255
Ala Thr Thr Thr Gly Ala Ala Gly Ala Ala Cys Gly Cys Ala Ala Gly
            260                 265                 270
Thr Ala Gly Ala Gly Gly Ala Gly Thr Gly Cys Ala Gly Gly Ala
        275                 280                 285
Ala Ala Cys Ala Ala Gly Ala Ala Cys Thr Ala Cys Ala Gly Gly Ala
    290                 295                 300
Thr Gly
305

<210> SEQ ID NO 29
<211> LENGTH: 329
<212> TYPE: PRT
<213> ORGANISM: Artificial Sequence
<220> FEATURE:
<223> OTHER INFORMATION: Mutated human IGF-1 protein: hIgF1-Ea-Fc_mut 02

<400> SEQUENCE: 29

Thr Leu Cys Gly Ala Glu Leu Val Asp Ala Leu Gln Phe Val Cys Gly
1               5                   10                  15
Asp Arg Gly Phe Tyr Phe Asn Lys Pro Thr Gly Tyr Gly Ser Ser Ser
                20                  25                  30
Arg Ala Ala Pro Gln Thr Ser Ile Val Asp Glu Cys Cys Phe Arg Ser
        35                  40                  45
Cys Asp Leu Arg Arg Leu Glu Met Tyr Cys Ala Pro Leu Lys Pro Ala
    50                  55                  60
Lys Ser Ala Val Gln Ala Gln His Thr Asp Met Pro Lys Thr Gln
65                  70                  75                  80
Lys Glu Val His Leu Lys Asn Ala Ser Arg Gly Ser Ala Gly Asn Lys
                85                  90                  95
Asn Tyr Gln Met Gly Ser Asp Lys Thr His Thr Cys Pro Pro Cys Pro
            100                 105                 110
Ala Pro Glu Ala Ala Gly Gly Pro Ser Val Phe Leu Phe Pro Pro Lys
        115                 120                 125
Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
```

```
                145                 150                 155                 160
Val Asp Gly Val Glu Val His Asn Ala Lys Thr Lys Pro Arg Glu Glu
                    165                 170                 175

Gln Tyr Asn Ser Thr Tyr Arg Val Val Ser Val Leu Thr Val Leu His
                    180                 185                 190

Gln Asp Trp Leu Asn Gly Lys Glu Tyr Lys Cys Lys Val Ser Asn Lys
                    195                 200                 205

Ala Leu Pro Ala Pro Ile Glu Lys Thr Ile Ser Lys Ala Lys Gly Gln
            210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                    245                 250                 255

Ser Asp Ile Ala Val Glu Trp Glu Ser Asn Gly Gln Pro Glu Asn Asn
                    260                 265                 270

Tyr Lys Thr Thr Pro Pro Val Leu Asp Ser Asp Gly Ser Phe Phe Leu
                    275                 280                 285

Tyr Ser Lys Leu Thr Val Asp Lys Ser Arg Trp Gln Gln Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                    325
```

<210> SEQ ID NO 30
<211> LENGTH: 329
<212> TYPE: PRT
<213> ORGANISM: Artificial Sequence
<220> FEATURE:
<223> OTHER INFORMATION: Mutated human IGF-1 protein: hIgF1-Ea-Fc_mut 04

<400> SEQUENCE: 30

```
Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
                20                  25                  30

Arg Glu Ala Pro Gln Thr Gly Ile Val Asp Glu Cys Cys Phe Arg Ser
            35                  40                  45

Cys Asp Leu Arg Arg Leu Glu Met Tyr Cys Ala Pro Leu Lys Pro Ala
50                  55                  60

Lys Ser Ala Val Gln Ala Gln His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Gln Met Gly Ser Asp Lys Thr His Thr Cys Pro Pro Cys Pro
                100                 105                 110

Ala Pro Glu Ala Ala Gly Gly Pro Ser Val Phe Leu Phe Pro Pro Lys
            115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                    165                 170                 175

Gln Tyr Asn Ser Thr Tyr Arg Val Val Ser Val Leu Thr Val Leu His
```

```
              180                 185                 190
Gln Asp Trp Leu Asn Gly Lys Glu Tyr Lys Cys Lys Val Ser Asn Lys
            195                 200                 205

Ala Leu Pro Ala Pro Ile Glu Lys Thr Ile Ser Lys Ala Lys Gly Gln
        210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 31
<211> LENGTH: 329
<212> TYPE: PRT
<213> ORGANISM: Artificial Sequence
<220> FEATURE:
<223> OTHER INFORMATION: Mutated human IGF-1 protein: hIgF1-Ea-Fc_mut 13

<400> SEQUENCE: 31

Thr Leu Cys Gly Ala Glu Leu Val Asp Ala Leu Gln Phe Val Cys Gly
1               5                  10                  15

Asp Arg Gly Phe Tyr Phe Asn Lys Pro Thr Gly Tyr Gly Ser Ser Ser
            20                  25                  30

Gln Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Val Gln Ala Gln His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Gln Met Gly Ser Asp Lys Thr His Thr Cys Pro Pro Cys Pro
            100                 105                 110

Ala Pro Glu Ala Ala Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
```

```
                 210                 215                 220
Pro Arg Glu Pro Gln Val Tyr Thr Leu Pro Pro Ser Arg Glu Met
225                 230                 235                 240

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 32
<211> LENGTH: 100
<212> TYPE: PRT
<213> ORGANISM: Artificial Sequence
<220> FEATURE:
<223> OTHER INFORMATION: Mutated human IGF-1 protein: Example 8

<400> SEQUENCE: 32

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
                20                  25                  30

Gln Arg Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
        50                  55                  60

Lys Ser Ala Val Arg Ala Gln Arg His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Arg Met
            100

<210> SEQ ID NO 33
<211> LENGTH: 100
<212> TYPE: PRT
<213> ORGANISM: Artificial Sequence
<220> FEATURE:
<223> OTHER INFORMATION: Mutated human IGF-1 protein: Example 9

<400> SEQUENCE: 33

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
                20                  25                  30

Arg Glu Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
        50                  55                  60

Lys Ser Ala Val Arg Ala Gln Arg His Thr Asp Met Pro Lys Thr Gln
65                  70                  75                  80
```

```
Lys Glu Val His Leu Lys Asn Ala Ser Arg Gly Ser Ala Gly Asn Lys
                85                  90                  95

Asn Tyr Arg Met
            100

<210> SEQ ID NO 34
<211> LENGTH: 100
<212> TYPE: PRT
<213> ORGANISM: Artificial Sequence
<220> FEATURE:
<223> OTHER INFORMATION: Mutated human IGF-1 protein: Example 10

<400> SEQUENCE: 34

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
                20                  25                  30

Arg Ala Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
        50                  55                  60

Lys Ser Ala Val Arg Ala Gln Arg His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Arg Met
            100

<210> SEQ ID NO 35
<211> LENGTH: 100
<212> TYPE: PRT
<213> ORGANISM: Artificial Sequence
<220> FEATURE:
<223> OTHER INFORMATION: Mutated human IGF-1 protein: Example 11

<400> SEQUENCE: 35

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
                20                  25                  30

Arg Pro Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
        50                  55                  60

Lys Ser Ala Val Arg Ala Gln Arg His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Arg Met
            100

<210> SEQ ID NO 36
<211> LENGTH: 100
<212> TYPE: PRT
<213> ORGANISM: Artificial Sequence
<220> FEATURE:
<223> OTHER INFORMATION: Mutated human IGF-1 protein: Example 12

<400> SEQUENCE: 36

Thr Leu Cys Gly Ala Glu Leu Val Asp Ala Leu Gln Phe Val Cys Gly
```

```
1               5                   10                  15
Asp Arg Gly Phe Tyr Phe Asn Lys Pro Thr Gly Tyr Gly Ser Ser Ser
            20                  25                  30

Gln Gln Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
 50                  55                  60

Lys Ser Ala Val Arg Ala Gln Arg His Thr Asp Met Pro Lys Thr Gln
 65                  70                  75                  80

Lys Glu Val His Leu Lys Asn Ala Ser Arg Gly Ser Ala Gly Asn Lys
                85                  90                  95

Asn Tyr Arg Met
            100

<210> SEQ ID NO 37
<211> LENGTH: 100
<212> TYPE: PRT
<213> ORGANISM: Artificial Sequence
<220> FEATURE:
<223> OTHER INFORMATION: Mutated human IGF-1 protein: Example 13

<400> SEQUENCE: 37

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Ala Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
 50                  55                  60

Lys Ser Ala Val Arg Ala Gln Arg His Thr Asp Met Pro Lys Thr Gln
 65                  70                  75                  80

Lys Glu Val His Leu Lys Asn Ala Ser Arg Gly Ser Ala Gly Asn Lys
                85                  90                  95

Asn Tyr Arg Met
            100

<210> SEQ ID NO 38
<211> LENGTH: 100
<212> TYPE: PRT
<213> ORGANISM: Artificial Sequence
<220> FEATURE:
<223> OTHER INFORMATION: Mutated human IGF-1 protein: Example 14

<400> SEQUENCE: 38

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Arg Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
 50                  55                  60

Lys Ser Ala Val Gln Ala Gln Arg His Thr Asp Met Pro Lys Thr Gln
 65                  70                  75                  80

Lys Glu Val His Leu Lys Asn Ala Ser Arg Gly Ser Ala Gly Asn Lys
                85                  90                  95
```

Asn Tyr Arg Met
            100

<210> SEQ ID NO 39
<211> LENGTH: 100
<212> TYPE: PRT
<213> ORGANISM: Artificial Sequence
<220> FEATURE:
<223> OTHER INFORMATION: Mutated human IGF-1 protein: Example 15

<400> SEQUENCE: 39

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Arg Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Val Gln Ala Gln Gln His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Arg Met
            100

<210> SEQ ID NO 40
<211> LENGTH: 100
<212> TYPE: PRT
<213> ORGANISM: Artificial Sequence
<220> FEATURE:
<223> OTHER INFORMATION: Mutated human IGF-1 protein: Example 16

<400> SEQUENCE: 40

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Arg Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Val Gln Ala Gln Gln His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Gln Met
            100

<210> SEQ ID NO 41
<211> LENGTH: 100
<212> TYPE: PRT
<213> ORGANISM: Artificial Sequence
<220> FEATURE:
<223> OTHER INFORMATION: Mutated human IGF-1 protein: Example 17

<400> SEQUENCE: 41

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser

```
                 20                  25                  30

Arg Glu Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
        50                  55                  60

Lys Ser Ala Val Arg Ala Gln Gln His Thr Asp Met Pro Lys Thr Gln
 65                  70                  75                  80

Lys Glu Val His Leu Lys Asn Ala Ser Arg Gly Ser Ala Gly Asn Lys
                85                  90                  95

Asn Tyr Arg Met
            100

<210> SEQ ID NO 42
<211> LENGTH: 100
<212> TYPE: PRT
<213> ORGANISM: Artificial Sequence
<220> FEATURE:
<223> OTHER INFORMATION: Mutated human IGF-1 protein: Example 18

<400> SEQUENCE: 42

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Glu Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Val Gln Ala Gln Gln His Thr Asp Met Pro Lys Thr Gln
 65                  70                  75                  80

Lys Glu Val His Leu Lys Asn Ala Ser Arg Gly Ser Ala Gly Asn Lys
                85                  90                  95

Asn Tyr Arg Met
            100

<210> SEQ ID NO 43
<211> LENGTH: 100
<212> TYPE: PRT
<213> ORGANISM: Artificial Sequence
<220> FEATURE:
<223> OTHER INFORMATION: Mutated human IGF-1 protein: Example 19

<400> SEQUENCE: 43

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Glu Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Val Gln Ala Gln Gln His Thr Asp Met Pro Lys Thr Gln
 65                  70                  75                  80

Lys Glu Val His Leu Lys Asn Ala Ser Arg Gly Ser Ala Gly Asn Lys
                85                  90                  95

Asn Tyr Gln Met
            100
```

```
<210> SEQ ID NO 44
<211> LENGTH: 100
<212> TYPE: PRT
<213> ORGANISM: Artificial Sequence
<220> FEATURE:
<223> OTHER INFORMATION: Mutated human IGF-1 protein: Example 20

<400> SEQUENCE: 44

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Ala Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Val Gln Ala Gln Arg His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Arg Met
            100

<210> SEQ ID NO 45
<211> LENGTH: 100
<212> TYPE: PRT
<213> ORGANISM: Artificial Sequence
<220> FEATURE:
<223> OTHER INFORMATION: Mutated human IGF-1 protein: Example 21

<400> SEQUENCE: 45

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Ala Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Val Gln Ala Gln His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Arg Met
            100

<210> SEQ ID NO 46
<211> LENGTH: 100
<212> TYPE: PRT
<213> ORGANISM: Artificial Sequence
<220> FEATURE:
<223> OTHER INFORMATION: Mutated human IGF-1 protein: Example 22

<400> SEQUENCE: 46

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Ala Ala Pro Gln Thr Ser Ile Val Asp Glu Cys Cys Phe Arg Ser
```

35                  40                  45

Cys Asp Leu Arg Arg Leu Glu Met Tyr Cys Ala Pro Leu Lys Pro Ala
        50                  55                  60

Lys Ser Ala Val Gln Ala Gln Gln His Thr Asp Met Pro Lys Thr Gln
 65                  70                  75                  80

Lys Glu Val His Leu Lys Asn Ala Ser Arg Gly Ser Ala Gly Asn Lys
                85                  90                  95

Asn Tyr Gln Met
            100

<210> SEQ ID NO 47
<211> LENGTH: 100
<212> TYPE: PRT
<213> ORGANISM: Artificial Sequence
<220> FEATURE:
<223> OTHER INFORMATION: Mutated human IGF-1 protein: Example 23

<400> SEQUENCE: 47

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
                20                  25                  30

Arg Pro Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
        50                  55                  60

Lys Ser Ala Val Gln Ala Gln Arg His Thr Asp Met Pro Lys Thr Gln
 65                  70                  75                  80

Lys Glu Val His Leu Lys Asn Ala Ser Arg Gly Ser Ala Gly Asn Lys
                85                  90                  95

Asn Tyr Arg Met
            100

<210> SEQ ID NO 48
<211> LENGTH: 100
<212> TYPE: PRT
<213> ORGANISM: Artificial Sequence
<220> FEATURE:
<223> OTHER INFORMATION: Mutated human IGF-1 protein: Example 24

<400> SEQUENCE: 48

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
                20                  25                  30

Arg Pro Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
        50                  55                  60

Lys Ser Ala Val Gln Ala Gln Gln His Thr Asp Met Pro Lys Thr Gln
 65                  70                  75                  80

Lys Glu Val His Leu Lys Asn Ala Ser Arg Gly Ser Ala Gly Asn Lys
                85                  90                  95

Asn Tyr Arg Met
            100

<210> SEQ ID NO 49
<211> LENGTH: 100

```
<212> TYPE: PRT
<213> ORGANISM: Artificial Sequence
<220> FEATURE:
<223> OTHER INFORMATION: Mutated human IGF-1 protein: Example 25

<400> SEQUENCE: 49

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Pro Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Val Gln Ala Gln Gln His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Gln Met
            100

<210> SEQ ID NO 50
<211> LENGTH: 100
<212> TYPE: PRT
<213> ORGANISM: Artificial Sequence
<220> FEATURE:
<223> OTHER INFORMATION: Mutated human IGF-1 protein: Example 26

<400> SEQUENCE: 50

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Gln Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Val Gln Ala Gln Arg His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Arg Met
            100

<210> SEQ ID NO 51
<211> LENGTH: 100
<212> TYPE: PRT
<213> ORGANISM: Artificial Sequence
<220> FEATURE:
<223> OTHER INFORMATION: Mutated human IGF-1 protein: Example 27

<400> SEQUENCE: 51

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Gln Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
```

```
                50              55                  60
Lys Ser Ala Val Gln Ala Gln Gln His Thr Asp Met Pro Lys Thr Gln
 65                  70                  75                  80

Lys Glu Val His Leu Lys Asn Ala Ser Arg Gly Ser Ala Gly Asn Lys
                 85                  90                  95

Asn Tyr Arg Met
            100

<210> SEQ ID NO 52
<211> LENGTH: 100
<212> TYPE: PRT
<213> ORGANISM: Artificial Sequence
<220> FEATURE:
<223> OTHER INFORMATION: Mutated human IGF-1 protein: Example 28

<400> SEQUENCE: 52

Thr Leu Cys Gly Ala Glu Leu Val Asp Ala Leu Gln Phe Val Cys Gly
  1               5                  10                  15

Asp Arg Gly Phe Tyr Phe Asn Lys Pro Thr Gly Tyr Gly Ser Ser Ser
                 20                  25                  30

Gln Ala Ala Pro Gln Thr Ser Ile Val Asp Glu Cys Cys Phe Arg Ser
             35                  40                  45

Cys Asp Leu Arg Arg Leu Glu Met Tyr Cys Ala Pro Leu Lys Pro Ala
 50                  55                  60

Lys Ser Ala Val Gln Ala Gln Gln His Thr Asp Met Pro Lys Thr Gln
 65                  70                  75                  80

Lys Glu Val His Leu Lys Asn Ala Ser Arg Gly Ser Ala Gly Asn Lys
                 85                  90                  95

Asn Tyr Arg Met
            100

<210> SEQ ID NO 53
<211> LENGTH: 100
<212> TYPE: PRT
<213> ORGANISM: Artificial Sequence
<220> FEATURE:
<223> OTHER INFORMATION: Mutated human IGF-1 protein: Example 29

<400> SEQUENCE: 53

Thr Leu Cys Gly Ala Glu Leu Val Asp Ala Leu Gln Phe Val Cys Gly
  1               5                  10                  15

Asp Arg Gly Phe Tyr Phe Asn Lys Pro Thr Gly Tyr Gly Ser Ser Ser
                 20                  25                  30

Gln Gln Ala Pro Gln Thr Ser Ile Val Asp Glu Cys Cys Phe Arg Ser
             35                  40                  45

Cys Asp Leu Arg Arg Leu Glu Met Tyr Cys Ala Pro Leu Lys Pro Ala
 50                  55                  60

Lys Ser Ala Val Gln Ala Gln Gln His Thr Asp Met Pro Lys Thr Gln
 65                  70                  75                  80

Lys Glu Val His Leu Lys Asn Ala Ser Arg Gly Ser Ala Gly Asn Lys
                 85                  90                  95

Asn Tyr Gln Met
            100

<210> SEQ ID NO 54
<211> LENGTH: 100
<212> TYPE: PRT
<213> ORGANISM: Artificial Sequence
<220> FEATURE:
```

<223> OTHER INFORMATION: Mutated human IGF-1 protein: Example 30

<400> SEQUENCE: 54

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Ala Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Val Gln Ala Gln Gln His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Gln Met
                100

<210> SEQ ID NO 55
<211> LENGTH: 97
<212> TYPE: PRT
<213> ORGANISM: Artificial Sequence
<220> FEATURE:
<223> OTHER INFORMATION: Mutated human IGF-1 protein: Example 31

<400> SEQUENCE: 55

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Arg Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Val Arg Ala Gln Arg His Thr Asp Met Pro Lys Thr Gln Lys Glu Val
65                  70                  75                  80

His Leu Lys Asn Ala Ser Arg Gly Ser Ala Gly Asn Lys Asn Tyr Arg
                85                  90                  95

Met

<210> SEQ ID NO 56
<211> LENGTH: 97
<212> TYPE: PRT
<213> ORGANISM: Artificial Sequence
<220> FEATURE:
<223> OTHER INFORMATION: Mutated human IGF-1 protein: Example 32

<400> SEQUENCE: 56

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Glu Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Val Arg Ala Gln Arg His Thr Asp Met Pro Lys Thr Gln Lys Glu Val
65                  70                  75                  80

His Leu Lys Asn Ala Ser Arg Gly Ser Ala Gly Asn Lys Asn Tyr Arg
            85                  90                  95

Met

<210> SEQ ID NO 57
<211> LENGTH: 97
<212> TYPE: PRT
<213> ORGANISM: Artificial Sequence
<220> FEATURE:
<223> OTHER INFORMATION: Mutated human IGF-1 protein: Example 33

<400> SEQUENCE: 57

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Ala Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Val Arg Ala Gln Arg His Thr Asp Met Pro Lys Thr Gln Lys Glu Val
65                  70                  75                  80

His Leu Lys Asn Ala Ser Arg Gly Ser Ala Gly Asn Lys Asn Tyr Arg
            85                  90                  95

Met

<210> SEQ ID NO 58
<211> LENGTH: 97
<212> TYPE: PRT
<213> ORGANISM: Artificial Sequence
<220> FEATURE:
<223> OTHER INFORMATION: Mutated human IGF-1 protein: Example 34

<400> SEQUENCE: 58

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Pro Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Val Arg Ala Gln Arg His Thr Asp Met Pro Lys Thr Gln Lys Glu Val
65                  70                  75                  80

His Leu Lys Asn Ala Ser Arg Gly Ser Ala Gly Asn Lys Asn Tyr Arg
            85                  90                  95

Met

<210> SEQ ID NO 59
<211> LENGTH: 98
<212> TYPE: PRT
<213> ORGANISM: Artificial Sequence
<220> FEATURE:
<223> OTHER INFORMATION: Mutated human IGF-1 protein: Example 35

<400> SEQUENCE: 59

Thr Leu Cys Gly Ala Glu Leu Val Asp Ala Leu Gln Phe Val Cys Gly
1               5                   10                  15

```
Asp Arg Gly Phe Tyr Phe Asn Lys Pro Thr Gly Tyr Gly Ser Ser
            20                  25                  30

Gln Gln Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
50                  55                  60

Gln Val Arg Ala Gln Arg His Thr Asp Met Pro Lys Thr Gln Lys Glu
65                  70                  75                  80

Val His Leu Lys Asn Ala Ser Arg Gly Ser Ala Gly Asn Lys Asn Tyr
                85                  90                  95

Arg Met

<210> SEQ ID NO 60
<211> LENGTH: 97
<212> TYPE: PRT
<213> ORGANISM: Artificial Sequence
<220> FEATURE:
<223> OTHER INFORMATION: Mutated human IGF-1 protein: Example 36

<400> SEQUENCE: 60

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Ala Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Val Arg Ala Gln Arg His Thr Asp Met Pro Lys Thr Gln Lys Glu Val
65                  70                  75                  80

His Leu Lys Asn Ala Ser Arg Gly Ser Ala Gly Asn Lys Asn Tyr Arg
                85                  90                  95

Met

<210> SEQ ID NO 61
<211> LENGTH: 97
<212> TYPE: PRT
<213> ORGANISM: Artificial Sequence
<220> FEATURE:
<223> OTHER INFORMATION: Mutated human IGF-1 protein: Example 37

<400> SEQUENCE: 61

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Arg Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Val Gln Ala Gln Arg His Thr Asp Met Pro Lys Thr Gln Lys Glu Val
65                  70                  75                  80

His Leu Lys Asn Ala Ser Arg Gly Ser Ala Gly Asn Lys Asn Tyr Arg
                85                  90                  95

Met

<210> SEQ ID NO 62
```

```
<211> LENGTH: 97
<212> TYPE: PRT
<213> ORGANISM: Artificial Sequence
<220> FEATURE:
<223> OTHER INFORMATION: Mutated human IGF-1 protein: Example 38

<400> SEQUENCE: 62

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Gln Arg Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Val Gln Ala Gln Gln His Thr Asp Met Pro Lys Thr Gln Lys Glu Val
65                  70                  75                  80

His Leu Lys Asn Ala Ser Arg Gly Ser Ala Gly Asn Lys Asn Tyr Arg
                85                  90                  95

Met

<210> SEQ ID NO 63
<211> LENGTH: 97
<212> TYPE: PRT
<213> ORGANISM: Artificial Sequence
<220> FEATURE:
<223> OTHER INFORMATION: Mutated human IGF-1 protein: Example 39

<400> SEQUENCE: 63

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Gln Arg Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Val Gln Ala Gln Gln His Thr Asp Met Pro Lys Thr Gln Lys Glu Val
65                  70                  75                  80

His Leu Lys Asn Ala Ser Arg Gly Ser Ala Gly Asn Lys Asn Tyr Gln
                85                  90                  95

Met

<210> SEQ ID NO 64
<211> LENGTH: 97
<212> TYPE: PRT
<213> ORGANISM: Artificial Sequence
<220> FEATURE:
<223> OTHER INFORMATION: Mutated human IGF-1 protein: Example 40

<400> SEQUENCE: 64

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Glu Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60
```

```
Val Gln Ala Gln Arg His Thr Asp Met Pro Lys Thr Gln Lys Glu Val
 65                  70                  75                  80

His Leu Lys Asn Ala Ser Arg Gly Ser Ala Gly Asn Lys Asn Tyr Arg
                 85                  90                  95

Met
```

<210> SEQ ID NO 65
<211> LENGTH: 97
<212> TYPE: PRT
<213> ORGANISM: Artificial Sequence
<220> FEATURE:
<223> OTHER INFORMATION: Mutated human IGF-1 protein: Example 41

<400> SEQUENCE: 65

```
Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
                 20                  25                  30

Arg Glu Ala Pro Gln Thr Ser Ile Val Asp Glu Cys Cys Phe Arg Ser
             35                  40                  45

Cys Asp Leu Arg Arg Leu Glu Met Tyr Cys Ala Pro Leu Lys Pro Ala
 50                  55                  60

Val Gln Ala Gln Gln His Thr Asp Met Pro Lys Thr Gln Lys Glu Val
 65                  70                  75                  80

His Leu Lys Asn Ala Ser Arg Gly Ser Ala Gly Asn Lys Asn Tyr Arg
                 85                  90                  95

Met
```

<210> SEQ ID NO 66
<211> LENGTH: 97
<212> TYPE: PRT
<213> ORGANISM: Artificial Sequence
<220> FEATURE:
<223> OTHER INFORMATION: Mutated human IGF-1 protein: Example 42

<400> SEQUENCE: 66

```
Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
                 20                  25                  30

Arg Glu Ala Pro Gln Thr Ser Ile Val Asp Glu Cys Cys Phe Arg Ser
             35                  40                  45

Cys Asp Leu Arg Arg Leu Glu Met Tyr Cys Ala Pro Leu Lys Pro Ala
 50                  55                  60

Val Gln Ala Gln Gln His Thr Asp Met Pro Lys Thr Gln Lys Glu Val
 65                  70                  75                  80

His Leu Lys Asn Ala Ser Arg Gly Ser Ala Gly Asn Lys Asn Tyr Gln
                 85                  90                  95

Met
```

<210> SEQ ID NO 67
<211> LENGTH: 97
<212> TYPE: PRT
<213> ORGANISM: Artificial Sequence
<220> FEATURE:
<223> OTHER INFORMATION: Mutated human IGF-1 protein: Example 43

<400> SEQUENCE: 67

```
Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Ala Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Val Gln Ala Gln Arg His Thr Asp Met Pro Lys Thr Gln Lys Glu Val
 65                  70                  75                  80

His Leu Lys Asn Ala Ser Arg Gly Ser Ala Gly Asn Lys Asn Tyr Arg
                85                  90                  95

Met
```

<210> SEQ ID NO 68
<211> LENGTH: 97
<212> TYPE: PRT
<213> ORGANISM: Artificial Sequence
<220> FEATURE:
<223> OTHER INFORMATION: Mutated human IGF-1 protein: Example 44

<400> SEQUENCE: 68

```
Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Ala Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Val Gln Ala Gln Gln His Thr Asp Met Pro Lys Thr Gln Lys Glu Val
 65                  70                  75                  80

His Leu Lys Asn Ala Ser Arg Gly Ser Ala Gly Asn Lys Asn Tyr Arg
                85                  90                  95

Met
```

<210> SEQ ID NO 69
<211> LENGTH: 97
<212> TYPE: PRT
<213> ORGANISM: Artificial Sequence
<220> FEATURE:
<223> OTHER INFORMATION: Mutated human IGF-1 protein: Example 45

<400> SEQUENCE: 69

```
Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Ala Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Val Gln Ala Gln Gln His Thr Asp Met Pro Lys Thr Gln Lys Glu Val
 65                  70                  75                  80

His Leu Lys Asn Ala Ser Arg Gly Ser Ala Gly Asn Lys Asn Tyr Gln
                85                  90                  95

Met
```

```
<210> SEQ ID NO 70
<211> LENGTH: 97
<212> TYPE: PRT
<213> ORGANISM: Artificial Sequence
<220> FEATURE:
<223> OTHER INFORMATION: Mutated human IGF-1 protein: Example 46

<400> SEQUENCE: 70

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Pro Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Val Gln Ala Gln Arg His Thr Asp Met Pro Lys Thr Gln Lys Glu Val
65                  70                  75                  80

His Leu Lys Asn Ala Ser Arg Gly Ser Ala Gly Asn Lys Asn Tyr Arg
                85                  90                  95

Met

<210> SEQ ID NO 71
<211> LENGTH: 97
<212> TYPE: PRT
<213> ORGANISM: Artificial Sequence
<220> FEATURE:
<223> OTHER INFORMATION: Mutated human IGF-1 protein: Example 47

<400> SEQUENCE: 71

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Pro Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Val Gln Ala Gln Gln His Thr Asp Met Pro Lys Thr Gln Lys Glu Val
65                  70                  75                  80

His Leu Lys Asn Ala Ser Arg Gly Ser Ala Gly Asn Lys Asn Tyr Arg
                85                  90                  95

Met

<210> SEQ ID NO 72
<211> LENGTH: 97
<212> TYPE: PRT
<213> ORGANISM: Artificial Sequence
<220> FEATURE:
<223> OTHER INFORMATION: Mutated human IGF-1 protein: Example 48

<400> SEQUENCE: 72

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Pro Ala Pro Gln Thr Ser Ile Val Asp Glu Cys Cys Phe Arg Ser
        35                  40                  45
```

Cys Asp Leu Arg Arg Leu Glu Met Tyr Cys Ala Pro Leu Lys Pro Ala
        50                  55                  60

Val Gln Ala Gln Gln His Thr Asp Met Pro Lys Thr Gln Lys Glu Val
 65                  70                  75                  80

His Leu Lys Asn Ala Ser Arg Gly Ser Ala Gly Asn Lys Asn Tyr Gln
                85                  90                  95

Met

<210> SEQ ID NO 73
<211> LENGTH: 97
<212> TYPE: PRT
<213> ORGANISM: Artificial Sequence
<220> FEATURE:
<223> OTHER INFORMATION: Mutated human IGF-1 protein: Example 49

<400> SEQUENCE: 73

Thr Leu Cys Gly Ala Glu Leu Val Asp Ala Leu Gln Phe Val Cys Gly
 1               5                   10                  15

Asp Arg Gly Phe Tyr Phe Asn Lys Pro Thr Gly Tyr Gly Ser Ser Ser
                20                  25                  30

Gln Gln Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
        50                  55                  60

Val Gln Ala Gln Arg His Thr Asp Met Pro Lys Thr Gln Lys Glu Val
 65                  70                  75                  80

His Leu Lys Asn Ala Ser Arg Gly Ser Ala Gly Asn Lys Asn Tyr Arg
                85                  90                  95

Met

<210> SEQ ID NO 74
<211> LENGTH: 97
<212> TYPE: PRT
<213> ORGANISM: Artificial Sequence
<220> FEATURE:
<223> OTHER INFORMATION: Mutated human IGF-1 protein: Example 50

<400> SEQUENCE: 74

Thr Leu Cys Gly Ala Glu Leu Val Asp Ala Leu Gln Phe Val Cys Gly
 1               5                   10                  15

Asp Arg Gly Phe Tyr Phe Asn Lys Pro Thr Gly Tyr Gly Ser Ser Ser
                20                  25                  30

Gln Gln Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
        50                  55                  60

Val Gln Ala Gln Gln His Thr Asp Met Pro Lys Thr Gln Lys Glu Val
 65                  70                  75                  80

His Leu Lys Asn Ala Ser Arg Gly Ser Ala Gly Asn Lys Asn Tyr Arg
                85                  90                  95

Met

<210> SEQ ID NO 75
<211> LENGTH: 97
<212> TYPE: PRT
<213> ORGANISM: Artificial Sequence
<220> FEATURE:
<223> OTHER INFORMATION: Mutated human IGF-1 protein: Example 51

<400> SEQUENCE: 75

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Ala Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Val Gln Ala Gln Gln His Thr Asp Met Pro Lys Thr Gln Lys Glu Val
65                  70                  75                  80

His Leu Lys Asn Ala Ser Arg Gly Ser Ala Gly Asn Lys Asn Tyr Arg
                85                  90                  95

Met

<210> SEQ ID NO 76
<211> LENGTH: 97
<212> TYPE: PRT
<213> ORGANISM: Artificial Sequence
<220> FEATURE:
<223> OTHER INFORMATION: Mutated human IGF-1 protein: Example 52

<400> SEQUENCE: 76

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Gln Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Val Gln Ala Gln Gln His Thr Asp Met Pro Lys Thr Gln Lys Glu Val
65                  70                  75                  80

His Leu Lys Asn Ala Ser Arg Gly Ser Ala Gly Asn Lys Asn Tyr Gln
                85                  90                  95

Met

<210> SEQ ID NO 77
<211> LENGTH: 97
<212> TYPE: PRT
<213> ORGANISM: Artificial Sequence
<220> FEATURE:
<223> OTHER INFORMATION: Mutated human IGF-1 protein: Example 53

<400> SEQUENCE: 77

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Ala Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Val Gln Ala Gln Gln His Thr Asp Met Pro Lys Thr Gln Lys Glu Val
65                  70                  75                  80

His Leu Lys Asn Ala Ser Arg Gly Ser Ala Gly Asn Lys Asn Tyr Gln

Met

<210> SEQ ID NO 78
<211> LENGTH: 97
<212> TYPE: PRT
<213> ORGANISM: Artificial Sequence
<220> FEATURE:
<223> OTHER INFORMATION: Mutated human IGF-1 protein: hIGF1-Ea-D1-3, R36Q, D68-72, R74Q, R77Q, R104Q -fc domain

<400> SEQUENCE: 78

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
                20                  25                  30

Gln Ala Ala Pro Gln Thr Gly Ile Val Asp Glu Cys Cys Phe Arg Ser
            35                  40                  45

Cys Asp Leu Arg Arg Leu Glu Met Tyr Cys Ala Pro Leu Lys Pro Ala
    50                  55                  60

Val Gln Ala Gln Gln His Thr Asp Met Pro Lys Thr Gln Lys Glu Val
65                  70                  75                  80

His Leu Lys Asn Ala Ser Arg Gly Ser Ala Gly Asn Lys Asn Tyr Gln
                85                  90                  95

Met

<210> SEQ ID NO 79
<211> LENGTH: 97
<212> TYPE: PRT
<213> ORGANISM: Artificial Sequence
<220> FEATURE:
<223> OTHER INFORMATION: Mutated human IGF-1 protein: hIGF1-Ea-D1-3, R36Q, G42A, D68-72, R74Q, R77Q, R104Q -fc domain

<400> SEQUENCE: 79

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
                20                  25                  30

Gln Ala Ala Pro Gln Thr Ala Ile Val Asp Glu Cys Cys Phe Arg Ser
            35                  40                  45

Cys Asp Leu Arg Arg Leu Glu Met Tyr Cys Ala Pro Leu Lys Pro Ala
    50                  55                  60

Val Gln Ala Gln Gln His Thr Asp Met Pro Lys Thr Gln Lys Glu Val
65                  70                  75                  80

His Leu Lys Asn Ala Ser Arg Gly Ser Ala Gly Asn Lys Asn Tyr Gln
                85                  90                  95

Met

<210> SEQ ID NO 80
<211> LENGTH: 97
<212> TYPE: PRT
<213> ORGANISM: Artificial Sequence
<220> FEATURE:
<223> OTHER INFORMATION: Mutated human IGF-1 protein: hIGF1-Ea-D1-3, R36Q, G42Q, D68-72, R74Q, R77Q, R104Q -fc domain

<400> SEQUENCE: 80

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Ala Ala Pro Gln Thr Gln Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Val Gln Ala Gln Gln His Thr Asp Met Pro Lys Thr Gln Lys Glu Val
 65                  70                  75                  80

His Leu Lys Asn Ala Ser Arg Gly Ser Ala Gly Asn Lys Asn Tyr Gln
                85                  90                  95

Met

<210> SEQ ID NO 81
<211> LENGTH: 97
<212> TYPE: PRT
<213> ORGANISM: Artificial Sequence
<220> FEATURE:
<223> OTHER INFORMATION: Mutated human IGF-1 protein: hIGF1-Ea-D1-3,
      R36Q, G42P, D68-72, R74Q, R77Q, R104Q -fc domain

<400> SEQUENCE: 81

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Gln Ala Ala Pro Gln Thr Pro Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Val Gln Ala Gln Gln His Thr Asp Met Pro Lys Thr Gln Lys Glu Val
 65                  70                  75                  80

His Leu Lys Asn Ala Ser Arg Gly Ser Ala Gly Asn Lys Asn Tyr Gln
                85                  90                  95

Met

<210> SEQ ID NO 82
<211> LENGTH: 97
<212> TYPE: PRT
<213> ORGANISM: Artificial Sequence
<220> FEATURE:
<223> OTHER INFORMATION: Mutated human IGF-1 protein: hIGF1-Ea-D1-3,
      R36Q, G42K, D68-72, R74Q, R77Q, R104Q -fc domain

<400> SEQUENCE: 82

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Gln Ala Ala Pro Gln Thr Lys Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Val Gln Ala Gln Gln His Thr Asp Met Pro Lys Thr Gln Lys Glu Val
 65                  70                  75                  80

His Leu Lys Asn Ala Ser Arg Gly Ser Ala Gly Asn Lys Asn Tyr Gln
                85                  90                  95

Met

<210> SEQ ID NO 83
<211> LENGTH: 97
<212> TYPE: PRT
<213> ORGANISM: Artificial Sequence
<220> FEATURE:
<223> OTHER INFORMATION: Mutated human IGF-1 protein: hIGF1-Ea-D1-3,
      R36Q, G42E, D68-72, R74Q, R77Q, R104Q -fc domain

<400> SEQUENCE: 83

```
Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Ala Ala Pro Gln Thr Glu Ile Val Asp Glu Cys Cys Phe Arg Ser
        35                  40                  45

Cys Asp Leu Arg Arg Leu Glu Met Tyr Cys Ala Pro Leu Lys Pro Ala
50                  55                  60

Val Gln Ala Gln Gln His Thr Asp Met Pro Lys Thr Lys Lys Glu Val
65                  70                  75                  80

His Leu Lys Asn Ala Ser Arg Gly Ser Ala Gly Asn Lys Asn Tyr Gln
                85                  90                  95

Met
```

<210> SEQ ID NO 84
<211> LENGTH: 97
<212> TYPE: PRT
<213> ORGANISM: Artificial Sequence
<220> FEATURE:
<223> OTHER INFORMATION: Mutated human IGF-1 protein: hIGF1-Ea-D1-3,
      R36Q, G42I, D68-72, R74Q, R77Q, R104Q -fc domain

<400> SEQUENCE: 84

```
Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Ala Ala Pro Gln Thr Ile Ile Val Asp Glu Cys Cys Phe Arg Ser
        35                  40                  45

Cys Asp Leu Arg Arg Leu Glu Met Tyr Cys Ala Pro Leu Lys Pro Ala
50                  55                  60

Val Gln Ala Gln Gln His Thr Asp Met Pro Lys Thr Lys Lys Glu Val
65                  70                  75                  80

His Leu Lys Asn Ala Ser Arg Gly Ser Ala Gly Asn Lys Asn Tyr Gln
                85                  90                  95

Met
```

<210> SEQ ID NO 85
<211> LENGTH: 97
<212> TYPE: PRT
<213> ORGANISM: Artificial Sequence
<220> FEATURE:
<223> OTHER INFORMATION: Mutated human IGF-1 protein: hIGF1-Ea-D1-3,
      R36Q, G42Y, D68-72, R74Q, R77Q, R104Q -fc domain

<400> SEQUENCE: 85

```
Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30
```

```
Gln Ala Ala Pro Gln Thr Tyr Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Val Gln Ala Gln Gln His Thr Asp Met Pro Lys Thr Gln Lys Glu Val
 65                  70                  75                  80

His Leu Lys Asn Ala Ser Arg Gly Ser Ala Gly Asn Lys Asn Tyr Gln
                85                  90                  95

Met

<210> SEQ ID NO 86
<211> LENGTH: 96
<212> TYPE: PRT
<213> ORGANISM: Artificial Sequence
<220> FEATURE:
<223> OTHER INFORMATION: Mutated human IGF-1 protein: hIGF1-Ea-D1-3,
      R36Q, D42, D68-72, R74Q, R77Q, R104Q -fc domain

<400> SEQUENCE: 86

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
                20                  25                  30

Gln Ala Ala Pro Gln Thr Ile Val Asp Glu Cys Cys Phe Arg Ser Cys
        35                  40                  45

Asp Leu Arg Arg Leu Glu Met Tyr Cys Ala Pro Leu Lys Pro Ala Val
 50                  55                  60

Gln Ala Gln Gln His Thr Asp Met Pro Lys Thr Gln Lys Glu Val His
65                   70                  75                  80

Leu Lys Asn Ala Ser Arg Gly Ser Ala Gly Asn Lys Asn Tyr Gln Met
                85                  90                  95

<210> SEQ ID NO 87
<211> LENGTH: 102
<212> TYPE: PRT
<213> ORGANISM: Artificial Sequence
<220> FEATURE:
<223> OTHER INFORMATION: Mutated human IGF-1 protein: hIGF1-Ea (delGPE,
      R37A)

<400> SEQUENCE: 87

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
                20                  25                  30

Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Lys Ser Ala Arg Ser Val Arg Ala Gln Arg His Thr Asp Met Pro Lys
65                   70                  75                  80

Thr Gln Lys Glu Val His Leu Lys Asn Ala Ser Arg Gly Ser Ala Gly
                85                  90                  95

Asn Lys Asn Tyr Arg Met
                100

<210> SEQ ID NO 88
<211> LENGTH: 29
```

```
<212> TYPE: DNA
<213> ORGANISM: Artificial Sequence
<220> FEATURE:
<223> OTHER INFORMATION: PCR Primer

<400> SEQUENCE: 88
tgacactata gaataacatc cactttgcc                                        29

<210> SEQ ID NO 89
<211> LENGTH: 52
<212> TYPE: DNA
<213> ORGANISM: Artificial Sequence
<220> FEATURE:
<223> OTHER INFORMATION: PCR Primer

<400> SEQUENCE: 89
tcacagctcc ggaagcagca ctcatccacg atgcttgtct gaggcgccgc cc              52

<210> SEQ ID NO 90
<211> LENGTH: 29
<212> TYPE: DNA
<213> ORGANISM: Artificial Sequence
<220> FEATURE:
<223> OTHER INFORMATION: PCR Primer

<400> SEQUENCE: 90
tgacactata gaataacatc cactttgcc                                        29

<210> SEQ ID NO 91
<211> LENGTH: 52
<212> TYPE: DNA
<213> ORGANISM: Artificial Sequence
<220> FEATURE:
<223> OTHER INFORMATION: PCR Primer

<400> SEQUENCE: 91
tcacagctcc ggaagcagca ctcatccacg atgggtgtct gaggcgccgc cc              52

<210> SEQ ID NO 92
<211> LENGTH: 29
<212> TYPE: DNA
<213> ORGANISM: Artificial Sequence
<220> FEATURE:
<223> OTHER INFORMATION: PCR Primer

<400> SEQUENCE: 92
tgacactata gaataacatc cactttgcc                                        29

<210> SEQ ID NO 93
<211> LENGTH: 76
<212> TYPE: DNA
<213> ORGANISM: Artificial Sequence
<220> FEATURE:
<223> OTHER INFORMATION: PCR Primer: hIGF1-Ea-hFc_mut4 reverse primer
<220> FEATURE:
<221> NAME/KEY: misc_feature
<222> LOCATION: (49)..(50)
<223> OTHER INFORMATION: n is a, c, g, or t

<400> SEQUENCE: 93
tcacagctcc ggaagcagca ctcatccacg atgcctgtct gaggcgcmnn ccgactgctg      60
gagccatacc ctgtgg                                                      76

<210> SEQ ID NO 94
<211> LENGTH: 29
<212> TYPE: DNA
```

```
<213> ORGANISM: Artificial Sequence
<220> FEATURE:
<223> OTHER INFORMATION: PCR Primer

<400> SEQUENCE: 94
tgacactata gaataacatc cactttgcc                                      29

<210> SEQ ID NO 95
<211> LENGTH: 43
<212> TYPE: DNA
<213> ORGANISM: Artificial Sequence
<220> FEATURE:
<223> OTHER INFORMATION: PCR Primer

<400> SEQUENCE: 95
tgtctgaggc gcccgcgcac tgctggagcc ataccctgtg ggc                      43

<210> SEQ ID NO 96
<211> LENGTH: 29
<212> TYPE: DNA
<213> ORGANISM: Artificial Sequence
<220> FEATURE:
<223> OTHER INFORMATION: PCR Primer

<400> SEQUENCE: 96
tgacactata gaataacatc cactttgcc                                      29

<210> SEQ ID NO 97
<211> LENGTH: 41
<212> TYPE: DNA
<213> ORGANISM: Artificial Sequence
<220> FEATURE:
<223> OTHER INFORMATION: PCR Primer

<400> SEQUENCE: 97
tgtctgaggc gccgcctgac tgctggagcc ataccctgtg g                        41

<210> SEQ ID NO 98
<211> LENGTH: 37
<212> TYPE: DNA
<213> ORGANISM: Artificial Sequence
<220> FEATURE:
<223> OTHER INFORMATION: PCR Primer

<400> SEQUENCE: 98
cggtacgtgc tggcgtactg ctcctcccgc ggctttg                             37

<210> SEQ ID NO 99
<211> LENGTH: 368
<212> TYPE: DNA
<213> ORGANISM: Artificial Sequence
<220> FEATURE:
<223> OTHER INFORMATION: mutated chinese hamster IGF1-Receptor gene
      fragment: CHOK1 derivative  clone 1: copy delta2

<400> SEQUENCE: 99
agcgtgcacc gagaacaacg aatgctgcca cccagagtgc ctaggcagct gccatacacc     60
tgacgacaac acaacctgtg tggcctgccg acactactac tacaaaggcg tgtgtgtgcc    120
tgcctgccca cctggcacct acgttcgagg gctggcgctg tgtggaccgc gatttctgcg    180
ccaacatccc caacgctgag agcagtgact cagatggctt tgtcatccac gatggcgagt    240
gcatgcaaga atgtccctca ggcttcatcc gcaacagcac ccagaggtca gtggctcttg    300
ttcccccatc aggaggtgaa tcttgttcat attccatgat tgtaggaacc acccagaggt    360
```

```
tcatccag                                                               368
```

<210> SEQ ID NO 100
<211> LENGTH: 365
<212> TYPE: DNA
<213> ORGANISM: Artificial Sequence
<220> FEATURE:
<223> OTHER INFORMATION: mutated chinese hamster IGF1-Receptor gene
      fragment: CHOK1 derivative knock out clone 2: copy delta5

<400> SEQUENCE: 100

```
agcgtgcacc gagaacaacg aatgctgcca cccagagtgc ctaggcagct gccatacacc    60
tgacgacaac acaacctgtg tggcctgccg acactactac tacaaaggcg tgtgtgtgcc   120
tgcctgccca cctggcacct acagagggct ggcgctgtgt ggaccgcgat ttctgcgcca   180
acatccccaa cgctgagagc agtgactcag atggctttgt catccacgat ggcgagtgca   240
tgcaagaatg tccctcaggc ttcatccgca acagcaccca gaggtcagtg gctcttgttc   300
cccatccagg aggtgaatct tgttcatatt ccatgattgt aggaaccacc cagaggttca   360
tccag                                                               365
```

<210> SEQ ID NO 101
<211> LENGTH: 368
<212> TYPE: DNA
<213> ORGANISM: Artificial Sequence
<220> FEATURE:
<223> OTHER INFORMATION: mutated chinese hamster IGF1-Receptor gene
      fragment: CHOK1 derivative knock out clone 3: copy delta2

<400> SEQUENCE: 101

```
agcgtgcacc gagaacaacg aatgctgcca cccagagtgc ctaggcagct gccatacacc    60
tgacgacaac acaacctgtg tggcctgccg acactactac tacaaaggcg tgtgtgtgcc   120
tgcctgccca cctggcacct acgttcgagg gctggcgctg tgtggaccgc gatttctgcg   180
ccaacatccc caacgctgag agcagtgact cagatggctt tgtcatccac gatggcgagt   240
gcatgcaaga atgtccctca ggcttcatcc gcaacagcac ccagaggtca gtggctcttg   300
ttccccatcc aggaggtgaa tcttgttcat attccatgat tgtaggaacc acccagaggt   360
tcatccag                                                            368
```

<210> SEQ ID NO 102
<211> LENGTH: 348
<212> TYPE: DNA
<213> ORGANISM: Artificial Sequence
<220> FEATURE:
<223> OTHER INFORMATION: mutated chinese hamster IGF1-Receptor gene
      fragment: CHOK1 derivative knock out clone 2: copy delta22

<400> SEQUENCE: 102

```
agcgtgcacc gagaacaacg aatgctgcca cccagagtgc ctaggcagct gccatacacc    60
tgacgacaac acaacctgtg tggcctgccg acactactac tacaaaggcg tgtgtgtgcc   120
tgcctgccca cctggcgctg tgtggaccgc gatttctgcg ccaacatccc caacgctgag   180
agcagtgact cagatggctt tgtcatccac gatggcgagt gcatgcaaga atgtccctca   240
ggcttcatcc gcaacagcac ccagaggtca gtggctcttg ttccccatcc aggaggtgaa   300
tcttgttcat attccatgat tgtaggaacc acccagaggt tcatccag                348
```

<210> SEQ ID NO 103
<211> LENGTH: 388
<212> TYPE: DNA

```
<213> ORGANISM: Artificial Sequence
<220> FEATURE:
<223> OTHER INFORMATION: mutated chinese hamster IGF1-Receptor gene
      fragment: CHOK1 derivative knock out clone 1: copy 14 nucleotides
      replaced and 18 added

<400> SEQUENCE: 103
agcgtgcacc gagaacaacg aatgctgcca cccagagtgc ctaggcagct gccatacacc      60
tgacgacaac acaacctgtg tggcctgccg acactactac tacaaaggcg tgtgtgtgcc     120
tgcctgccca cctggtgagg tataggacag tattatagag gtggggcagg gctggcgctg     180
tgtggaccgc gatttctgcg ccaacatccc caacgctgag agcagtgact cagatggctt     240
tgtcatccac gatggcgagt gcatgcaaga atgtccctca ggcttcatcc gcaacagcac     300
ccagaggtca gtggctcttg ttccccatcc aggaggtgaa tcttgttcat attccatgat     360
tgtaggaacc acccagaggt tcatccag                                        388

<210> SEQ ID NO 104
<211> LENGTH: 256
<212> TYPE: DNA
<213> ORGANISM: Artificial Sequence
<220> FEATURE:
<223> OTHER INFORMATION: mutated chinese hamster IGF1-Receptor gene
      fragment: CHOK1 derivative knock out clone 3: copy delta114

<400> SEQUENCE: 104
agcgtgcacc gagaacaacg aatgctgcca cccagagtgc tggcgctgtg tggaccgcga      60
tttctgcgcc aacatcccca acgctgagag cagtgactca gatggctttg tcatccacga    120
tggcgagtgc atgcaagaat gtccctcagg cttcatccgc aacagcaccc agaggtcagt    180
ggctcttgtt ccccatccag gaggtgaatc ttgttcatat tccatgattg taggaaccac    240
ccagaggttc atccag                                                    256

<210> SEQ ID NO 105
<211> LENGTH: 348
<212> TYPE: DNA
<213> ORGANISM: Artificial Sequence
<220> FEATURE:
<223> OTHER INFORMATION: mutated chinese hamster IGF1-Receptor gene
      fragment: CHO-DUXB11 derivative knock out clone: sequence delta22

<400> SEQUENCE: 105
agcgtgcacc gagaacaacg aatgctgcca cccagagtgc ctaggcagct gccatacacc      60
tgacgacaac acaacctgtg tggcctgccg acactactac tacaaaggcg tgtgtgtgcc     120
tgcctgccca cctggcgctg tgtggaccgc gatttctgcg ccaacatccc caacgctgag     180
agcagtgact cagatggctt tgtcatccac gatggcgagt gcatgcaaga atgtccctca     240
ggcttcatcc gcaacagcac ccagaggtca gtggctcttg ttccccatcc aggaggtgaa     300
tcttgttcat attccatgat tgtaggaacc acccagaggt tcatccag                  348

<210> SEQ ID NO 106
<211> LENGTH: 363
<212> TYPE: DNA
<213> ORGANISM: Artificial Sequence
<220> FEATURE:
<223> OTHER INFORMATION: mutated chinese hamster IGF1-Receptor gene
      fragment: CHO-DUXB11 derivative knock out clone: sequence delta7

<400> SEQUENCE: 106
agcgtgcacc gagaacaacg aatgctgcca cccagagtgc ctaggcagct gccatacacc      60
```

```
tgacgacaac acaacctgtg tggcctgccg acactactac tacaaaggcg tgtgtgtgcc      120
tgcctgccca cctggcacct acagggctgg cgctgtgtgg accgcgattt ctgcgccaac      180
atccccaacg ctgagagcag tgactcagat ggctttgtca tccacgatgg cgagtgcatg      240
caagaatgtc cctcaggctt catccgcaac agcacccaga ggtcagtggc tcttgttccc      300
catccaggag gtgaatcttg ttcatattcc atgattgtag gaaccaccca gaggttcatc      360
cag                                                                    363
```

<210> SEQ ID NO 107
<211> LENGTH: 41
<212> TYPE: DNA
<213> ORGANISM: Chinese Hamster

<400> SEQUENCE: 107

```
cccacctggc acctacaggt tcgagggctg gcgctgtgtg g                          41
```

<210> SEQ ID NO 108
<211> LENGTH: 20
<212> TYPE: DNA
<213> ORGANISM: Artificial Sequence
<220> FEATURE:
<223> OTHER INFORMATION: PCR Primer: CHO IGF1R forward sequencing primer
      (in intron 2-3)

<400> SEQUENCE: 108

```
ctagcctgtc tctgggacac                                                  20
```

<210> SEQ ID NO 109
<211> LENGTH: 20
<212> TYPE: DNA
<213> ORGANISM: Artificial Sequence
<220> FEATURE:
<223> OTHER INFORMATION: PCR Primer: CHO IGF1R reverse sequencing primer
      (in intron 3-4)

<400> SEQUENCE: 109

```
ctggatgaac ctctgggtgg                                                  20
```

<210> SEQ ID NO 110
<211> LENGTH: 313
<212> TYPE: DNA
<213> ORGANISM: Chinese Hamster

<400> SEQUENCE: 110

```
tgtgcccaag tgtgtgcgga aagcgagcgt gcaccgagaa caacgaatgc tgccacccag      60
agtgcctagg cagctgccat acacctgacg acaacacaac ctgtgtggcc tgccgacact      120
actactacaa aggcgtgtgt gtgcctgcct gcccacctgg cacctacagg ttcgagggct      180
ggcgctgtgt ggaccgcgat ttctgcgcca acatccccaa cgctgagagc agtgactcag      240
atggctttgt catccacgat ggcgagtgca tgcaagaatg tccctcaggc ttcatccgca      300
acagcaccca gag                                                         313
```

<210> SEQ ID NO 111
<211> LENGTH: 774
<212> TYPE: DNA
<213> ORGANISM: Chinese Hamster

<400> SEQUENCE: 111

```
aaacttaacg gcacatccca tagcaaacca tttcataaga aaggacttgg catgtgttgt      60
gtcctttccc agtgtgggct tcacagatgg tattacctgt gcagatttca gagaaagtgt      120
```

```
gtttttccta gcctgtctct gggacaccat ttagtgctgg ttgtggcagc agatgaccct    180
ggggaggctg tgtagtctct tcatctcacc acctcctccc cctgttccca cagtgtgccc    240
aagtgtgtgc ggaaagcgag cgtgcaccga aacaacgaa tgctgccacc cagagtgcct    300
aggcagctgc catacacctg acgacaacac aacctgtgtg gcctgccgac actactacta    360
caaaggcgtg tgtgtgcctg cctgcccacc tggcacctac aggttcgagg gctggcgctg    420
tgtggaccgc gatttctgcg ccaacatccc caacgctgag agcagtgact cagatggctt    480
tgtcatccac gatggcgagt gcatgcaaga atgtccctca ggcttcatcc gcaacagcac    540
ccagaggtca gtggctcttg ttccccatcc aggaggtgaa tcttgttcat attccatgat    600
tgtaggaacc acccagaggt tcatccagat ggggaggctg ttggagggtg ctgactaagc    660
ttgtttttat gagaatcttg gaatggctgg tctgttcatt tctttgtttg ttggcttgct    720
ttgttgtctt tgaaagtgcc ttgctagccc tagagaggaa gaattagcct gctg           774
```

<210> SEQ ID NO 112
<211> LENGTH: 14
<212> TYPE: DNA
<213> ORGANISM: Artificial Sequence
<220> FEATURE:
<223> OTHER INFORMATION: Kozak sequence

<400> SEQUENCE: 112

```
cccgcccgcc cacc                                                       14
```

<210> SEQ ID NO 113
<211> LENGTH: 329
<212> TYPE: PRT
<213> ORGANISM: Artificial Sequence
<220> FEATURE:
<223> OTHER INFORMATION: Mutated human IGF-1 protein: hIGF1-Ea-del1-3,
      R37A, del71-72, R74Q, R77Q, R104Q-fc

<400> SEQUENCE: 113

```
Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Val Gln Ala Gln Gln His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Gln Met Gly Ser Asp Lys Thr His Thr Cys Pro Pro Cys Pro
            100                 105                 110

Ala Pro Glu Ala Ala Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175
```

```
Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 114
<211> LENGTH: 329
<212> TYPE: PRT
<213> ORGANISM: Artificial Sequence
<220> FEATURE:
<223> OTHER INFORMATION: Mutated human IGF-1 protein: hIGF1-Ea-hFc_mut03

<400> SEQUENCE: 114

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Ala Ala Pro Gln Thr Pro Ile Val Asp Glu Cys Cys Phe Arg Ser
        35                  40                  45

Cys Asp Leu Arg Arg Leu Glu Met Tyr Cys Ala Pro Leu Lys Pro Ala
50                  55                  60

Lys Ser Ala Val Gln Ala Gln Gln His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Gln Met Gly Ser Asp Lys Thr His Thr Cys Pro Pro Cys Pro
            100                 105                 110

Ala Pro Glu Ala Ala Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205
```

Ala Leu Pro Ala Pro Ile Glu Lys Thr Ile Ser Lys Ala Lys Gly Gln
210                215                220

Pro Arg Glu Pro Gln Val Tyr Thr Leu Pro Pro Ser Arg Glu Glu Met
225                230                235                240

Thr Lys Asn Gln Val Ser Leu Thr Cys Leu Val Lys Gly Phe Tyr Pro
            245                250                255

Ser Asp Ile Ala Val Glu Trp Glu Ser Asn Gly Gln Pro Glu Asn Asn
        260                265                270

Tyr Lys Thr Thr Pro Pro Val Leu Asp Ser Asp Gly Ser Phe Phe Leu
            275                280                285

Tyr Ser Lys Leu Thr Val Asp Lys Ser Arg Trp Gln Gln Gly Asn Val
        290                295                300

Phe Ser Cys Ser Val Met His Glu Ala Leu His Asn His Tyr Thr Gln
305                310                315                320

Lys Ser Leu Ser Leu Ser Pro Gly Lys
            325

<210> SEQ ID NO 115
<211> LENGTH: 33
<212> TYPE: PRT
<213> ORGANISM: Artificial Sequence
<220> FEATURE:
<223> OTHER INFORMATION: mutated human IGF-1 Ea peptide

<400> SEQUENCE: 115

Val Gln Ala Gln Gln His Thr Asp Met Pro Lys Thr Gln Lys Glu Val
1               5                   10                  15

His Leu Lys Asn Ala Ser Arg Gly Ser Ala Gly Asn Lys Asn Tyr Gln
            20                  25                  30

Met

<210> SEQ ID NO 116
<211> LENGTH: 329
<212> TYPE: PRT
<213> ORGANISM: Artificial Sequence
<220> FEATURE:
<223> OTHER INFORMATION: Mutated human IGF-1 protein: hIGF1-Ea-hFc_mut
      12

<400> SEQUENCE: 116

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Ala Arg Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Val Gln Ala Gln Gln His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Gln Met Gly Ser Asp Lys Thr His Thr Cys Pro Pro Cys Pro
            100                 105                 110

Ala Pro Glu Ala Ala Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

```
Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
            165                 170                 175

Gln Tyr Asn Ser Thr Tyr Arg Val Val Ser Val Leu Thr Val Leu His
        180                 185                 190

Gln Asp Trp Leu Asn Gly Lys Glu Tyr Lys Cys Lys Val Ser Asn Lys
            195                 200                 205

Ala Leu Pro Ala Pro Ile Glu Lys Thr Ile Ser Lys Ala Lys Gly Gln
        210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 117
<211> LENGTH: 70
<212> TYPE: PRT
<213> ORGANISM: Artificial Sequence
<220> FEATURE:
<223> OTHER INFORMATION: Mutated human IGF-1 protein: IGF-1 (G42S)

<400> SEQUENCE: 117

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Ser Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 118
<211> LENGTH: 102
<212> TYPE: PRT
<213> ORGANISM: Artificial Sequence
<220> FEATURE:
<223> OTHER INFORMATION: Mutated human IGF-1 protein: hIGF1-Ea-mut 03-
      G42S

<400> SEQUENCE: 118

Gly Pro Thr Leu Cys Gly Ala Glu Leu Val Asp Ala Leu Gln Phe Val
1               5                   10                  15

Cys Gly Asp Arg Gly Phe Tyr Phe Asn Lys Pro Thr Gly Tyr Gly Ser
            20                  25                  30
```

```
Ser Ser Arg Ala Ala Pro Gln Thr Ser Ile Val Asp Glu Cys Cys Phe
    35              40              45

Arg Ser Cys Asp Leu Arg Leu Glu Met Tyr Cys Ala Pro Leu Lys
    50              55              60

Pro Ala Lys Ser Ala Val Arg Ala Gln Arg His Thr Asp Met Pro Lys
65              70              75              80

Thr Gln Lys Glu Val His Leu Lys Asn Ala Ser Arg Gly Ser Ala Gly
                85              90              95

Asn Lys Asn Tyr Arg Met
            100
```